(12) United States Patent
Orton et al.

(10) Patent No.: US 9,443,633 B2
(45) Date of Patent: Sep. 13, 2016

(54) ELECTROMAGNETICALLY ACTUATED MULTI-LEAF COLLIMATOR

(71) Applicant: Accuray Incorporated, Sunnyvale, CA (US)

(72) Inventors: Matthew J. Orton, Oregon, WI (US); Robert Mastromattei, Loomis, CA (US); Robert O'Connell, Madison, WI (US); Richard C. Schmidt, Verona, WI (US); Graham Reitz, Madison, WI (US)

(73) Assignee: ACCURAY INCORPORATED, Sunnyvale, CA (US)

( * ) Notice: Subject to any disclaimer, the term of this patent is extended or adjusted under 35 U.S.C. 154(b) by 0 days.

(21) Appl. No.: 14/184,568

(22) Filed: Feb. 19, 2014

(65) Prior Publication Data

US 2014/0239204 A1   Aug. 28, 2014

Related U.S. Application Data

(60) Provisional application No. 61/769,549, filed on Feb. 26, 2013.

(51) Int. Cl.
*G21K 1/02*  (2006.01)
*G21K 1/04*  (2006.01)

(52) U.S. Cl.
CPC ..................... *G21K 1/046* (2013.01)

(58) Field of Classification Search
CPC ............. A61N 5/1045; A61N 5/1047; A61N 5/1042; G21K 1/046; G21K 1/043; H02K 1/17; H02K 41/03; H02K 41/031; H02K 41/0356

USPC .......... 250/505.1, 492.1; 378/147, 151, 152, 378/64, 65

See application file for complete search history.

(56) References Cited

U.S. PATENT DOCUMENTS

| | | | |
|---|---|---|---|
| 2,506,887 A | 5/1950 | Orser | |
| 2,570,820 A | 10/1951 | Knab | |
| 2,781,454 A | 2/1957 | Green et al. | |

(Continued)

FOREIGN PATENT DOCUMENTS

| | | |
|---|---|---|
| CA | 2091275 | 9/1993 |
| CA | 2180227 | 12/1996 |

(Continued)

OTHER PUBLICATIONS

PCT Search Report and Written Opinion for PCT Application No. PCT/US2014/017198 dated Sep. 2, 2014 (20 pages).

(Continued)

*Primary Examiner* — Wyatt Stoffa
(74) *Attorney, Agent, or Firm* — Michael Best Friedrich LLP

(57) ABSTRACT

A multi-leaf collimator with electromagnetically actuated leaves. The multi-leaf collimator includes a plurality of leaves, a leaf guide configured to support the plurality of leaves, and a plurality of magnets. Each leaf includes a blocking portion that is radio opaque, a drive portion connected to the blocking portion, and a coil embedded in the drive portion. The coil is operatively connected to an electrical current source to generate a first magnetic field. The first magnetic field interacts with the magnetic field generated by the magnet to thereby move the leave to a desired state. The leaves have the capability of moving at speeds of 50 cm/s up to and higher than 1 m/s.

20 Claims, 26 Drawing Sheets

(56) References Cited

U.S. PATENT DOCUMENTS

| | | |
|---|---|---|
| 2,793,296 A | 5/1957 | Peterson, Jr. |
| 3,130,313 A * | 4/1964 | Tilling ..................... A61B 6/06 378/151 |
| 3,348,114 A | 10/1967 | Wright, Jr. et al. |
| 3,497,786 A | 2/1970 | Lombardo |
| 3,675,099 A | 7/1972 | Johnston |
| 3,714,592 A | 1/1973 | Jory |
| 3,755,712 A | 8/1973 | DeViney et al. |
| 3,820,035 A | 6/1974 | Meddaugh |
| 3,840,221 A | 10/1974 | Hogan |
| 3,851,233 A | 11/1974 | Sherman |
| 3,949,265 A | 4/1976 | Holl |
| 3,964,467 A | 6/1976 | Rose |
| 3,965,434 A | 6/1976 | Helgesson |
| 3,974,384 A | 8/1976 | Winkler |
| 4,006,422 A | 2/1977 | Schriber |
| 4,032,810 A | 6/1977 | Eastham et al. |
| 4,034,224 A | 7/1977 | Heavens et al. |
| 4,107,617 A | 8/1978 | Tran |
| 4,131,802 A | 12/1978 | Braden et al. |
| 4,145,612 A | 3/1979 | Cooper |
| 4,149,081 A | 4/1979 | Seppi |
| 4,162,459 A | 7/1979 | Scharfman |
| 4,181,894 A | 1/1980 | Pottier |
| 4,189,470 A | 2/1980 | Rose |
| 4,208,185 A | 6/1980 | Sawai et al. |
| 4,273,867 A | 6/1981 | Lin et al. |
| 4,294,781 A | 10/1981 | Holmquist |
| 4,314,180 A | 2/1982 | Salisbury |
| 4,323,780 A | 4/1982 | Tombaugh et al. |
| 4,335,465 A | 6/1982 | Christiansen et al. |
| 4,354,112 A | 10/1982 | Nishio |
| 4,361,902 A * | 11/1982 | Brandt ..................... G21K 1/04 378/150 |
| 4,388,560 A | 6/1983 | Robinson et al. |
| 4,393,334 A | 7/1983 | Glaser |
| 4,395,631 A | 7/1983 | Salisbury |
| 4,401,765 A | 8/1983 | Craig et al. |
| 4,426,582 A | 1/1984 | Orloff et al. |
| 4,446,403 A | 5/1984 | Cuomo et al. |
| 4,455,609 A | 6/1984 | Inamura et al. |
| 4,477,921 A | 10/1984 | Armini et al. |
| 4,480,042 A | 10/1984 | Craig et al. |
| 4,570,103 A | 2/1986 | Schoen |
| 4,664,869 A | 5/1987 | Mirzadeh et al. |
| 4,703,018 A | 10/1987 | Craig et al. |
| 4,713,581 A | 12/1987 | Haimson |
| 4,715,056 A | 12/1987 | Vlasbloem et al. |
| 4,736,106 A | 4/1988 | Kashy et al. |
| 4,736,736 A | 4/1988 | Moers et al. |
| 4,737,647 A | 4/1988 | Stieber |
| 4,752,692 A | 6/1988 | Jergenson et al. |
| 4,754,760 A | 7/1988 | Fukukita et al. |
| 4,801,848 A | 1/1989 | Birnbach et al. |
| 4,815,446 A | 3/1989 | McIntosh |
| 4,818,914 A | 4/1989 | Brodie |
| 4,868,843 A | 9/1989 | Nunan |
| 4,868,844 A | 9/1989 | Nunan |
| 4,870,287 A | 9/1989 | Cole et al. |
| 4,879,518 A | 11/1989 | Broadhurst |
| 4,880,222 A | 11/1989 | Dragmen, Sr. |
| 4,912,731 A | 3/1990 | Nardi |
| 4,936,308 A | 6/1990 | Fukukita et al. |
| 4,965,726 A | 10/1990 | Heuscher et al. |
| 4,987,309 A | 1/1991 | Klasen et al. |
| 4,987,583 A | 1/1991 | Travanty et al. |
| 4,988,866 A | 1/1991 | Westerlund |
| 4,998,268 A | 3/1991 | Winter |
| 5,003,998 A | 4/1991 | Collett |
| 5,008,907 A | 4/1991 | Norman et al. |
| 5,012,111 A | 4/1991 | Ueda |
| 5,027,818 A | 7/1991 | Bova et al. |
| 5,044,354 A | 9/1991 | Goldhorn et al. |
| 5,046,708 A | 9/1991 | Schaefer |
| 5,052,034 A | 9/1991 | Schuster |
| 5,065,315 A | 11/1991 | Garcia |
| 5,072,384 A | 12/1991 | Doi et al. |
| 5,073,913 A | 12/1991 | Martin |
| 5,084,682 A | 1/1992 | Swenson et al. |
| 5,103,103 A | 4/1992 | Radford et al. |
| 5,105,141 A | 4/1992 | Ernest |
| 5,107,222 A | 4/1992 | Tsuzuki |
| 5,113,420 A | 5/1992 | Davis, Jr. et al. |
| 5,117,445 A | 5/1992 | Seppi et al. |
| 5,117,829 A | 6/1992 | Miller et al. |
| 5,124,658 A | 6/1992 | Adler |
| 5,138,647 A | 8/1992 | Nguyen et al. |
| 5,165,106 A | 11/1992 | Barthelmes et al. |
| 5,210,414 A | 5/1993 | Wallace et al. |
| 5,210,893 A | 5/1993 | Uosaki et al. |
| 5,250,388 A | 10/1993 | Schoch, Jr. et al. |
| 5,317,616 A * | 5/1994 | Swerdloff ................. A61B 6/00 378/151 |
| 5,321,271 A | 6/1994 | Schonberg et al. |
| 5,332,908 A | 7/1994 | Weidlich |
| 5,335,255 A | 8/1994 | Seppi et al. |
| 5,346,548 A | 9/1994 | Mehta |
| 5,351,280 A | 9/1994 | Swerdloff et al. |
| 5,382,914 A | 1/1995 | Hamm et al. |
| 5,391,139 A | 2/1995 | Edmundson |
| 5,394,452 A * | 2/1995 | Swerdloff ............ A61N 5/1042 378/150 |
| 5,405,309 A | 4/1995 | Carden, Jr. |
| 5,442,675 A | 8/1995 | Swerdloff et al. |
| 5,446,548 A | 8/1995 | Gerig et al. |
| 5,453,310 A | 9/1995 | Andersen et al. |
| 5,466,587 A | 11/1995 | Fitzpatrick-McElligott et al. |
| 5,471,516 A | 11/1995 | Nunan |
| 5,483,122 A | 1/1996 | Derbenev et al. |
| 5,489,780 A | 2/1996 | Diamondis |
| 5,511,549 A | 4/1996 | Legg et al. |
| 5,519,266 A * | 5/1996 | Chitayat .................. H02K 1/16 310/12.01 |
| 5,523,578 A | 6/1996 | Herskovic |
| 5,528,650 A | 6/1996 | Swerdloff et al. |
| 5,548,627 A | 8/1996 | Swerdloff et al. |
| 5,552,605 A | 9/1996 | Arata |
| 5,569,175 A | 10/1996 | Chitwood |
| 5,576,602 A | 11/1996 | Hiramoto et al. |
| 5,578,909 A | 11/1996 | Billen |
| 5,579,358 A | 11/1996 | Lin |
| 5,579,409 A | 11/1996 | Vaidyanathan et al. |
| 5,581,156 A | 12/1996 | Roberts et al. |
| 5,591,983 A | 1/1997 | Yao |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,190 A | 4/1997 | Crandall |
| 5,625,663 A | 4/1997 | Swerdloff et al. |
| 5,627,041 A | 5/1997 | Shartle |
| 5,627,367 A | 5/1997 | Sofield |
| 5,633,948 A | 5/1997 | Kegelmeyer, Jr. |
| 5,641,584 A | 6/1997 | Andersen et al. |
| 5,647,663 A | 7/1997 | Holmes |
| 5,651,043 A | 7/1997 | Tsuyuki et al. |
| 5,657,498 A | 8/1997 | Hum |
| 5,661,377 A | 8/1997 | Mishin et al. |
| 5,661,773 A | 8/1997 | Swerdloff et al. |
| 5,667,803 A | 9/1997 | Paronen et al. |
| 5,668,371 A * | 9/1997 | Deasy .................. A61N 5/1042 250/505.1 |
| 5,673,300 A | 9/1997 | Reckwerdt et al. |
| 5,692,507 A | 12/1997 | Seppi et al. |
| 5,695,443 A | 12/1997 | Brent et al. |
| 5,712,482 A | 1/1998 | Gaiser et al. |
| 5,721,123 A | 2/1998 | Hayes et al. |
| 5,724,400 A | 3/1998 | Swerdloff et al. |
| 5,729,028 A | 3/1998 | Rose |
| 5,734,168 A | 3/1998 | Yao |
| 5,744,919 A | 4/1998 | Mishin et al. |
| 5,747,254 A | 5/1998 | Pontius |
| 5,748,703 A | 5/1998 | Cosman |
| 5,751,781 A | 5/1998 | Brown et al. |

(56) References Cited

U.S. PATENT DOCUMENTS

| | | | |
|---|---|---|---|
| 5,753,308 A | 5/1998 | Andersen et al. | |
| 5,754,622 A | 5/1998 | Hughes | |
| 5,754,623 A | 5/1998 | Seki | |
| 5,757,885 A | 5/1998 | Yao et al. | |
| 5,760,395 A | 6/1998 | Johnstone | |
| 5,761,331 A | 6/1998 | Clark, III | |
| 5,771,270 A | 6/1998 | Archer | |
| 5,771,513 A | 6/1998 | Kirchgeorg et al. | |
| 5,791,599 A | 8/1998 | Blackburn et al. | |
| 5,800,353 A | 9/1998 | McLaurin, Jr. | |
| 5,802,136 A | 9/1998 | Carol | |
| 5,810,707 A | 9/1998 | Montebello et al. | |
| 5,811,944 A | 9/1998 | Sampayan et al. | |
| 5,815,547 A | 9/1998 | Shepherd et al. | |
| 5,818,058 A | 10/1998 | Nakanishi et al. | |
| 5,818,902 A | 10/1998 | Yu | |
| 5,820,553 A | 10/1998 | Hughes | |
| 5,821,051 A | 10/1998 | Androphy et al. | |
| 5,821,694 A | 10/1998 | Young | |
| 5,821,705 A | 10/1998 | Caporaso et al. | |
| 5,823,192 A | 10/1998 | Kalend et al. | |
| 5,834,454 A | 11/1998 | Kitano et al. | |
| 5,835,562 A | 11/1998 | Ramsdell et al. | |
| 5,836,905 A | 11/1998 | Lemelson et al. | |
| 5,838,765 A | 11/1998 | Gershman et al. | |
| 5,842,175 A | 11/1998 | Andros et al. | |
| 5,866,912 A | 2/1999 | Slater et al. | |
| 5,869,837 A | 2/1999 | Huang | |
| 5,870,447 A | 2/1999 | Powell et al. | |
| 5,870,697 A | 2/1999 | Chandler et al. | |
| 5,877,023 A | 3/1999 | Sautter et al. | |
| 5,877,192 A | 3/1999 | Lindberg et al. | |
| 5,901,199 A | 5/1999 | Murphy et al. | |
| 5,907,594 A | 5/1999 | Lai | |
| 5,912,134 A | 6/1999 | Shartle | |
| 5,920,601 A | 7/1999 | Nigg et al. | |
| 5,940,469 A | 8/1999 | Hell et al. | |
| 5,947,981 A | 9/1999 | Cosman | |
| 5,949,080 A | 9/1999 | Ueda et al. | |
| 5,953,461 A | 9/1999 | Yamada | |
| 5,954,650 A | 9/1999 | Saito et al. | |
| 5,961,454 A | 10/1999 | Kooy et al. | |
| 5,962,995 A | 10/1999 | Avnery | |
| 5,963,615 A | 10/1999 | Egley et al. | |
| 5,963,664 A | 10/1999 | Kumar et al. | |
| 5,969,367 A | 10/1999 | Hiramoto et al. | |
| 5,970,499 A | 10/1999 | Smith et al. | |
| 5,977,100 A | 11/1999 | Kitano et al. | |
| 5,983,424 A | 11/1999 | Näslund | |
| 5,986,274 A | 11/1999 | Akiyama et al. | |
| 6,009,212 A | 12/1999 | Miller et al. | |
| 6,011,825 A | 1/2000 | Welch et al. | |
| 6,020,135 A | 2/2000 | Levine et al. | |
| 6,020,538 A | 2/2000 | Han et al. | |
| 6,029,079 A | 2/2000 | Cox et al. | |
| 6,038,283 A | 3/2000 | Carol et al. | |
| 6,045,262 A | 4/2000 | Igeta et al. | |
| 6,047,259 A | 4/2000 | Campbell et al. | |
| 6,049,587 A | 4/2000 | Leksell et al. | |
| 6,054,694 A | 4/2000 | Paustian | |
| 6,060,833 A | 5/2000 | Velazco | |
| 6,066,927 A | 5/2000 | Koudijs | |
| 6,069,459 A | 5/2000 | Koudijs | |
| 6,071,748 A | 6/2000 | Modlin et al. | |
| 6,094,760 A | 8/2000 | Nonaka et al. | |
| 6,104,108 A * | 8/2000 | Hazelton | G03F 7/70758 310/12.06 |
| 6,127,688 A | 10/2000 | Wu | |
| 6,141,400 A | 10/2000 | Schardt et al. | |
| 6,144,875 A | 11/2000 | Schweikard et al. | |
| 6,152,599 A | 11/2000 | Salter, Jr. | |
| 6,155,976 A | 12/2000 | Sackner et al. | |
| 6,167,296 A | 12/2000 | Shahidi | |
| 6,171,798 B1 | 1/2001 | Levine et al. | |
| 6,178,345 B1 | 1/2001 | Vilsmeier et al. | |
| 6,197,328 B1 | 3/2001 | Yanagawa | |
| 6,198,957 B1 | 3/2001 | Green | |
| 6,200,959 B1 | 3/2001 | Haynes et al. | |
| 6,204,510 B1 | 3/2001 | Ohkawa | |
| 6,207,400 B1 | 3/2001 | Kwon | |
| 6,207,952 B1 | 3/2001 | Kan et al. | |
| 6,217,214 B1 | 4/2001 | Cabral et al. | |
| 6,218,675 B1 | 4/2001 | Akiyama et al. | |
| 6,222,905 B1 | 4/2001 | Yoda et al. | |
| 6,241,670 B1 | 6/2001 | Nambu | |
| 6,242,747 B1 | 6/2001 | Sugitani et al. | |
| 6,260,005 B1 | 7/2001 | Yang et al. | |
| 6,264,825 B1 | 7/2001 | Blackburn et al. | |
| 6,265,837 B1 | 7/2001 | Akiyama et al. | |
| 6,266,453 B1 | 7/2001 | Hibbard et al. | |
| 6,279,579 B1 | 8/2001 | Riaziat et al. | |
| 6,282,257 B1 | 8/2001 | Basu et al. | |
| 6,291,823 B1 | 9/2001 | Doyle et al. | |
| 6,301,329 B1 | 10/2001 | Surridge | |
| 6,315,783 B1 | 11/2001 | Katz et al. | |
| 6,316,776 B1 | 11/2001 | Hiramoto et al. | |
| 6,319,469 B1 | 11/2001 | Mian et al. | |
| 6,322,249 B1 | 11/2001 | Wofford et al. | |
| 6,324,243 B1 | 11/2001 | Edic et al. | |
| 6,331,194 B1 | 12/2001 | Sampayan et al. | |
| 6,345,114 B1 | 2/2002 | Mackie et al. | |
| 6,360,116 B1 | 3/2002 | Jackson, Jr. et al. | |
| 6,385,286 B1 | 5/2002 | Fitchard et al. | |
| 6,385,288 B1 | 5/2002 | Kanematsu | |
| 6,393,096 B1 | 5/2002 | Carol et al. | |
| 6,401,055 B1 | 6/2002 | Petta | |
| 6,405,072 B1 | 6/2002 | Cosman | |
| 6,407,505 B1 | 6/2002 | Bertsche | |
| 6,407,646 B1 | 6/2002 | Johnson | |
| 6,417,178 B1 | 7/2002 | Klunk et al. | |
| 6,422,748 B1 | 7/2002 | Shepherd et al. | |
| 6,424,856 B1 | 7/2002 | Vilsmeier et al. | |
| 6,428,547 B1 | 8/2002 | Vilsmeier et al. | |
| 6,433,349 B2 | 8/2002 | Akiyama et al. | |
| 6,438,202 B1 * | 8/2002 | Olivera | A61N 5/1048 378/152 |
| 6,442,777 B1 | 9/2002 | Pauli | |
| 6,454,460 B1 | 9/2002 | Ramanathan et al. | |
| 6,455,844 B1 | 9/2002 | Meyer | |
| 6,459,769 B1 | 10/2002 | Cosman | |
| 6,462,490 B1 | 10/2002 | Matsuda et al. | |
| 6,463,123 B1 | 10/2002 | Korenev | |
| 6,465,957 B1 | 10/2002 | Whitham et al. | |
| 6,466,644 B1 | 10/2002 | Hughes et al. | |
| 6,469,058 B1 | 10/2002 | Grove et al. | |
| 6,472,834 B2 | 10/2002 | Hiramoto et al. | |
| 6,473,490 B1 | 10/2002 | Siochi | |
| 6,475,994 B2 | 11/2002 | Tomalia et al. | |
| 6,477,221 B1 | 11/2002 | Ning | |
| 6,477,229 B1 | 11/2002 | Grosser | |
| 6,482,604 B2 | 11/2002 | Kwon | |
| 6,484,049 B1 | 11/2002 | Seeley et al. | |
| 6,484,144 B2 | 11/2002 | Martin et al. | |
| 6,487,274 B2 | 11/2002 | Bertsche | |
| 6,491,636 B2 | 12/2002 | Chenal et al. | |
| 6,493,424 B2 | 12/2002 | Whitham | |
| 6,497,358 B1 | 12/2002 | Walsh | |
| 6,498,011 B2 | 12/2002 | Hohn et al. | |
| 6,500,343 B2 | 12/2002 | Siddiqi | |
| 6,504,899 B2 | 1/2003 | Pugachev et al. | |
| 6,510,199 B1 | 1/2003 | Hughes et al. | |
| 6,512,942 B1 | 1/2003 | Burdette et al. | |
| 6,516,046 B1 | 2/2003 | Fröhlich et al. | |
| 6,527,443 B1 | 3/2003 | Vilsmeier et al. | |
| 6,528,803 B1 | 3/2003 | Ritt | |
| 6,530,873 B1 | 3/2003 | Lee | |
| 6,531,449 B2 | 3/2003 | Khojasteh et al. | |
| 6,535,837 B1 | 3/2003 | Schach Von Wittenau | |
| 6,539,247 B2 | 3/2003 | Spetz | |
| 6,552,338 B1 | 4/2003 | Doyle | |
| 6,558,961 B1 | 5/2003 | Sarphie et al. | |
| 6,560,311 B1 * | 5/2003 | Shepard | G06F 19/3481 378/64 |
| 6,562,376 B2 | 5/2003 | Hooper et al. | |

(56) References Cited

U.S. PATENT DOCUMENTS

| | | |
|---|---|---|
| 6,568,449 B2 | 5/2003 | Owen et al. |
| 6,584,174 B2 | 6/2003 | Schubert et al. |
| 6,586,409 B1 | 7/2003 | Wheeler |
| 6,605,297 B2 | 8/2003 | Nadachi et al. |
| 6,611,700 B1 | 8/2003 | Vilsmeier et al. |
| 6,615,428 B1 | 9/2003 | Pattee |
| 6,617,768 B1 | 9/2003 | Hansen |
| 6,618,467 B1 | 9/2003 | Ruchala et al. |
| 6,621,889 B1 | 9/2003 | Mostafavi |
| 6,633,686 B1 | 10/2003 | Bakircioglu et al. |
| 6,634,790 B1 | 10/2003 | Salter, Jr. |
| 6,636,622 B2 | 10/2003 | Mackie et al. |
| 6,637,056 B1 | 10/2003 | Tybinkowski et al. |
| 6,646,383 B2 | 11/2003 | Bertsche et al. |
| 6,653,547 B2 | 11/2003 | Akamatsu |
| 6,653,806 B1 | 11/2003 | Ono |
| 6,661,870 B2 | 12/2003 | Kapatoes et al. |
| 6,675,116 B1 | 1/2004 | Ritt |
| 6,687,654 B2 | 2/2004 | Smith, Jr. et al. |
| 6,688,187 B1 | 2/2004 | Masquelier |
| 6,690,965 B1 | 2/2004 | Riaziat et al. |
| 6,697,452 B2 | 2/2004 | Xing |
| 6,705,984 B1 | 3/2004 | Angha |
| 6,708,184 B2 | 3/2004 | Smith et al. |
| 6,710,362 B2 | 3/2004 | Kraft et al. |
| 6,713,668 B2 | 3/2004 | Akamatsu |
| 6,713,976 B1 | 3/2004 | Zumoto et al. |
| 6,714,620 B2 | 3/2004 | Caflisch et al. |
| 6,714,629 B2 | 3/2004 | Vilsmeier |
| 6,716,162 B2 | 4/2004 | Hakamata |
| 6,719,683 B2 | 4/2004 | Fröhlich |
| 6,723,334 B1 | 4/2004 | McGee et al. |
| 6,731,970 B2 | 5/2004 | Schlossbauer et al. |
| 6,735,277 B2 | 5/2004 | McNutt et al. |
| 6,741,674 B2 | 5/2004 | Lee |
| 6,754,376 B1 | 6/2004 | Turek et al. |
| 6,757,355 B1 | 6/2004 | Siochi |
| 6,760,402 B2 | 7/2004 | Ghelmansarai |
| 6,769,145 B1 | 8/2004 | Pfeuffer et al. |
| 6,774,383 B2 | 8/2004 | Norimine et al. |
| 6,787,771 B2 | 9/2004 | Bashkirov et al. |
| 6,787,983 B2 | 9/2004 | Yamanobe et al. |
| 6,788,764 B2 | 9/2004 | Saladin et al. |
| 6,792,073 B2 | 9/2004 | Wickerhauser et al. |
| 6,792,074 B2 | 9/2004 | Erbel et al. |
| 6,792,078 B2 | 9/2004 | Kato et al. |
| 6,796,164 B2 | 9/2004 | McLoughlin et al. |
| 6,800,866 B2 | 10/2004 | Amemiya et al. |
| 6,801,019 B2 | 10/2004 | Haydock et al. |
| 6,804,548 B2 | 10/2004 | Takahashi et al. |
| 6,810,107 B2 | 10/2004 | Steinberg |
| 6,810,109 B2 | 10/2004 | Chornenky |
| 6,822,244 B2 | 11/2004 | Beloussov et al. |
| 6,822,247 B2 | 11/2004 | Sasaki |
| 6,826,313 B2 | 11/2004 | Robar et al. |
| 6,838,676 B1 | 1/2005 | Jackson |
| 6,842,502 B2 | 1/2005 | Jaffray et al. |
| 6,844,689 B1 | 1/2005 | Brown et al. |
| 6,853,702 B2 | 2/2005 | Renner |
| 6,857,147 B2 | 2/2005 | Somasundaram |
| 6,865,253 B2 | 3/2005 | Blumhofer et al. |
| 6,865,254 B2 | 3/2005 | Näfstadius |
| 6,865,411 B2 | 3/2005 | Erbel et al. |
| 6,869,428 B2 | 3/2005 | Sagehashi et al. |
| 6,871,171 B1 | 3/2005 | Agur et al. |
| 6,873,115 B2 | 3/2005 | Sagawa et al. |
| 6,873,123 B2 | 3/2005 | Marchand et al. |
| 6,878,951 B2 | 4/2005 | Ma |
| 6,882,702 B2 | 4/2005 | Luo |
| 6,882,705 B2 | 4/2005 | Egley et al. |
| 6,888,326 B2 | 5/2005 | Amaldi et al. |
| 6,888,919 B2 | 5/2005 | Graf |
| 6,889,695 B2 | 5/2005 | Pankratov et al. |
| 6,891,178 B2 | 5/2005 | Xing |
| 6,895,617 B2 | 5/2005 | Zacharopoulos et al. |
| 6,898,456 B2 | 5/2005 | Erbel |
| 6,904,125 B2 | 6/2005 | Van Dyk et al. |
| 6,906,493 B1 | 6/2005 | Ramirez, Jr. et al. |
| 6,907,282 B2 | 6/2005 | Siochi |
| 6,914,959 B2 | 7/2005 | Bailey et al. |
| 6,915,005 B1 | 7/2005 | Ruchala et al. |
| 6,920,203 B2 | 7/2005 | Short et al. |
| 6,922,455 B2 | 7/2005 | Jurczyk et al. |
| 6,929,398 B1 | 8/2005 | Tybinkowski et al. |
| 6,932,807 B1 | 8/2005 | Tomita et al. |
| 6,934,358 B2 | 8/2005 | Ritt et al. |
| 6,934,653 B2 | 8/2005 | Ritt |
| 6,936,832 B2 | 8/2005 | Norimine et al. |
| 6,937,693 B2 | 8/2005 | Svatos |
| 6,937,751 B2 | 8/2005 | Ritt et al. |
| 6,950,544 B2 | 9/2005 | Ashton |
| 6,955,464 B1 | 10/2005 | Tybinkowski et al. |
| 6,961,405 B2 | 11/2005 | Scherch |
| 6,963,171 B2 | 11/2005 | Sagawa et al. |
| 6,963,771 B2 | 11/2005 | Scarantino et al. |
| 6,974,254 B2 | 12/2005 | Paliwal et al. |
| 6,977,984 B2 | 12/2005 | Hsieh et al. |
| 6,984,835 B2 | 1/2006 | Harada |
| 6,990,167 B2 | 1/2006 | Chen |
| 6,999,556 B2 | 2/2006 | Nakano |
| 7,003,828 B2 | 2/2006 | Roussy |
| 7,008,105 B2 | 3/2006 | Amann et al. |
| 7,013,228 B2 | 3/2006 | Ritt |
| 7,015,490 B2 | 3/2006 | Wang et al. |
| 7,016,464 B2 | 3/2006 | Ritt et al. |
| 7,020,315 B2 | 3/2006 | Vaisburd et al. |
| 7,022,994 B2 | 4/2006 | Fuchs |
| 7,024,026 B1 | 4/2006 | Ritt et al. |
| 7,028,356 B2 | 4/2006 | Somasundaram |
| 7,043,058 B2 | 5/2006 | Cornog et al. |
| 7,046,762 B2 | 5/2006 | Lee |
| 7,046,831 B2 | 5/2006 | Ruchala et al. |
| 7,051,605 B2 | 5/2006 | Lagraff et al. |
| 7,054,413 B2 | 5/2006 | Steinberg |
| 7,060,997 B2 | 6/2006 | Norimine et al. |
| 7,077,569 B1 | 7/2006 | Tybinkowski et al. |
| 7,081,619 B2 | 7/2006 | Bashkirov et al. |
| 7,084,410 B2 | 8/2006 | Beloussov et al. |
| 7,084,597 B2 | 8/2006 | Nakai et al. |
| 7,087,200 B2 | 8/2006 | Taboas et al. |
| 7,092,482 B2 | 8/2006 | Besson |
| 7,103,931 B2 | 9/2006 | Somasundaram et al. |
| 7,110,808 B2 | 9/2006 | Adair |
| 7,112,924 B2 | 9/2006 | Hanna |
| 7,116,749 B2 | 10/2006 | Besson |
| 7,120,223 B2 | 10/2006 | Näfstadius |
| 7,120,277 B2 | 10/2006 | Pelagotti et al. |
| 7,123,758 B2 | 10/2006 | Jeung et al. |
| 7,130,372 B2 | 10/2006 | Kusch et al. |
| 7,142,635 B2 | 11/2006 | Kamath et al. |
| 7,154,991 B2 | 12/2006 | Earnst et al. |
| 7,158,692 B2 | 1/2007 | Chalana et al. |
| 7,177,386 B2 | 2/2007 | Mostafavi et al. |
| 7,186,986 B2 | 3/2007 | Hinderer et al. |
| 7,186,991 B2 | 3/2007 | Kato et al. |
| 7,187,752 B2 | 3/2007 | Kotler et al. |
| 7,189,205 B2 | 3/2007 | McMorrow et al. |
| 7,203,272 B2 | 4/2007 | Chen |
| 7,206,377 B2 | 4/2007 | Svatos |
| 7,208,889 B2 | 4/2007 | Zavadtsev et al. |
| 7,209,547 B2 | 4/2007 | Baier et al. |
| 7,221,729 B2 | 5/2007 | Wakai et al. |
| 7,221,733 B1 | 5/2007 | Takai et al. |
| 7,233,688 B2 | 6/2007 | Ritt et al. |
| 7,252,307 B2 | 8/2007 | Kanbe et al. |
| 7,252,434 B2 | 8/2007 | Jaradat |
| 7,257,196 B2 | 8/2007 | Brown et al. |
| 7,259,762 B2 | 8/2007 | Tanacs et al. |
| 7,265,356 B2 | 9/2007 | Pelizzari et al. |
| 7,280,630 B2 | 10/2007 | Chen |
| 7,283,610 B2 | 10/2007 | Low et al. |
| 7,289,599 B2 | 10/2007 | Seppi et al. |
| 7,295,648 B2 | 11/2007 | Brown |
| 7,302,033 B2 | 11/2007 | Carrano et al. |

(56) References Cited

U.S. PATENT DOCUMENTS

| | | | |
|---|---|---|---|
| 7,302,038 B2 | 11/2007 | Mackie et al. | |
| 7,322,929 B2 | 1/2008 | Lovoi | |
| 7,324,842 B2 | 1/2008 | Dale et al. | |
| 7,327,902 B2 | 2/2008 | Ritt et al. | |
| 7,333,588 B2 | 2/2008 | Mistretta et al. | |
| 7,346,381 B2 | 3/2008 | Okerlund et al. | |
| 7,349,730 B2 | 3/2008 | Ein-Gal | |
| 7,362,848 B2 | 4/2008 | Saracen et al. | |
| 7,367,273 B2 | 5/2008 | Shinoda | |
| 7,367,955 B2 | 5/2008 | Zhang et al. | |
| 7,369,645 B2 | 5/2008 | Lane | |
| 7,382,858 B2 | 6/2008 | Gohno | |
| 7,382,907 B2 | 6/2008 | Luo et al. | |
| 7,391,026 B2 | 6/2008 | Trinkaus et al. | |
| 7,391,849 B2 | 6/2008 | Smith | |
| 7,400,755 B2 | 7/2008 | West et al. | |
| 7,412,029 B2 | 8/2008 | Myles | |
| 7,413,873 B2 | 8/2008 | Waterman et al. | |
| 7,437,785 B2 | 10/2008 | Farooqui | |
| 7,438,685 B2 | 10/2008 | Burdette et al. | |
| 7,444,011 B2 | 10/2008 | Pan et al. | |
| 7,450,687 B2 | 11/2008 | Yeo et al. | |
| 7,469,035 B2 | 12/2008 | Keall et al. | |
| 7,471,003 B2 | 12/2008 | Kobayashi et al. | |
| 7,477,721 B2 | 1/2009 | Chappo et al. | |
| 7,492,858 B2 | 2/2009 | Partain et al. | |
| 7,496,173 B2 | 2/2009 | Goldman et al. | |
| 7,505,559 B2 | 3/2009 | Kuduvalli | |
| 7,508,098 B2 * | 3/2009 | Lee | H02K 41/0354 310/12.06 |
| 7,508,967 B2 | 3/2009 | Harari et al. | |
| 7,513,861 B2 | 4/2009 | Klein et al. | |
| 7,536,041 B2 | 5/2009 | Pekar et al. | |
| 7,536,219 B2 | 5/2009 | Mitschke | |
| 7,551,717 B2 | 6/2009 | Tomé et al. | |
| 7,552,490 B2 | 6/2009 | Saracen et al. | |
| 7,567,694 B2 | 7/2009 | Lu et al. | |
| 7,574,251 B2 | 8/2009 | Lu et al. | |
| 7,590,218 B2 | 9/2009 | Scherch et al. | |
| 7,590,440 B2 | 9/2009 | Lau et al. | |
| 7,607,183 B2 | 10/2009 | Somasundaram et al. | |
| 7,609,809 B2 | 10/2009 | Kapatoes et al. | |
| 7,611,452 B2 | 11/2009 | Allison et al. | |
| 7,613,501 B2 | 11/2009 | Scherch | |
| 7,616,729 B2 | 11/2009 | Vengrinovich et al. | |
| 7,620,144 B2 | 11/2009 | Bodduluri | |
| 7,620,227 B2 | 11/2009 | Gering et al. | |
| 7,621,007 B2 | 11/2009 | Somasundaram | |
| 7,623,709 B2 | 11/2009 | Gering | |
| 7,629,599 B2 | 12/2009 | Hashimoto | |
| 7,639,851 B2 | 12/2009 | Ritt et al. | |
| 7,639,853 B2 | 12/2009 | Olivera et al. | |
| 7,639,854 B2 | 12/2009 | Schnarr et al. | |
| 7,640,607 B2 | 1/2010 | Guertin et al. | |
| 7,643,661 B2 | 1/2010 | Ruchala et al. | |
| 7,645,276 B2 | 1/2010 | Pankratov et al. | |
| 7,654,382 B2 | 2/2010 | Farooqui | |
| 7,693,257 B2 | 4/2010 | Allison | |
| 7,693,260 B2 | 4/2010 | Gertner et al. | |
| 7,708,682 B2 | 5/2010 | Pekar et al. | |
| 7,711,405 B2 | 5/2010 | Khamene et al. | |
| 7,773,788 B2 | 8/2010 | Lu et al. | |
| 7,778,691 B2 | 8/2010 | Zhang et al. | |
| 7,784,127 B2 | 8/2010 | Kuro et al. | |
| 7,792,239 B2 | 9/2010 | Nambu et al. | |
| 7,792,348 B2 | 9/2010 | Russakoff | |
| 7,801,269 B2 | 9/2010 | Cravens et al. | |
| 7,801,349 B2 | 9/2010 | Wang et al. | |
| 7,817,836 B2 | 10/2010 | Chao et al. | |
| 7,826,593 B2 | 11/2010 | Svensson et al. | |
| 7,831,289 B2 | 11/2010 | Riker et al. | |
| 7,835,502 B2 | 11/2010 | Spence et al. | |
| 7,839,972 B2 | 11/2010 | Ruchala et al. | |
| 7,853,308 B2 | 12/2010 | Sauer et al. | |
| 7,876,938 B2 | 1/2011 | Huang et al. | |
| 7,881,431 B2 | 2/2011 | Aoi et al. | |
| 7,881,772 B2 | 2/2011 | Ghelmansarai | |
| 7,907,987 B2 | 3/2011 | Dempsey | |
| 7,912,736 B2 | 3/2011 | Wyatt | |
| 7,940,891 B2 | 5/2011 | Star-Lack et al. | |
| 7,945,021 B2 | 5/2011 | Shapiro et al. | |
| 7,945,022 B2 | 5/2011 | Nelms et al. | |
| 7,957,507 B2 * | 6/2011 | Cadman | A61N 5/1042 378/153 |
| 7,974,681 B2 | 7/2011 | Wallace et al. | |
| 7,983,380 B2 | 7/2011 | Guertin et al. | |
| 8,073,104 B2 | 12/2011 | Yan et al. | |
| 8,085,899 B2 | 12/2011 | Nord et al. | |
| 8,094,785 B2 * | 1/2012 | Heid | G21K 1/04 378/149 |
| 8,122,542 B2 | 2/2012 | Reitz et al. | |
| 8,125,813 B2 | 2/2012 | Nizin et al. | |
| 8,140,144 B2 | 3/2012 | Dale et al. | |
| 8,175,350 B2 | 5/2012 | Suri et al. | |
| 8,175,892 B2 | 5/2012 | Kapoor et al. | |
| 8,229,068 B2 | 7/2012 | Lu et al. | |
| 8,232,535 B2 | 7/2012 | Olivera et al. | |
| 8,306,184 B2 | 11/2012 | Chang et al. | |
| 8,331,532 B2 | 12/2012 | Nord et al. | |
| 8,406,520 B2 | 3/2013 | Henkel | |
| 8,406,844 B2 | 3/2013 | Ruchala et al. | |
| 8,509,383 B2 | 8/2013 | Lu et al. | |
| 8,773,227 B2 * | 7/2014 | Krechting | B82Y 10/00 29/606 |
| 2002/0065682 A1 | 5/2002 | Goldenberg | |
| 2002/0193685 A1 | 12/2002 | Mate et al. | |
| 2003/0072411 A1 | 4/2003 | Welsh | |
| 2003/0083562 A1 | 5/2003 | Bani-Hashemi et al. | |
| 2003/0086527 A1 | 5/2003 | Speiser et al. | |
| 2003/0088441 A1 | 5/2003 | McNerney | |
| 2003/0105650 A1 | 6/2003 | Lombardo et al. | |
| 2003/0177039 A1 | 9/2003 | Nicholas et al. | |
| 2003/0212325 A1 | 11/2003 | Cotrutz et al. | |
| 2004/0010418 A1 | 1/2004 | Buonocore et al. | |
| 2004/0032169 A1 * | 2/2004 | Widdowson | G03F 7/70758 310/12.32 |
| 2004/0062354 A1 * | 4/2004 | Kato | A61N 5/1042 378/152 |
| 2004/0068182 A1 | 4/2004 | Misra | |
| 2004/0116804 A1 | 6/2004 | Mostafavi | |
| 2004/0138555 A1 | 7/2004 | Krag et al. | |
| 2004/0175034 A1 | 9/2004 | Wiemker et al. | |
| 2004/0254448 A1 | 12/2004 | Amies et al. | |
| 2005/0031181 A1 | 2/2005 | Bi et al. | |
| 2005/0059879 A1 | 3/2005 | Sutherland et al. | |
| 2005/0063516 A1 * | 3/2005 | Kato | A61N 5/1042 378/152 |
| 2005/0080332 A1 | 4/2005 | Shiu et al. | |
| 2005/0088133 A1 * | 4/2005 | Ebihara | G03F 7/20 318/649 |
| 2005/0096515 A1 | 5/2005 | Geng | |
| 2005/0143965 A1 | 6/2005 | Failla et al. | |
| 2005/0171396 A1 | 8/2005 | Pankratov et al. | |
| 2005/0200830 A1 * | 9/2005 | Carter | G03F 7/70066 355/75 |
| 2005/0251029 A1 | 11/2005 | Khamene et al. | |
| 2006/0074292 A1 | 4/2006 | Thomson et al. | |
| 2006/0078086 A1 | 4/2006 | Riley et al. | |
| 2006/0080057 A1 | 4/2006 | Ritt | |
| 2006/0100738 A1 | 5/2006 | Alsafadi et al. | |
| 2006/0133568 A1 | 6/2006 | Moore | |
| 2006/0138339 A1 | 6/2006 | Fang et al. | |
| 2006/0153330 A1 | 7/2006 | Wong et al. | |
| 2007/0014452 A1 | 1/2007 | Suresh et al. | |
| 2007/0032795 A1 | 2/2007 | Schloesser et al. | |
| 2007/0041496 A1 | 2/2007 | Olivera et al. | |
| 2007/0041498 A1 | 2/2007 | Olivera et al. | |
| 2007/0041500 A1 | 2/2007 | Olivera et al. | |
| 2007/0057579 A1 * | 3/2007 | Miyamoto | H02K 41/03 310/12.01 |
| 2007/0076846 A1 | 4/2007 | Ruchala et al. | |
| 2007/0088573 A1 | 4/2007 | Ruchala et al. | |
| 2007/0104316 A1 | 5/2007 | Ruchala et al. | |
| 2007/0156453 A1 | 7/2007 | Frielinghaus et al. | |

(56) References Cited

U.S. PATENT DOCUMENTS

| | | | |
|---|---|---|---|
| 2007/0176126 A1* | 8/2007 | Hashimoto | G21K 1/04 250/495.1 |
| 2007/0195922 A1 | 8/2007 | Mackie et al. | |
| 2007/0197908 A1 | 8/2007 | Ruchala et al. | |
| 2007/0211857 A1 | 9/2007 | Urano et al. | |
| 2007/0238957 A1 | 10/2007 | Yared | |
| 2008/0008291 A1 | 1/2008 | Alakuijala et al. | |
| 2008/0031406 A1 | 2/2008 | Yan et al. | |
| 2008/0043910 A1 | 2/2008 | Thomas | |
| 2008/0048505 A1* | 2/2008 | Moriyama | H02K 41/03 310/12.22 |
| 2008/0064953 A1 | 3/2008 | Falco et al. | |
| 2008/0193006 A1 | 8/2008 | Udupa et al. | |
| 2008/0205719 A1 | 8/2008 | Pekar et al. | |
| 2008/0279328 A1 | 11/2008 | Zeitler et al. | |
| 2009/0041200 A1* | 2/2009 | Lu | A61N 5/1042 378/152 |
| 2009/0070935 A1 | 3/2009 | Brunker et al. | |
| 2009/0080619 A1* | 3/2009 | Hasegawa | G21K 1/046 378/151 |
| 2009/0110145 A1 | 4/2009 | Lu et al. | |
| 2009/0129641 A1 | 5/2009 | Zhou | |
| 2009/0159677 A1 | 6/2009 | Yakimov et al. | |
| 2009/0187422 A1 | 7/2009 | Kaus et al. | |
| 2009/0226060 A1 | 9/2009 | Gering et al. | |
| 2009/0252291 A1 | 10/2009 | Lu et al. | |
| 2009/0262901 A1* | 10/2009 | Broad | A61N 5/1042 378/152 |
| 2009/0268491 A1 | 10/2009 | Wilson | |
| 2010/0053208 A1 | 3/2010 | Menningen et al. | |
| 2010/0054413 A1 | 3/2010 | Sobering et al. | |
| 2010/0060393 A1* | 3/2010 | Joo | H01H 33/38 335/180 |
| 2010/0183121 A1 | 7/2010 | Riker et al. | |
| 2010/0189220 A1* | 7/2010 | Flynn | A61N 5/103 378/65 |
| 2010/0228116 A1 | 9/2010 | Lu et al. | |
| 2010/0278310 A1* | 11/2010 | Dehler | A61N 5/1042 378/150 |
| 2010/0302525 A1* | 12/2010 | Zimmerman | G03F 7/70133 355/71 |
| 2010/0312104 A1 | 12/2010 | Ruchala et al. | |
| 2010/0319128 A1 | 12/2010 | Kuro et al. | |
| 2011/0019889 A1 | 1/2011 | Gering et al. | |
| 2011/0057753 A1* | 3/2011 | Irwin | H01F 7/088 335/257 |
| 2011/0107515 A1 | 5/2011 | Brunker et al. | |
| 2011/0112351 A1 | 5/2011 | Fordyce, II et al. | |
| 2011/0122997 A1 | 5/2011 | Lu et al. | |
| 2011/0201920 A1* | 8/2011 | Allen | A61N 5/1042 600/411 |
| 2012/0175973 A1* | 7/2012 | Moriyama | H02K 41/03 310/12.24 |
| 2012/0215049 A1* | 8/2012 | Otani | A61N 5/1045 600/1 |
| 2012/0215095 A1* | 8/2012 | Av-Shalom | A61B 6/06 600/424 |
| 2012/0305766 A1* | 12/2012 | Tanaka | H02K 41/031 250/310 |
| 2013/0216026 A1* | 8/2013 | Nord | A61N 5/1037 378/65 |
| 2013/0272504 A1* | 10/2013 | Deutsch | G21K 1/04 378/150 |

FOREIGN PATENT DOCUMENTS

| | | |
|---|---|---|
| DE | 10221634 | 12/2003 |
| EP | 0259989 | 3/1988 |
| EP | 1419801 | 5/2004 |
| JP | 63209667 | 8/1988 |
| JP | 1209077 | 8/1989 |
| JP | 5154209 | 6/1993 |
| JP | 6007464 | 1/1994 |
| JP | 7507479 | 8/1995 |
| JP | 9099110 | 4/1997 |
| JP | 9271520 | 10/1997 |
| JP | 10033698 | 2/1998 |
| JP | 10052421 | 2/1998 |
| JP | 10501151 | 2/1998 |
| JP | 10146395 | 6/1998 |
| JP | 1164530 | 3/1999 |
| JP | 11169471 | 6/1999 |
| JP | 11244401 | 9/1999 |
| JP | 2000116643 | 4/2000 |
| JP | 2001029489 | 2/2001 |
| JP | 2001034676 | 2/2001 |
| JP | 2001505071 | 4/2001 |
| JP | 2001161839 | 6/2001 |
| JP | 2001259060 | 9/2001 |
| JP | 2001340474 | 12/2001 |
| JP | 2002157362 | 5/2002 |
| JP | 2002514481 | 5/2002 |
| JP | 2002186678 | 7/2002 |
| JP | 2002210029 | 7/2002 |
| JP | 2002522128 | 7/2002 |
| JP | 2002522129 | 7/2002 |
| JP | 2002272863 | 9/2002 |
| JP | 2002537036 | 11/2002 |
| JP | 2002345802 | 12/2002 |
| JP | 2002355321 | 12/2002 |
| JP | 2003196385 | 7/2003 |
| JP | 2003523220 | 8/2003 |
| JP | 2003250917 | 9/2003 |
| JP | 2004166975 | 6/2004 |
| JP | 11313900 | 10/2004 |
| JP | 2004275636 | 10/2004 |
| JP | 2004305641 | 11/2004 |
| JP | 2004321502 | 11/2004 |
| JP | 2005024475 | 1/2005 |
| JP | 2005160804 | 6/2005 |
| JP | 2005518908 | 6/2005 |
| JP | 2007509644 | 4/2007 |
| JP | 2007516743 | 6/2007 |
| JP | 2007526036 | 9/2007 |
| KR | 20050073862 | 7/2005 |
| RU | 762754 | 2/1999 |
| RU | 953966 | 3/1999 |
| RU | 2166241 | 4/2001 |
| RU | 2168291 | 5/2001 |
| RU | 2191491 | 5/2001 |
| RU | 2249927 | 10/2002 |
| TW | 300853 | 3/1997 |
| TW | I223199 | 11/2004 |
| TW | 261523 | 9/2006 |
| WO | 9014129 | 11/1990 |
| WO | 9202277 | 2/1992 |
| WO | 9423439 | 10/1994 |
| WO | 9802091 | 1/1998 |
| WO | 0007037 | 2/2000 |
| WO | 0007669 | 2/2000 |
| WO | 0054689 | 9/2000 |
| WO | 0224277 | 3/2002 |
| WO | 03032838 | 4/2003 |
| WO | 03047694 | 6/2003 |
| WO | 03076003 | 9/2003 |
| WO | 03092789 | 11/2003 |
| WO | 03099380 | 12/2003 |
| WO | 2004057515 | 7/2004 |
| WO | 2004064641 | 8/2004 |
| WO | 2004066211 | 8/2004 |
| WO | 2004080522 | 9/2004 |
| WO | 2004098712 | 11/2004 |
| WO | 2004105574 | 12/2004 |
| WO | 2005031629 | 4/2005 |
| WO | 2005035061 | 4/2005 |
| WO | 2005036124 | 4/2005 |
| WO | 2005041835 | 5/2005 |
| WO | 2005057463 | 6/2005 |
| WO | 2005062790 | 7/2005 |
| WO | 2007014026 | 2/2007 |
| WO | 2007014094 | 2/2007 |
| WO | 2007079207 | 7/2007 |

(56) References Cited

FOREIGN PATENT DOCUMENTS

| WO | 2007079854 | 7/2007 |
|----|------------|--------|
| WO | 2007127970 | 11/2007 |
| WO | 2007133932 | 11/2007 |

OTHER PUBLICATIONS

Purdy, James, "3D Treatment Planning and Intensity-Modulated Radiation Therapy," Oncology, vol. 13, No. 10, suppl. 5 (Oct. 1999).
Van Den Elsen, P.A. et al., "Automatic Registration of CT and MR Brain Images Using Correlation of Geometrical Features," IEEE Transactions on Medical Imaging, vol. 14, Jun. 1995.
Bert, Christoph, et al., "4D Treatment Planning for Scanned Ion Beams", BioMed Central, Radiation Oncology, 2:24, available online at: <http://www.ro-journal.com/content/2/1/24>, Jul. 3, 2007.
Bertalmio, Marcelo, et al., "Morphing Active Contours", IEEE Transactions on Pattern Analysis and Machine Intelligence, vol. 22, No. 7, pp. 733-737, Jul. 2000.
Birkner, M. et al., "Image guided adaptive IMRT of the prostate based on a probabilistic patient geometry," Radiotherapy and Oncology, vol. 64, Supplement 1, 21st Annual ESTRO Meeting, Sep. 21, 2002, p. S282, ISSN 0167-8140.
Yu, Cedric X., et al., "A Method for Implementing Dynamic Photon Beam Intensity Modulation using Independent Jaws and a Multileaf Collimator," Phys. Med. Biol. 40. 1995: 769-787.
Yan, Di, "On-line Strategy of Daily Dose Prescription in Adaptive Radiotherapy," Proceedings of the 22nd Annual EMBS International Conference, Jul. 23-28, 2000, Chicago, IL, pp. 2145-2148.
Yang, Deshan, et al., "4D-CT motion estimation using deformable image registration and 5D respiratory motion modeling," Medical Physics, vol. 35, No. 10, Sep. 19, 2008.
Ott, Kenneth, "Gamma Knife Radiosurgery for Brain Tumors," http://web.archive.org/web/20030305053551/http://www.virtualtrials.com/gamma.cfm; Archived Mar. 5, 2003; Retrieved Jul. 21, 2010.
Lee, Jason et al., "Intensity Modulated Radiation Therapy; An Introduction for Patients and Clinicians," www.oncolink.com/templates/treatment/article.cfm?c=45&s=33&id=182; Jun. 16, 2001.
Kudo et al., "Helical-scan Computed Tomography Using Cone-Beam Projections," IEEE Conference 1991, ISBN: 0-7803-0513, vol. 3, pp. 1958-1962.
Law, Maria Y.Y., "A Model of DICOM-based Electronic Patient Record in Radiation Therapy," Computerized Medical Imaging and Graphics, vol. 29, pp. 125-136, 2005.
Lof, J. et al., "An Adaptive Control Algorithm for Optimization of Intensity Modulated Radiotherapy Considering Uncertainties in Beam Profiles, Patient Set-Up and Internal Organ Motion", Physics in Medicine and Biology 43, 1605-1628, Printed in the UK, 1998.
Lu, W., et al., "Automatic Re-Contouring Regions of Interest Based on Deformable Registration and Surface Reconstruction," AAPM 2004, (abstract: Medical Physics 31, 1845-6).
Lu, W., et al., "Automatic Re-Contouring in 4D Radiotherapy", Physical Medical Biology, Mar. 7, 2006, 51 (5):1077-99.
Lu, W., et al., 2004 "Automatic Re-Contouring for 4-D Planning and Adaptive Radiotherapy," The 90th RSNA Meeting, Chicago, Illinois, (abstract:Radiology 227 p. 543).
Mackie, T. Rockwell et al., "Tomotherapy" Seminars in Radiation Oncology, vol. 9, No. 1, Jan. 1, 1999, pp. 108-117, XP002603992.
Miller, Karen, "The Phantom Torso", RT Image, vol. 14 No. 25, Jun. 18, 2001.
Wells III, William et al., "Multi-Modal Volume Registration by Maximization of Mutual Information," Medical Image Analysis, Oxford University Press (1996).
Maes, F. et al., "Multimodality Image Registration By Maximization of Mutual Information," IEEE Transactions on Medical Imaging, vol. 16, No. 2, Apr. 1997.

Olivera, G. et al. "Dynamic Tangents and Topotherapy: New Delivery Capabilities for Helical Tomotherapy" Medical Physics [Online],vol. 32, No. 6, Jun. 1, 2005, pp. 2034-2034, XP002603991.
Fitchard, E.E., et al., "Registration of Tomotherapy Patients Using CT Projection Files," www.madrad.radiology.wisc.edu/tomo/registration/reg_iccr2/reg_iccr2.html.
Rogus, Ronald, D., "Accuracy of a Photogrammetry-Based Patient Positioning and Monitoring System for Radiation Therapy", Medical Physics Online, available online at: <http://scitation.aip.orgivsearch/servlet/VerityServlet?KEY=FREESR&smode=strresults&sort=chron&maxdisp=25&threshold=0&possible1=Ronald+Rogus&possible1zone=article&OUTLOG=NO&viewabs=MPHYA6&key=DISPLAY&docID=2&page=1&chapter=0>, abstract view, vol. 26, issue 5, 2 pages, May 1999.
Ruchala, Kenneth, et al., "Adaptive IMRT with Tomotherapy", RT Image, vol. 14, No. 25, pp. 14-18, Jun. 18, 2001.
Rueckert, D.et al., "Nonrigid Registration Using Free-Form Deformations: Application to Breast MR Images", IEEE Transactions on Medical Imaging, vol. 18, No. 8, pp. 712-721, Aug. 1999.
Selker, Robert G., "Intensity Modulated Radiation Therapy (IMRT) Technology, The Peacock System, At The Western Pennsylvania Hospital," Archived Oct. 9, 1999, http://web.archive.org/web/19991009052520/http://virtualtrials.com/peacock1.cfm.
Song, Yulin, et al., "From Intensity Modulated Radiation Therapy to 4D Radiation Therapy—An Advance in Targeting Mobile Lung Tumors", Proceedings of the 29th Annual International Conference of the IEEE EMBS Cite Internationale, Lyon, France, Aug. 23-26, pp. 226-229, 2007.
Michalski, Jeff M. et al., Three-Dimensional Conformal Radiation Therapy (3DCRT) for Prostate Cancer,: The Prostate Cancer InfoLink, Jul. 6, 1996.
Kikinis R. et al., "High Performance Computing (HPC) in Medical Image Analysis (MIA) at the Surgical Planning Laboratory (SPL)," http://splweb.bwh.havard.edu:8000/pages/papers/kikinis/hps/hpcfinal.html; Sep. 22, 1998.
Yezzi, et al., "A Variational Framework for Joint Segmentation and Registration", Mathematical Method in Biomedical Image Analysis, 8 pages, 2001.
Young, Yuan-Nan, et al., "Registration-Based Morphing of Active Contours for Segmentation of CT Scans", Mathematical Biosciences and Engineering, vol. 2, No. 1, pp. 79-96, Jan. 2005.
Gering, D. et al., "An Automatic Contouring Method that Combines Rule-Based, Atlas-Based, and Mesh-Based Approaches," Medical Physics—2008 AAPM Meeting Program, vol. 35, No. 6, p. 2662, Jun. 2008.
Pitiot, Alain et al., "Expert Knowledge-Guided Segmentation System for Brain MRI," NeuroImage, vol. 23, pp. S85-S96, Jan. 1, 2004.
Dam, E.B. et al., "Automatic Morphometric Cartilage Quantification in the Medial Tibial Plateau from MRI for Osteoarthritis Grading," OsteoArthritis and Cartilage, vol. 15, No. 7, pp. 808-818, Jun. 13, 2007.
Ayman El-Baz et al., "MGRF Controlled Stochastic Deformable Model," Image Analysis; Lecture Notes in Computer Science, pp. 1138-1147, Jun. 28, 2005.
Gering, D. et al., "Recognizing Deviations from Normalcy for Brain Tumor Segmentation," Medical Image Computing and Computer-Assisted Intervention, vol. 2488, pp. 388-395, Sep. 25, 2002.
Gering, David T. et al. "Image Deformation Based on a Marionette Model" Medical Physics, vol. 37, No. 6, Jun. 1, 2010, p. 3127.
Gu et al. GPU-based ultra-fast dose calculation using a finite size pencil beam model. Physics in Medicine and Biology. Oct. 1, 2009, vol. 54, No. 20, pp. 6287-6297.
Mackie, T. Rockwell et al., "Tomotherapy: Rethinking the Processes of Radiotherapy," XIIth ICCR, May 27-30, 1997.
Fang, Guang Y. et al., "Software system for the UW/GE tomotherapy prototype," Xiith ICCR, May 27-30, 1997.

(56) References Cited

OTHER PUBLICATIONS

Rietzel, Eike et al., "Four-Dimensional Image-Based Treatment Planning: Target Volume Segmentation and Dose Calculation in the Presence of Respiratory Motion," International Journal of Radiation: Oncology Biology Physics, vol. 61, No. 5, pp. 1535-1550 (Apr. 1, 2005).

Straka, M. et al., "Bone Segmentation in CT-Angiography Data Using a Probabilistic Atlas," 2003.

Dayton, L. et al., "The Photoshop 5/5.S Wow! Book," Chapter 2: Selections, Masks, Layers, and Channels, pp. 65-68, 71-75, 77 (2000).

Welsh, J.S. et al., "Helical tomotherapy: an innovative technology and approach to radiation therapy," Technol. Cancer Res. Treat., Aug. 2002.

\* cited by examiner

Leaf Open

Leaf 70% open

Leaf Closed

Leaf 20% open

ELECTROMAGNETICALLY ACTUATED MULTI-LEAF COLLIMATOR

CROSS-REFERENCE TO RELATED APPLICATIONS

This application is a non-provisional of and claims priority to U.S. Provisional Application No. 61/769,549, filed on Feb. 26, 2013. The contents of Application No. 61/769,549 are incorporated herein by reference. All publications and patent applications mentioned in this specification are herein incorporated by reference to the same extent as if each individual publication or patent application was specifically and individually indicated to be incorporated by reference.

FIELD OF THE INVENTION

The present invention generally relates to radiation therapy. In various respects, the invention is directed to a highly responsive multileaf collimator, and method of use to provide radiation therapy utilizing beam shaping, intensity modulation and combinations thereof including simultaneous beam shaping and intensity modulation of therapeutic beams.

BACKGROUND OF THE INVENTION

Intensity modulated radiotherapy (commonly referred to as IMRT) is a generic term for a number of radiotherapy techniques that, essentially, vary the beam intensity that is directed at the patient. That variation can be spatial, temporal, or both.

In radiation therapy the terms dose, fluence and intensity are sometimes used interchangeably and confusingly. For the purposes of this description and this application these terms are used as follows. Fluence is the number of photons or x-rays that crosses a unit of area perpendicular to a radiation beam. Fluence rate is the fluence per unit time. Intensity is the energy that crosses a unit area per unit time. Fluence and intensity are independent of what occurs in a patient, and more specifically are not dose. Dose is the amount of energy absorbed by tissue by virtue of radiation impacting the tissue. Radiation dose is measured in units of gray (Gy), where each Gy corresponds to a fixed amount of energy absorbed in a unit mass of tissue (e.g., 1 joule/kg). Dose is not the same as fluence, but increases/decreases as fluence increases/decreases.

In radiation therapy delivery, the beam aperture is commonly set by a multi-leaf collimator (MLC). One such method of using the MLC is to create one or more patterns that shape the radiation. A single shape that matches a target is commonly referred to as a conformal delivery. For more complicated dose distributions IMRT can be utilized. In IMRT, rather than having the MLC shape the incident radiation to match a certain outline, the MLC is instead used to create an array of beam shapes that create a desired intensity modulation and desired 3D dose distribution.

FIG. 1 illustrates an isometric view of a conventional shaping-MLC 31 (such as those used on Varian radiation therapy systems) passing a beam to a target in a patient. Two banks 33, of opposing leaves, where each leaf 37 may be positioned continuously across the radiation field. The two banks of leaves are positioned so as to collimate the beam 30 in the desired shape. Each leaf 37 typically may travel beyond the midpoint of the collimator in order to provide flexibility when achieving the desired collimation. The configuration illustrates fully open (41), partially open (43) and closed (45) leaf states.

In an example of radiation therapy, each gantry angle has one beam associated with that particular gantry angle, which beam 30 is then collimated into multiple shapes by an MLC. Treatment beam 30 passes through the shaped aperture 47 formed by the leaves 37. The resulting collimated beam continues onto a target 14 within the patient 38. FIG. 1 also illustrates how the treatment beam may be visualized or conceptualized as many different beamlets 49. Leaves 37 of conventional shaping-MLC 31 are moved into various positions to achieve desired shapes or apertures for specified periods of time to achieve fluence map 51 for that particular beam. Modulation of the conceptualized beamlets occurs by sequentially and monotonically moving the leaves into desired positions to achieve desired shapes or appertures such that the time a conceptualized beamlet is exposed controls the intensity of that beamlet. Monotonic, as used in this application and related to radiation therapy, means an ordered sequence of apertures where the sequence is dictated by a continuum from one aperture to a subsequent aperture or where individual leaves increment in one direction during a given series of apertures. In other words, a sequence of apertures would be dictated by mechanical limitations of the MLC, not so much by what may achieve the more optimal treatment delivery; a sequence would go from aperture 1, then 2 then 3 and so on, and not from 1 to 3 then to 5 then back to 2. Rather than use a single conformal shape, the MLC delivers a sequence of shapes. The net amount of radiation received at any given gantry position is based upon the extent to which the different shapes permit the passage or blockage of radiation. As seen in FIG. 1, the shape of MLC 31 shown does not directly correspond to the beamlet intensities of the fluence map 51. As will be appreciated, the depicted fluence map shows the accumulation of intensities for multiple shapes the MLC has taken for that particular gantry angle. A common limitation of the conventional shaping MLC is that the leaves defining the shapes move relatively slowly. Using large numbers of shapes, or shapes that require large leaf motions, can result in longer patient treatments. Likewise, the speed of the leaves can limit the ability of conventional shaping-MLC's to deliver time-sensitive treatments, such as utilizing synchronized motion of delivery components (e.g., gantry, couch, x-ray energy etc.).

A conventional binary MLC 61 is shown in FIG. 2. The binary MLC 61 has a plurality of leaves 63 arranged in two banks 65, 67. Each bank of leaves is used to form a treatment slice by positioning the leaf in a closed position or open position with respect to the beam. As shown in FIG. 2, the leaves may work in concert to be both open (A), both closed (B) or where only one leaf is open/closed (C).

Binary MLCs are used in TomoTherapy's Hi-Art® radiation therapy system and the North American Scientific treatment system. In the conventional binary-MLC treatment system the patient is moved past the rotating radiation source to deliver a helical treatment to the patient using the dual bank binary collimator. Alternatively, the patient is indexed for treatment of another subsequent two slices by the dual bank binary collimator, as is done by the North American Scientific system. Leaves of the dual bank binary collimator move with sufficient speed such that leaf sequencing or positioning will not be significantly influenced by any previous or future positions (open or closed for a binary collimator) of any individual leaf. Stated another way, leaf speed is sufficient such that the mechanics of the MLC do not unduly influence the determination of leaf position at any given time for the delivery of a radiation therapy treatment or fraction. Thus, and in contrast to the conventional shaping-MLC, each leaf defines a beamlet that does not require conceptualization by the planning software, i.e., the amount of time a leaf is open directly controls the intensity for that beamlet.

For both conventional MLCs (shaping and binary), each beamlet has a fluence and all the fluences combined form a fluence map for the beam. The fluence maps for each gantry angle or for all the beams are combined and optimized into the treatment plan. The example of the conventional shaping MLC has been provided to illustrate the underlying concepts of volumetric intensity modulation using the shaping MLC and that of the binary MLC to illustrate the underlying concepts of direct intensity modulation at discrete gantry angles. More complicated treatment plans and delivery can include gantry motion, couch motion, varying gantry speed, varying MU, etc. in order to provide more sophisticated and theoretically better dose conformation in less time per fraction. It is the treatment plan, via delivery software, that governs the operation of the treatment delivery device. The physical capabilities of the delivery system (gantry, linear accelerator, MLC, couch, etc.) limits or constrains the treatment planning software in the type of plan it can create and optimize for delivery by the delivery system.

Treatment planning systems and software (collectively referred to as planning system) are not the focus of this application, but, and as will be appreciated, are integral for treating a patient with radiation. Radiation therapy treatments are governed by a treatment plan, typically generated by a physician or physicist (alone or collectively a "planner") using the planning system. The planner will typically use a diagnostic 3D image (typically CT, although combinations of any PET, CT, MR maybe used) and define or contour the target structure and any nearby critical structures or organs at risk (OAR). The planner then determines the amounts of radiation for delivery to the target structure and the amount of radiation that will be allowed to the OAR. The treatment planning software, using inverse planning and the physical capabilities of the delivery device will generate a treatment plan. The planner then evaluates the plan to determine if it meets the clinical objectives, and if so will approve the plan for delivery to the patient. Delivery of the plan occurs in multiple treatment sessions or fractions.

Conventional MLCs and the treatment paradigms resulting from them have provided steadily advancing and more sophisticated conformal radiation therapy treatments. However, there remains a need for more advanced shaping and modulation of the therapeutic beams, thereby enabling treatment planning software to develop and enable delivery of even more sophisticated plans. As seen by the above summary of radiation therapy techniques, one key component for delivery of radiation therapy is the collimator. While multi-leaf collimators exist, the speed and control of an individual leaf or group of leaves is insufficient to achieve more advanced simultaneous shaping and modulating beam patterns. What is needed are improved multileaf collimator designs, responsive enough to meet the speed and position control requirements of more advanced radiation treatment plans, thereby enabling new treatment paradigms.

SUMMARY OF THE INVENTION

Embodiments of the present invention provide a multi leaf collimator (MLC). These embodiments have a plurality of leaves having a length of travel. Each leaf has a proximal end, a distal end, a radio opaque distal blocking portion having a length L and width W, a proximal drive portion having a length L' and width W', one or more conductive coils fixed to the proximal drive portion and operatively connected to an electrical current source, where electrical current passing through the conductive coils generates a first magnetic field. The MLC of these embodiments also have a leaf guide with a plurality of channels arranged approximately parallel and adjacent to each other where at least a portion of each of the plurality of leaves is slidingly arranged into each of said channels, and a plurality of stationary magnets positioned adjacent to the proximal drive portion, where each stationary magnet has a second magnetic field configured to operate in conjunction with the first magnetic field from the coils to exert a force on the proximal drive portion. In some embodiments the MLC will have dual opposing banks of leaves, and other embodiments will have the stationary magnets on either side of the drive portion.

Embodiments of the present invention also include methods for collimating a therapeutic radiation beam with a multi leaf collimator (MLC). These embodiments may include determining a desired state for one or more leaves of the MLC, where the one or more leaves are moved using an electromagnetic drive system, if the one or more leaves are not in the desired state, then a magnetic field is modified to result in a force on the one or more leaves causing them to move, and lastly the leaves are stopped at the desired state or position. If the leaves are not in the desired state further embodiments apply a current to electromagnetic coils residing within a driving portion of the leaves to generate a first magnetic field, where the first magnetic field operates in conjunction with a second magnetic field from stationary magnets on either side of the driving portion, which results in a force on said driving portion causing the leaves to move.

In one embodiment, the invention provides a multi leaf collimator (MLC) comprising a plurality of leaves, a leaf guide configured to support the plurality of leaves, and a plurality of stationary magnets. The plurality of leaves have a length of travel, wherein each leaf comprises a blocking portion having a length L and a width W and being radio opaque, a drive portion having a length L' and a width W', the drive portion connected to the blocking portion, and a conductive coil operatively connected to an electrical current source, wherein the conductive coil is fixed to the drive portion along at least a portion of length L', and wherein electrical current passing through the conductive coil generates a first magnetic field. Each of the stationary magnets is positioned adjacent to the drive portion of at least one leaf, wherein each stationary magnet has a second magnetic field configured to operate in conjunction with the first magnetic field to exert a force on the drive portion.

In another embodiment, the invention provides a system for collimating a therapeutic radiation beam. The system comprises a multi leaf collimator (MLC), a leaf guide configured to support the plurality of leaves, a plurality of stationary magnets, and a driver component. The MLC comprises a plurality of leaves having a length of travel, wherein each leaf comprises a blocking portion having a length L and a width W and being radio opaque, a drive portion having a length L' and a width W', the drive portion connected to the blocking portion, and a conductive coil operatively connected to an electrical current source, wherein the coil is fixed to the drive portion along at least a portion of the length L', and wherein electrical current passing through the coil generates a first magnetic field. Each of the stationary magnets is positioned adjacent to the drive portion of at least one leaf, wherein each stationary magnet has a second magnetic field configured to operate in conjunction with the first magnetic field to exert a force on the drive portion. The driver component directs electrical current to the coil, thereby causing movement of the plurality of leaves to desired states.

In a further embodiment, the invention provides a multi leaf collimator (MLC) comprising a plurality of leaves having a length of travel, wherein each leaf comprises a blocking portion having a length L and a width W, wherein the blocking portion is radio opaque; and a drive portion having a length L' and a width W', the drive portion connected to the blocking portion; and wherein at least one of the leaves is capable of moving at a speed of at least 50 cm/s.

In a further embodiment, the invention provides a multi leaf collimator (MLC) comprising a plurality of leaves, a leaf guide configured to support the plurality of leaves, and a plurality of conductive coils. The plurality of leaves have a length of travel, wherein each leaf comprises a blocking portion having a length L and a width W and being radio opaque, a drive portion having a length L' and a width W', the drive portion connected to the blocking portion, and a permanent magnet positioned in the drive portion. At least one coil is positioned between adjacent leaves and connected to an electrical current source to generate a first magnetic field when current passes through the at least one coil that interacts with a second magnetic field generated by the magnet to exert a force on the drive portion.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 23B illustrates a radiation therapy system where the radiation source and collimation device is mounted on a robotic arm.

DETAILED DESCRIPTION

Figure 1:
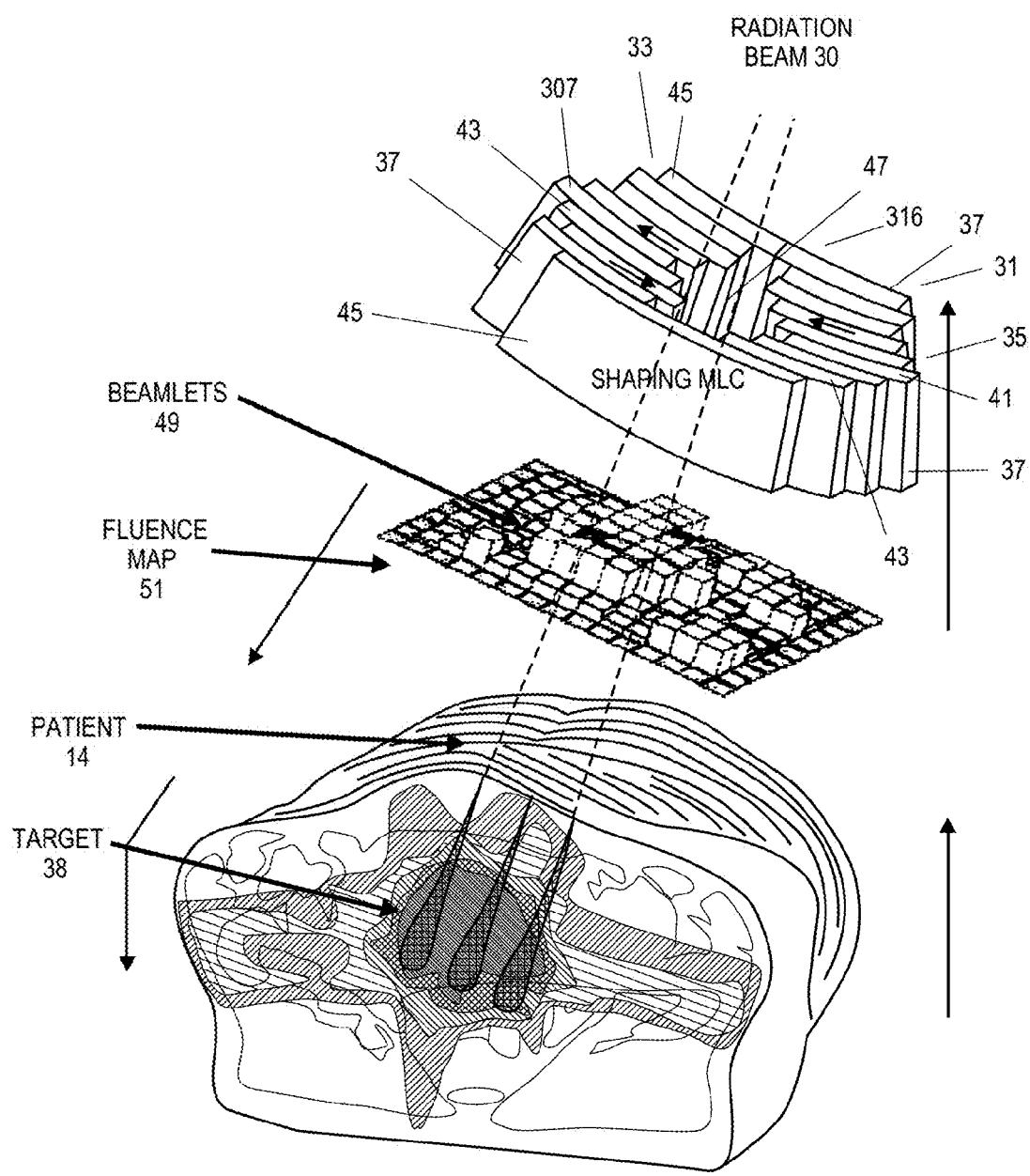
FIG. 1 illustrates a conventional shaping MLC being used to provide a representative dose to a target in a patient.
Figure 2:
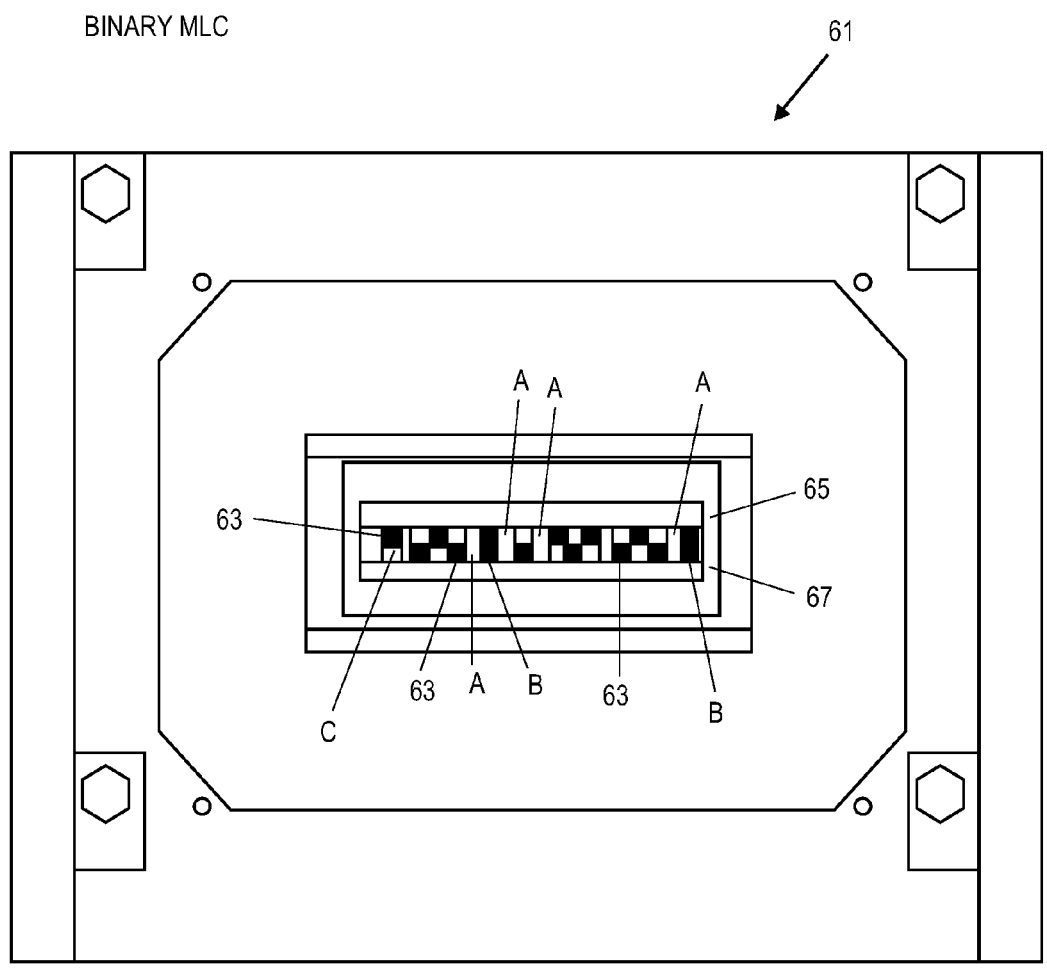
FIG. 2 is a bottom up view of a conventional binary MLC.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 3:
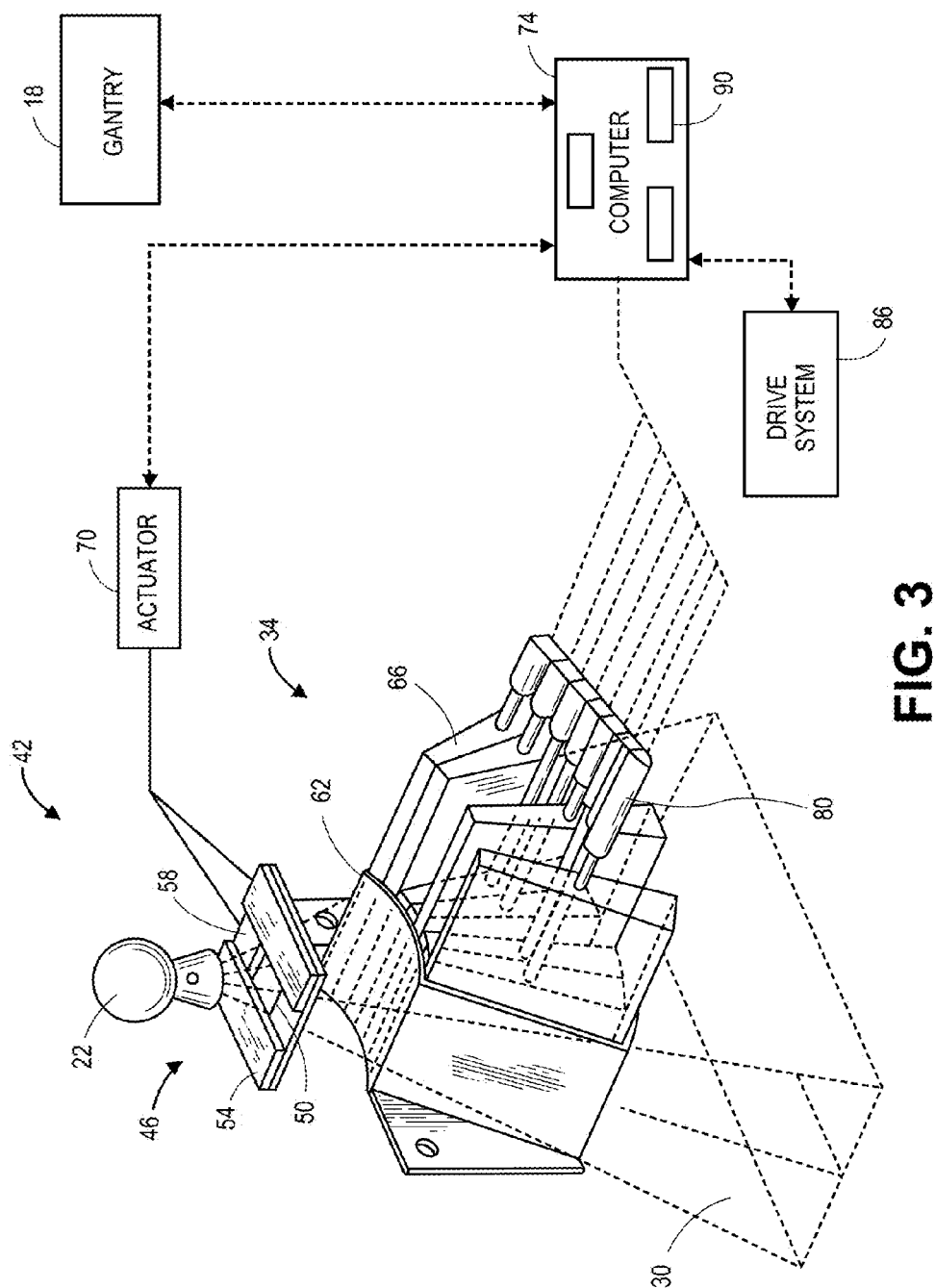
FIG. 3 is a perspective view of a discrete binary multi-leaf collimator that can be used in the radiation therapy treatment system illustrated in FIG. 3.

In one embodiment of the present invention, and illustrated in FIG. 3, a radiation modulation device 34 can comprise an electromagnetically actuated MLC 62, which includes a plurality of leaves 66 operable to move from position to position, to provide intensity modulation. Leaves 66 can move to any position between a minimally and maximally-open position, and with sufficient speed such that leaf sequencing or positioning will not be significantly influenced by any previous or future positions (open or closed for binary collimator) of any individual leaf. Stated another way, leaf speed is sufficient such that the mechanics of the MLC do not unduly influence the determination of leaf position at any given time for the delivery of a radiation therapy treatment or fraction. Each leaf 66 is independently controlled by an actuator (not shown, but more fully described below), such as a motor, or magnetic drive in order that leaves 66 are controllably moved from fully open, fully closed or to any position between open and closed as described in greater detail below. The actuators can be suitably controlled by computer 74 and/or a controller.

Figure 4:
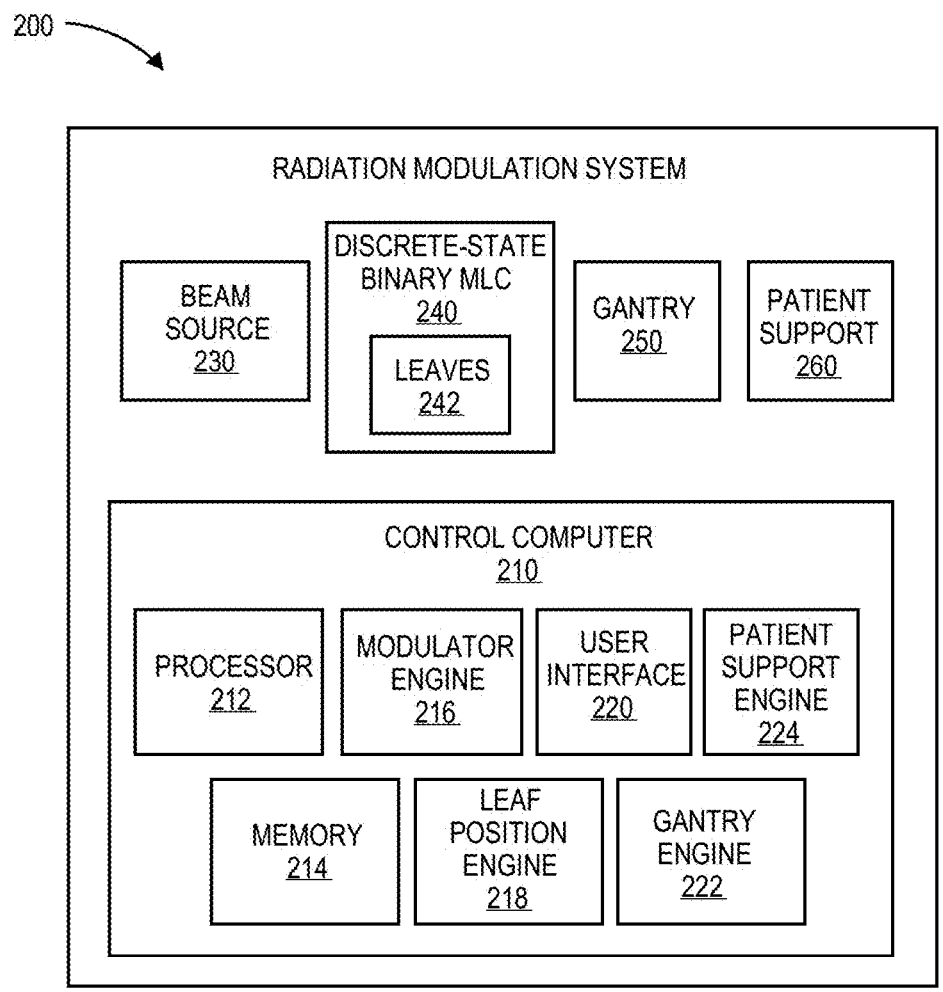
FIG. 4 is a block diagram of an exemplary computer control scheme.

FIG. 4 is a block diagram of an exemplary control computer within a radiation modulation system. In this particular embodiment, the control computer would receive a treatment plan and would control delivery of the plan. As will be appreciated, many different configurations can be used to accomplish this purpose, and this is but one example. Radiation modulation system 200 includes control computer 210, beam source 230, multileaf collimator (MLC) 240, gantry 250, and patient support 260. Control computer 210 includes processor 212, memory 214, modulator engine 216, leaf position engine 218, user interface 220, gantry engine 222, and patient support engine 224. In some embodiments, a control computer may be implemented with several processors, separate computing devices, and otherwise be distributed.

Processor 212 may load and execute programs stored in memory 214. The programs stored on memory 214 may be executed to perform the functionality described herein, including, gantry control, jaw control, patient support control and other functionality involved in administering a treatment plan.

Modulator engine 216 may control all or a portion of the leaf motion and jaw motion, in order to deliver radiation to a patient in accordance with the treatment plan, may process information regarding the position of a leaf and generate a signal to transmit to a driver to move the leaf to a desired position, or control other components in order to ensure a proper delivery of a treatment plan to a patient. To ensure the desired dose is delivered, modulator engine 216 receives gantry position, leaf position and patient support position information from the gantry engine, leaf position engine and patient support engine, respectively. The modulator engine 216 may use the position information and control the required intensity modulation for the necessary dosage for a particular set of treatment parameters (e.g., gantry position and/or speed, leaf position, and patient support position and/or speed), in accordance with the treatment plan. The modulator engine provides control sequences for movement of an individual leaf or group of leaves to form a desired aperture or to modulate a beamlet of a shape in accordance with the treatment plan. In addition or alternatively, one or more jaws may also be opened, closed or repositioned in support of beam shaping, intensity modulation or combinations thereof. In another aspect, the modulator engine provides discrete position information for an individual leaf, a group of leaves, and one or more jaws to maintain, or move independently these components to rapidly create a desired beam shape or collimation, enabling treatments with combined volumetric and direct intensity modulation. The leaf positioning movements and jaw positioning movements may be performed according to desired settings within the treatment plan that correspond to a particular gantry position or speed, patient position or speed or other specific factors for an individual patient's therapy. Modulator engine 216 may be implemented as software stored in memory 214 and executable by processor 212 or a circuit or logic external to processor 212.

Leaf position engine 218 may control and monitor the movement and position of one or more leaves within magnetically actuated MLC 240. Leaf position engine 218 may be implemented as logic, a circuit, or software that is stored in memory 214 and loaded and executed by processor 212.

User interface 220 may provide text, graphical content, and other content to be provided through an output mechanism for a user. In some embodiments, user interface 220 provides an interactive graphical interface that provides a user with the current status of the radiation modulation system, treatment status and progress, and other information. Gantry engine 222 may control and monitor the position of gantry 250. The gantry position may be provided to modulator engine 216, processor 212 and other portions of control computer 210. Gantry engine 222 may be implemented as logic, a circuit, or software that is stored in memory 214 and loaded and executed by processor 212.

Beam source 230 may provide a therapeutic radiation beam used to treat a patient. The beam may be a photon beam generated from a linear accelerator or other particle beam (e.g., proton beam) known in the art to provide treatment to a patient.

Magnetically actuated MLC 240 includes leaves 242 and may be controlled by control computer 210 to adjust leaf position and provide leaf motion. Additional details of leaf position control and actuation are described below. Gantry 250 moves about the patient during treatment. The position of gantry 250 may be controlled and monitored by gantry engine 222 of control computer 210. The position of the patient support 260 (and the patient thereon) may be controlled and monitored by the patient support engine 224.

Magnetically actuated MLCs in accordance with embodiments of the present invention, unlike conventional MLCs of the past (shaping and binary), enable more control for modulating radiation intensity across a beam field for delivering radiation during discrete gantry positions, during gantry rotation/movement, couch motion, target motion or any combination thereof. Embodiments of the present invention permit moving leaves of a collimator along the continuum of positions between open and closed, such as in conventional shaping MLCs and with a sufficient speed such that leaf sequencing or positioning will not be significantly influenced by any previous or future positions (open or closed for binary collimator) of any individual leaf. Stated another way, leaf speed is sufficient such that the mechanics of the MLC do not unduly influence the determination of leaf position at any given time for the delivery of a radiation therapy treatment or fraction. This capability enables the ability to modify or change apertures non-monotonically, thereby enabling new paradigms of treatment heretofore not enabled by conventional MLCs. As described above, conventional radiation therapy machines have used multileaf collimators with relatively slow moving leaves to shape a beam to specific desired shapes, and in this manner create a volumetric intensity modulation.

Figure 5A:
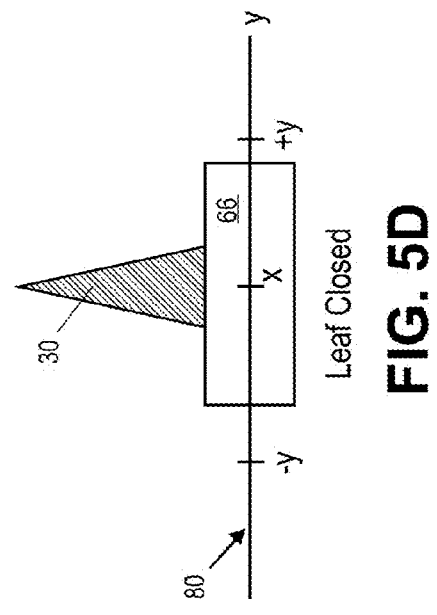
FIGS. 5A-5D illustrate the movement of a representative leaf in open, closed and partially open states as a result of operation as part of a discrete binary multi-leaf collimator.
Figure 5B:
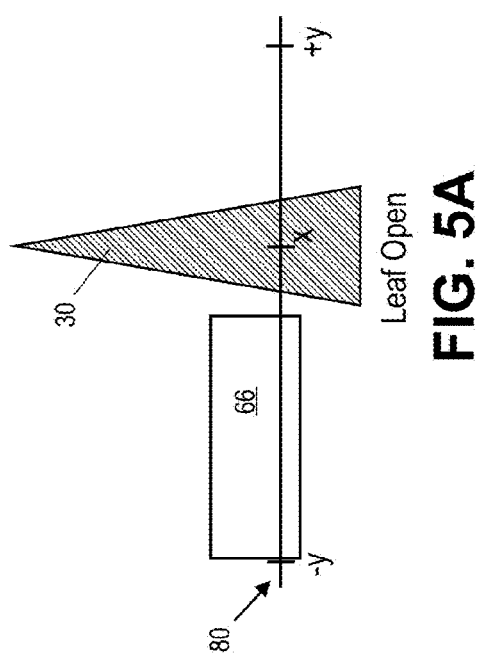
Figure 5D:
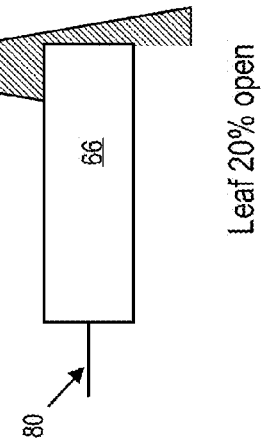
Figure 5C:
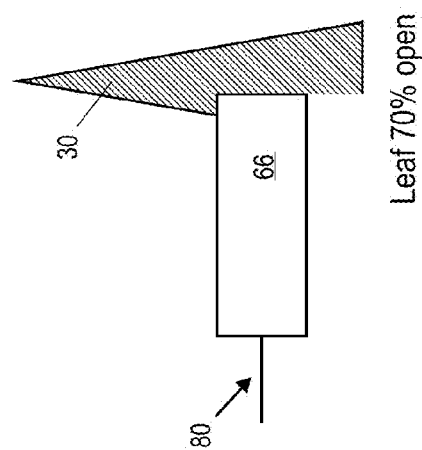

FIGS. 5A-5D show a leaf in a magnetically actuated collimator, in accordance with embodiments of the present invention, where the leaf is in a fully open (state 1, FIG. 5A) or fully closed position (state 4, FIG. 5D). FIGS. 5B and 5C show a leaf in a magnetically actuated collimator, in accordance with embodiments of the present invention, where the leaf in state 3 (FIG. 5C) permitting 20% radiation transmission (i.e., 20% open position) and the leaf in state 2 (FIG. 5B) permitting 70% transmission or is in a 70% open position. Again, a highly responsive leaf of the discrete-shape binary MLC is one that can achieve a desired position along the continuum of fully opened and fully closed at sufficient speeds such that the mechanics of the MLC do not unduly influence the determination of leaf position at any given time for the delivery of a radiation therapy treatment or fraction.

Referring to FIGS. 5A-5D, the leaf can move to any position in maximum amounts of −y and +y from a starting position of x, at sufficient speeds such that the mechanics of the MLC do not unduly influence the determination of leaf position at any given time for the delivery of a radiation therapy treatment or fraction, which may otherwise be referred to herein as the ability of the leaf or leaves to snap from one position or state to another. The limits of conventional shaping MLCs that contribute to the size of +y, −y are leaves driven by rotational motors or leaf screws which limit the speed at which the leaves can be moved. The ability of the discrete-shape binary collimator, in accordance with embodiments of the present invention, to snap from one state to another, in addition to the amount of time the collimator remains in one state versus another enables an increased ability to modulate radiation intensity over the course of a treatment fraction.

The proposed MLC systems and methods described herein are able to leverage many of the benefits of each type of intensity modulation, volumetric and direct intensity modulation. Because of the high speeds of the leaves, this technology has the "snap-action" benefit of a binary MLC. Moreover, since individual leaves can be precisely controlled, and can quickly move-to and stop-at intermediate locations, each leaf can be used to create sub-beamlets or multiple intensity levels. This can be applied to a single-row style construction where each leaf covers one set of beamlets, or an opposing dual bank leaf configuration can be built where beamlets are defined by two or more leaves. Thus, this configuration has the volume intensity modulation aspects of traditional MLC's, but with the ability to directly intensity modulate beamlets as with binary collimators. In effect, each leaf can be quickly sent to any of a number of magnetically actuateds, at sufficient speeds such that the mechanics of the MLC do not unduly influence the determination of leaf position at any given time for the delivery of a radiation therapy treatment or fraction. Thus, arbitrary 2D patterns can be created very quickly. The resulting MLC can have the speed and simplicity benefits of a binary MLC, but with the flexibility and 2D beam shaping of a conventional shaping MLC hence the name magnetically actuated MLC.

Figure 6:
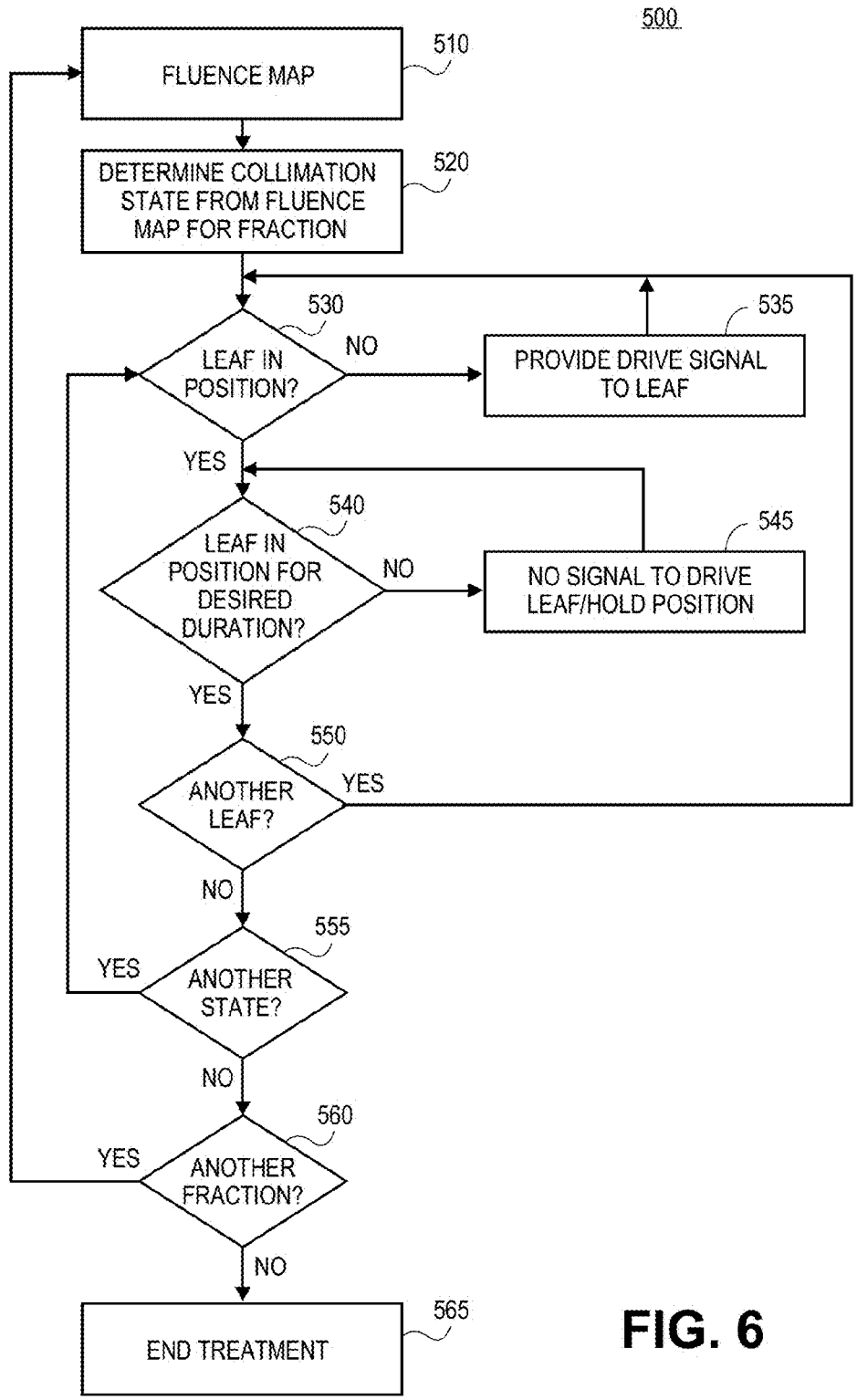
FIG. 6 is a flow chart of a fluence and leaf control scheme for discrete binary multi-leaf collimator.

FIG. 6 illustrates exemplary method 500 for delivering radiation therapy utilizing a magnetically actuated MLC, in accordance with an embodiment of the present invention. It is to be understood that method 500 begins following initial patient set up (e.g., registering an on-line image (optionally utilizing MVCT) with a planning image, and adjusting the patient support, if needed, to properly align the patient for radiation delivery). Fluence map(s) are determined or generated according to the plan (step 510), the sum of which make up a treatment fraction. Radiation delivery for a treatment fraction is initiated by receipt of or access to a treatment plan for a patient. Initiating radiation delivery may include determining and setting the initial position of the gantry, the initial leaf position in the multi-leaf collimator, the initial jaws position for primary and secondary collimation (respectively) of the beam, and other initial actions known to those having skill in the art. It will be appreciated by the skilled artisan that this method may be used for other platforms for delivery of radiation therapy, such as a linear accelerator mounted on a six degree of freedom robot (See FIG. 23B for example).

In this embodiment the fluence map from the treatment plan determines the collimation sequence, e.g., leaf position and time the leaf is in such position (step 520). The fluence map dictates a series of leaf states necessary to achieve the intensity profile of the fluence map. Thereafter, appropriate control signals are sent by the control computer to leaf actuators to move the leaves in accordance with the treatment plan, i.e., to the desired leaf positions for the desired time to achieve the fluence map. A leaf driver receives the control signals and imparts the commanded leaf movement in accordance with the planned fluence map for that beam, and this process is repeated for each leaf or group of leaves as needed to achieve the fluence map for that beam or gantry angle. The treatment fraction comprises delivery of multiple beams at multiple gantry angles, such that the sum of the delivered fluence maps make up the treatment fraction. It is to be appreciated that other treatment system components may be varied (e.g., dynamic gantry motion, couch motion, variable or servo linac output, etc.) in addition to the apertures of the magnetically actuated MLC. This description isolates the MLC in order to focus the discussion, and not by way of limiting the invention to any one use or aspect of the inventive MLC.

At step 520, it is determined if the state of the collimator (i.e., beam or aperture shape) corresponds to or needs to be changed at any particular point within the delivery of a fluence map. This determination, as will be appreciated by the skilled artisan, will be driven by the treatment plan and will be implemented via leaf positioning accomplished as described herein. The position of each leaf is determined and then compared to the position from that collimator state (step 530). If a leaf is not in position, a drive signal is provided (step 535) until the desired position is reached. If the leaf is in the desired position (answer to step 530 is 'YES') then next at step 540 determines if the leaf is in the correct position for the correct or desired duration. If the leaf has not been positioned for the desired duration, then do not drive the leaf or alternatively send a hold signal to a leaf actuator (step 545). If the leaf has been in position for the desired duration, then the system may move that leaf to another position according to the fluence map or treatment plan. At step 550, the system looks at the next leaf to determine whether it is in position and for the desired duration (according to steps 530-545). After all leaves for a desired collimator state have been completed (answer to step 550 is 'NO') next adjust leaves accordingly to achieve another state (answer to step 555 is 'YES'). If there is not another state (answer to step 555 is 'NO'), then delivery of the fluence map or this portion of the treatment plan is completed. If there is another fluence map to deliver at the next gantry angle (answer to step 560 is 'YES') the method returns to step 510 to evaluate/adjust leaf positions accordingly to the steps of method 500. If there is not another treatment fluence map (answer to step 560 is 'NO') then the treatment/fraction ends (step 565).

Over the course of a treatment fraction, a leaf driver receives control signals at various points throughout the treatment plan to set the leaves of a collimator at the appropriate state for the appropriate amounts of time. It is the treatment plan that, in one form or another, controls the leaf driver and the various states of the collimator. The treatment plan, as described and as will be appreciated by the skilled artisan, will have been developed to take advantage of the ability of the magnetically actuated collimator, in accordance with embodiments of the present invention, to snap from one state to an alternate state in order to deliver a better modulated intensity distribution than if the plan was made for conventional MLCs (either binary or shaping MLCs). The treatment plan, as will be appreciated by the skilled artisan, can utilize the snap movements of the collimator as well as delivering during rotation of the gantry and movement of the patient support to achieve increased abilities to modulate the intensity of the delivery. After providing control signals to change the state of the discrete-shape binary MLC or if no state change is required, the method loops back for the next point in the delivery of the treatment plan. The process of determining the position of each leaf in an MLC is described serially. It is to be appreciated that the steps of the method 500 may be conducted serially or in parallel for one or more leaves or where groups of leaves are moved together.

The capabilities of techniques with conventional shaping MLCs using a monotonic sequence of shapes is more often a function of limitations of the conventional MLC's responsiveness or leaf speed than to the requirements of an optimized treatment plan. In contrast, leaf, and beamlet control in magnetically actuated MLC embodiments described herein may follow sequential or monotonic movements when called for by the treatment plan, but are not so limited. Individual leaf, leaf pair or beamlet control is controlled to a degree that movements are not limited to monotonic shapes, but rather responsive to the next desired state, and not dependent upon where in the continuum the next desired state may be located. In other words, at any moment in time the MLC controller may position a leaf to any position at sufficient speeds such that the mechanics of the MLC do not unduly influence the determination of leaf position at any given time for the delivery of a radiation therapy treatment or fraction. This contrasts to conventional MLC control schemes and MLC designs where the desired states are sequential or monotonic by necessity because of slower leaf speed.

Figure 7:
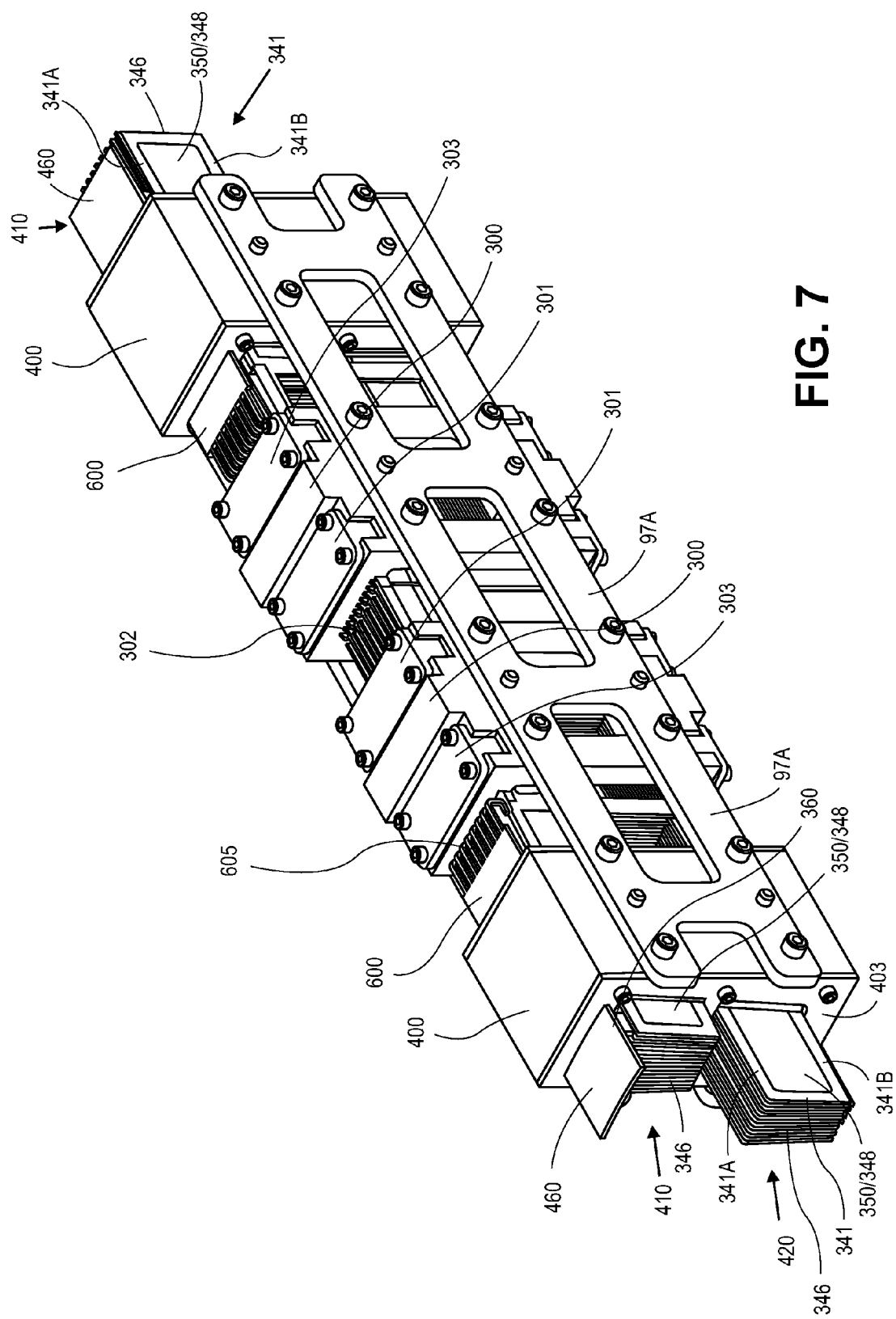
FIG. 7 is an isometric view of an exemplary highly responsive MLC.

FIG. 7 is an isometric view of an exemplary magnetically actuated MLC having dual leaf banks, one on either side of the area 302 into which radiation is directed for collimation. In this specific embodiment, the leaves are driven by electromagnetic action. The leaves are supported by a pair of leaf guide modules 300 (one for each leaf bank) driven by components of an electromagnetic drive system in a pair of electromagnetic drive modules 400, one on each side of the collimator for each bank of leaves. The present invention can be applied to a single bank collimator, but a dual bank is a preferred embodiment. A two part support frame 97A, 97B (FIG. 8) runs along the length of the magnetically actuated MLC and is attached to each of the leaf guide modules 300 and electromagnetic drive modules 400 to support each of the components and insure proper alignment of each to the other. Additional details of magnetically actuated MLC 240 will become apparent in the figures that follow. Details of the electromagnetic drive module 400 are provided with reference to FIGS. 8-10 and 15-18. Details of the leaf guide modules 300 are provided with reference to FIGS. 12-14. Additional details of an exemplary leaf power system are provided with reference to FIGS. 21A-21C and 22.

Figure 8:
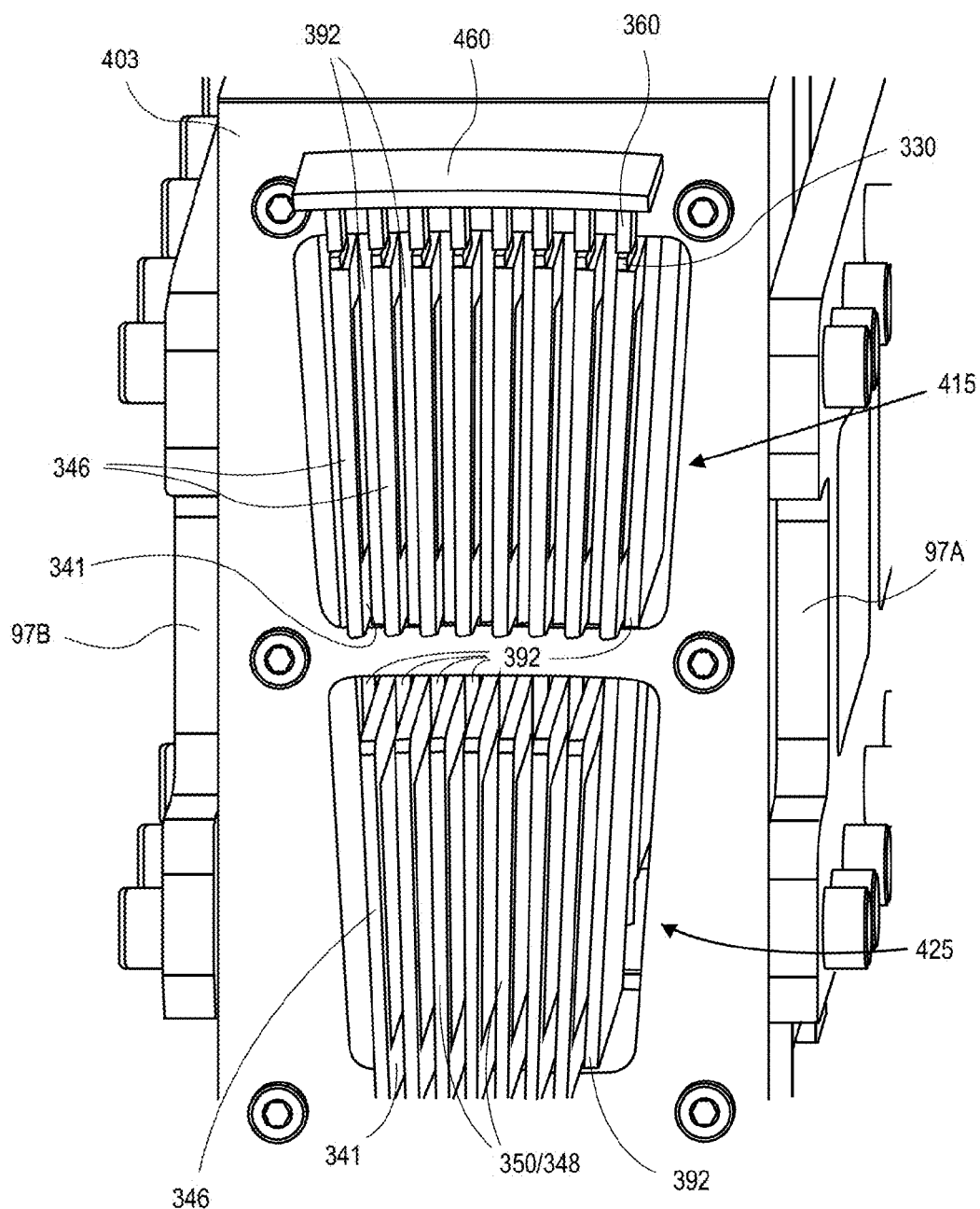
FIG. 8 is an isometric end view of one end of a magnetic drive module of the MLC of FIG. 7.
Figure 9:
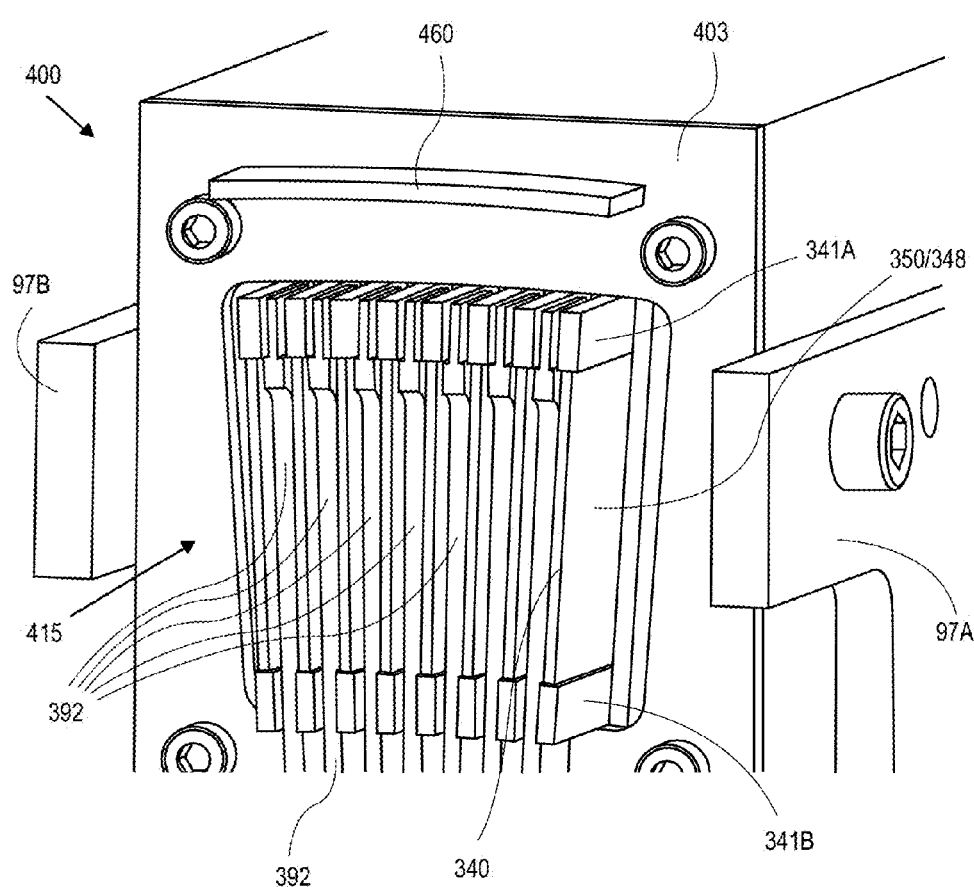
FIG. 9 is a close up an enlarged perspective view of the first leaf bank in the magnet guide module with a portion of the flex circuit and reader removed.
Figure 10:
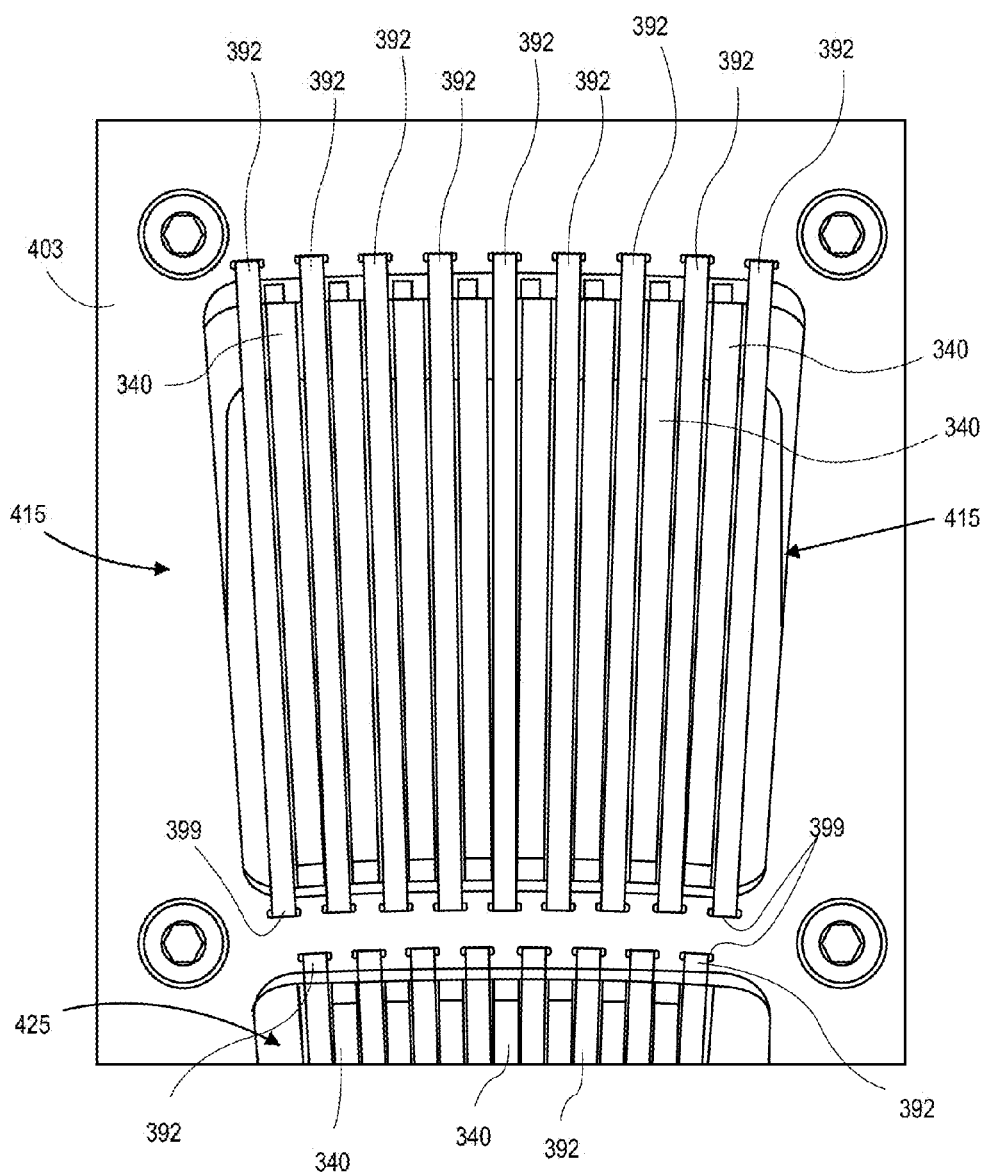
FIG. 10 is an end on view of the magnet guide module with a cover removed to show the arrangement of the stationary magnets between leaves.
Figure 16:
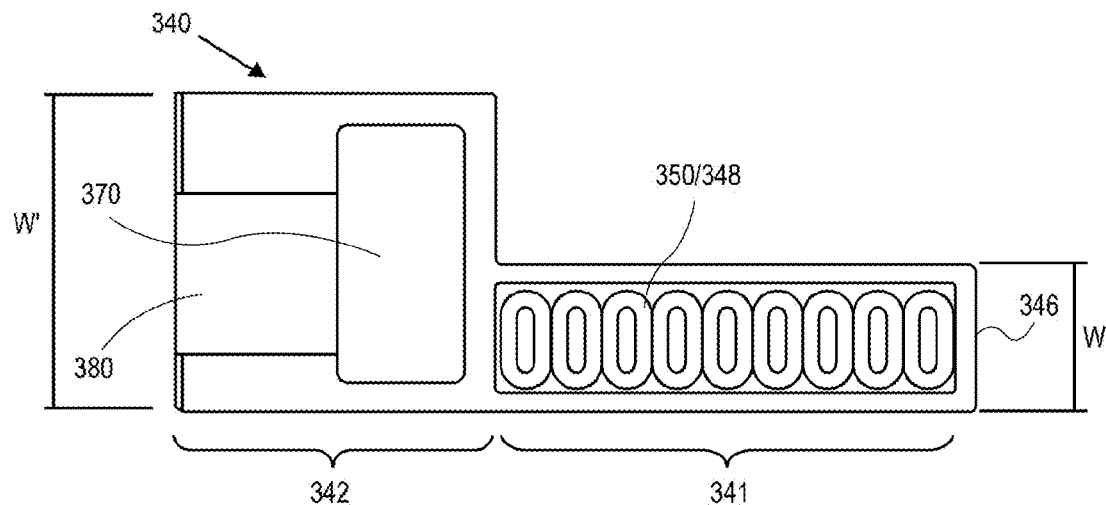
FIG. 16 is a side view of an exemplary leaf.
Figure 17:
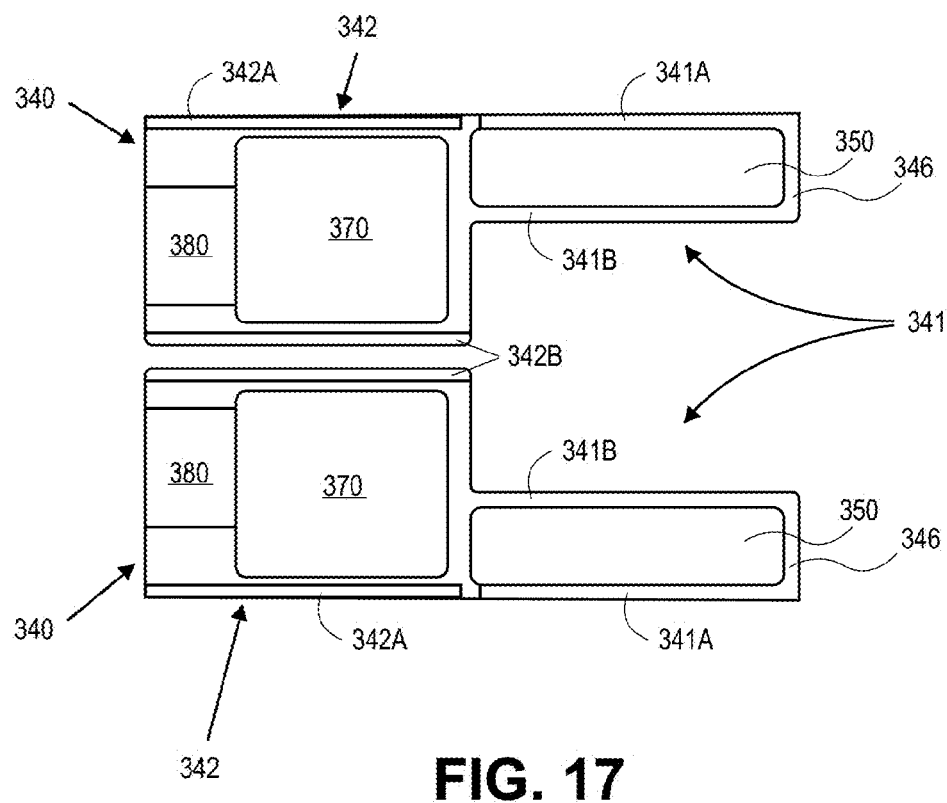
FIG. 17 is a perspective view of an exemplary leaf pair as positioned within an exemplary MLC.

FIG. 8 is an isometric end view of one end of electromagnetic drive module 400 of magnetically actuated MLC 240 of FIG. 7. This view of the magnetic drive module 400 shows upper and lower openings 415, 425 in end plate 403 for one leaf bank of the preferred dual bank MLC of the present invention. In this view, distal ends 346 of drive portion 341 of leaves 340 protrude from the upper and lower openings 415, 425. Stationary magnets 392 are on either side of drive portion 341 of leaf 340, and serve as part of the leaf power system for moving the leaves, as discussed more thoroughly below. Also shown is upper leaf encoder 330 interacting with upper encoder reader 360 and upper flex circuit 460 (lower leaf encoder, lower encoder reader and lower flex circuit not shown). Referring to FIGS. 16-17, width W of drive portion 341 is smaller than width W' of blocking portion 342 to facilitate packing a plurality of leaves 340 adjacent to each other while having stationary magnets 392 (FIG. 10) on either side of drive portion 341 for each leaf. Referring to FIG. 10, stationary magnets 392 on either side of drive portion 341 (which protrude from upper opening 415) are horizontally offset by approximately the thickness of one leaf from the stationary magnets 392 on either side of drive portion 341 (FIG. 9). The geometry and placement of leaves 340 in this embodiment facilitates efficient packing of leaves 340 adjacent to each other with magnets 392 on either side of drive portion 341. The skilled artisan will appreciate that other geometries are available to pack the leaves adjacent to one another and remain within the scope of the present invention. Embodiments of the design and operation of the leaf and encoder is discussed in more detail below with regard to FIGS. 15-18 and 20.

FIG. 9 is an enlarged view of distal ends 346 of drive portion 341 of leaves 340 protruding from upper opening 415 of the electromagnetic drive module 400 of FIG. 8, also showing a portion of the flex circuit 460 and encoder reader 360. The plurality of leaf drive portions 341 are shown in section view. Additional details of the components of a leaf 340 including drive portion 341 are shown and described more fully below in FIGS. 15-18 and 20. The view of FIG. 9 illustrates the arrangement of the leaf drive section upper and lower portions 341A, 341B alongside stationary magnets 392. The lateral thickness of sections 341A, 341B are used to maintain the leaf coil 350/windings 348 in the desired relationship to magnets 392, as discussed more thoroughly below. Alternatively, the skilled artisan will appreciate that the coils can be in the place of the permanent magnets and remain stationary relative to the leaf, and the permanent magnets may be on board and move with the leaf.

Figure 11:
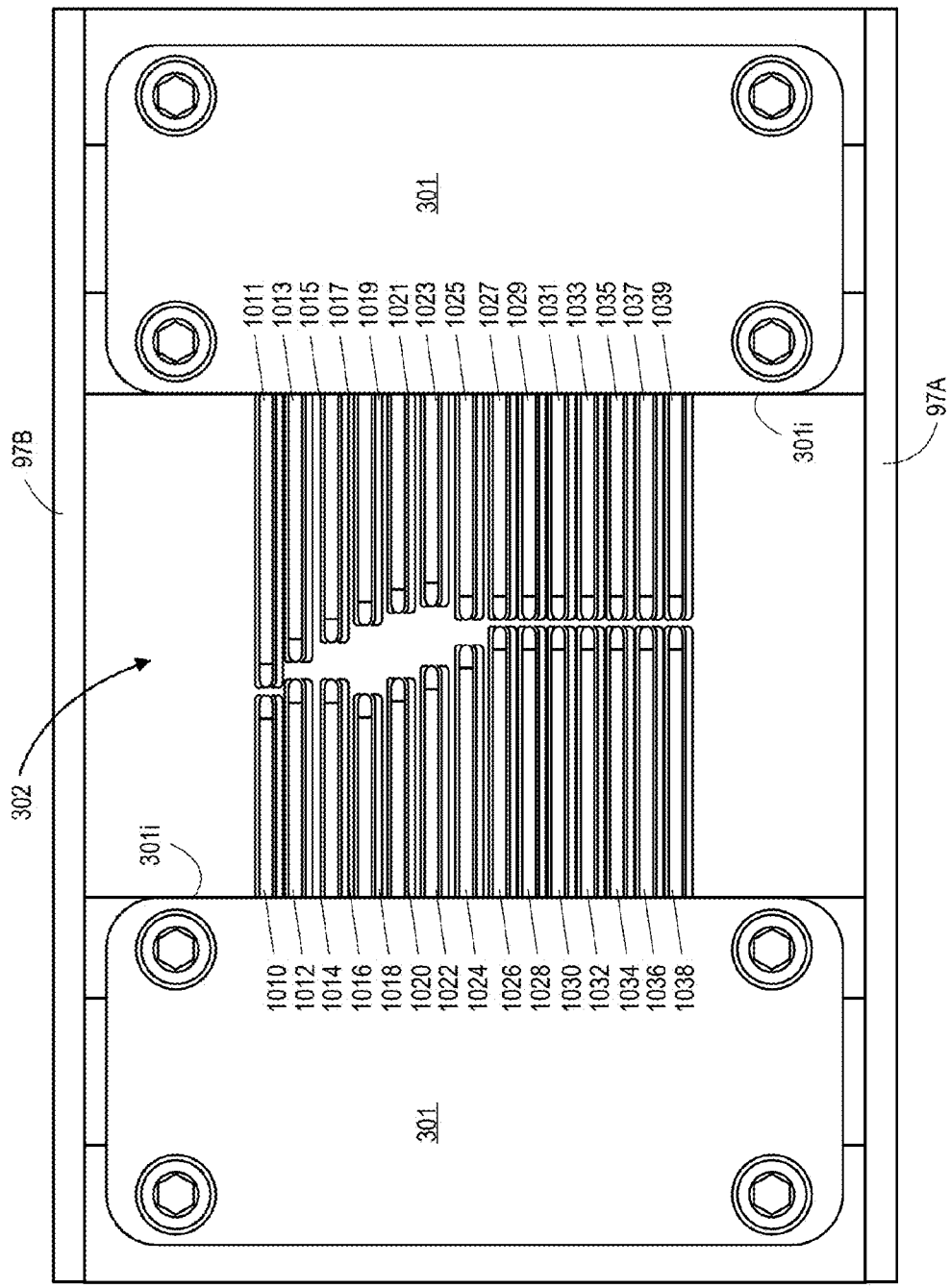
FIG. 11 is a top down view of the inner leaf guides and opening of FIG. 7.

FIG. 11 is a top down view of the central portion 302 of the magnetically actuated MLC 240 of FIG. 7 showing inner leaf guides 301, aperture 1050 and 14 leaf pairs (1010-1039) in various positions between leaf guide inner supports 301. While 14 leaf pairs are shown more or fewer leaf pairs may be provided according to the design requirements of a particular system. In one preferred embodiment, there are 64 leaf pairs, in another embodiment there are 96 leaf pairs and in still another embodiment there are 32 leaf pairs. As will be apparent, radiation is collimated through this section 302 of the collimator.

In FIG. 11, each leaf is positioned in a particular position to define a particular aperture or shape 1050 through which radiation may pass, also referred to herein as a state. Leaf pairs 1010 and 1011 through 1038 and 1039 are controlled using the control schemes and drivers described herein to enable simultaneous volume and intensity modulation. In alternative aspects one or more controllable jaws are used to provide primary collimation of the beam, defined by the inner edges 301*i* and the frames 97A, 97B (i.e., the jaws will block the open space between support frame B and leaf pair 1010/1011 and between support frame A and leaf pair 1038/1039). Additionally or alternatively, the one or more pairs of jaws may be adjusted to reduce the size of the primary collimated beam to smaller than the frame size.

Figure 13A:
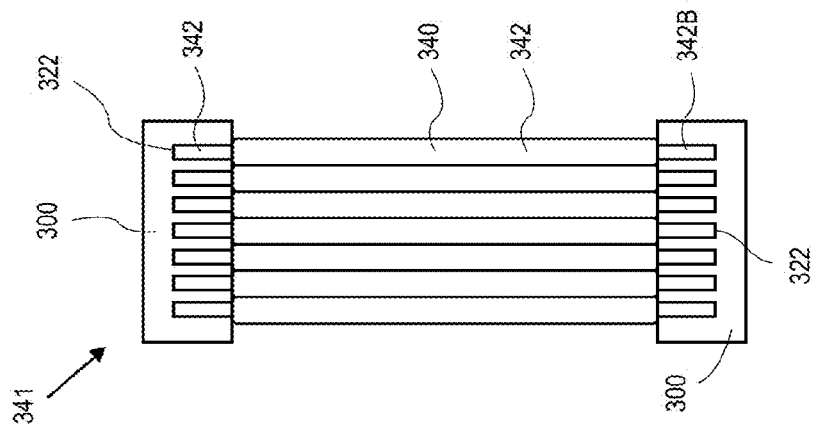
FIGS. 13A and 13B illustrate an end on view of the guide in FIG. 11 showing an end on view of the blocking portion of leaves within their respective guide channels.
Figure 12:
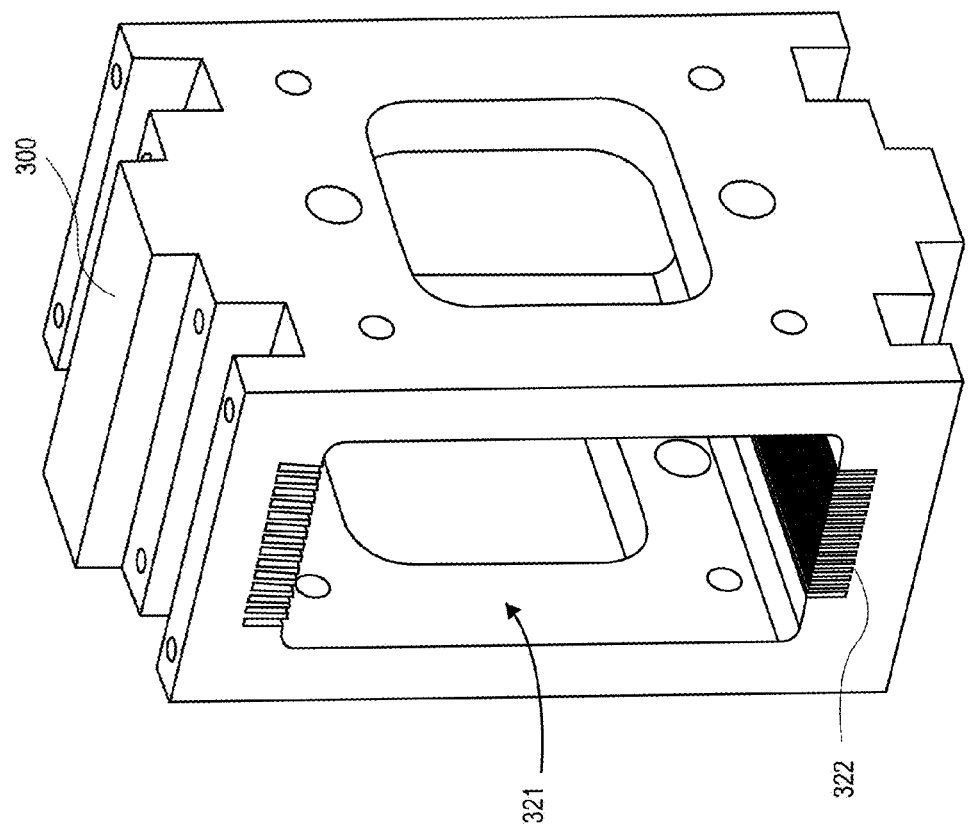
FIG. 12 is a perspective view of an exemplary straight leaf guide.
Figure 13B:
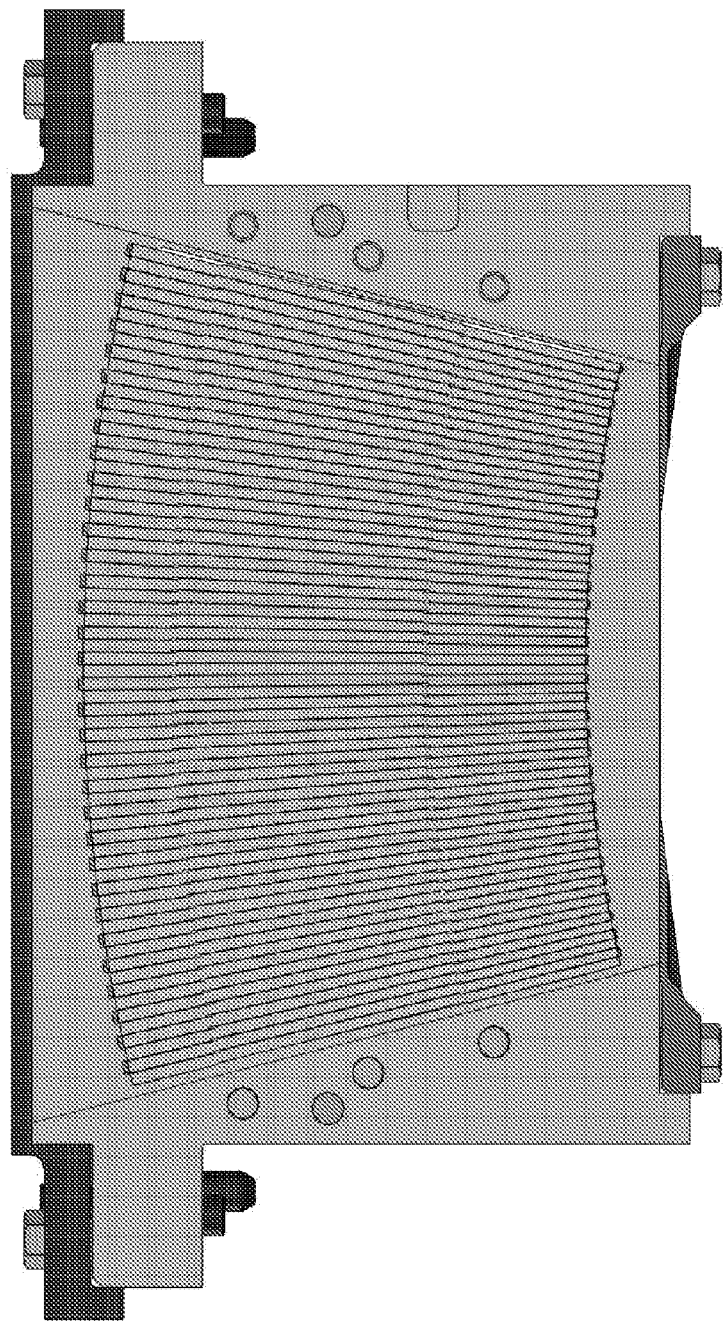

FIG. 12 is a perspective view of an exemplary leaf guide module 300 of a magnetically actuated MLC 240. The leaf guide module 300 has opening 321 sized to receive a plurality of leaves 340. The size of opening 321 varies based on the number of leaves used in a particular MLC design. A plurality of guide channels 322 is provided on the upper and lower surfaces of the guide about the opening. As best seen in FIGS. 13A and 13B, a portion of the leaf 340 is adapted for sliding arrangement into the plurality of guide channels 322. In this embodiment, primarily blocking portion 342 sits within guide channel 322, though driving portion 341 may also occupy some or all of the length of guide channel 322 as a leaf is moved into and out of a desired position. FIG. 13A is an end on view of leaf guide module 300 in FIG. 12 showing an end on view of the blocking portion 342 of seven leaves 340 within their respective guide channels 322. In a preferred embodiment, the leaves 340 will have a tongue and groove construction (FIG. 13B) to prevent leakage between adjacent leaves, as shown by reference number 341. There are edge portions 342*a*, 342*b* of the leaf blocking portion 342 adapted and configured for sliding within the guide channels 322.

Figure 14:
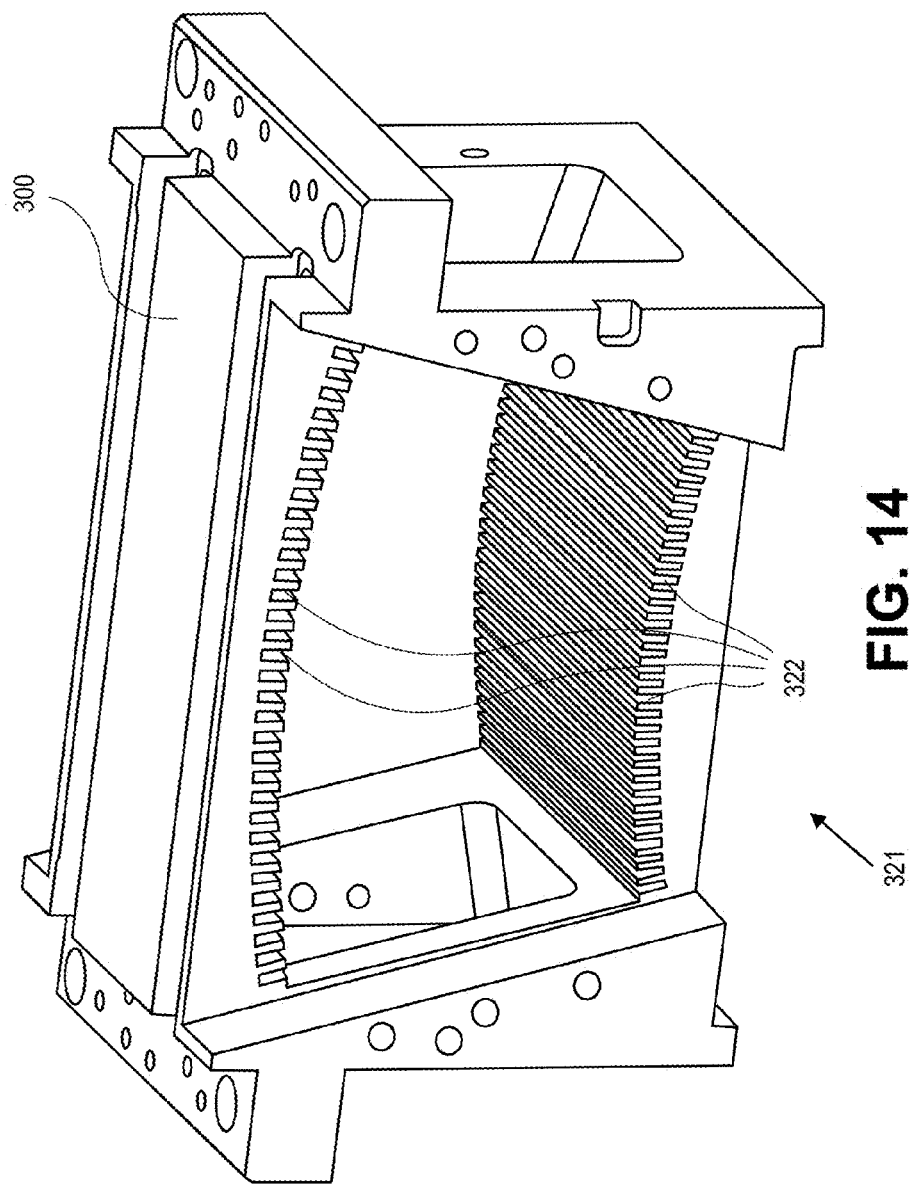
FIG. 14 is a perspective view of an exemplary curved leaf guide.

FIG. 14 is a perspective view of an exemplary curved leaf guide module 300. In this embodiment of leaf guide module 300, opening 321 has an arched shape in contrast to the substantially vertical alignment of the leaf guide embodiment of FIG. 12. A plurality of leaf guide channels 322 is provided in the leaf guide on the upper and lower portions about opening 321.

Figure 15:
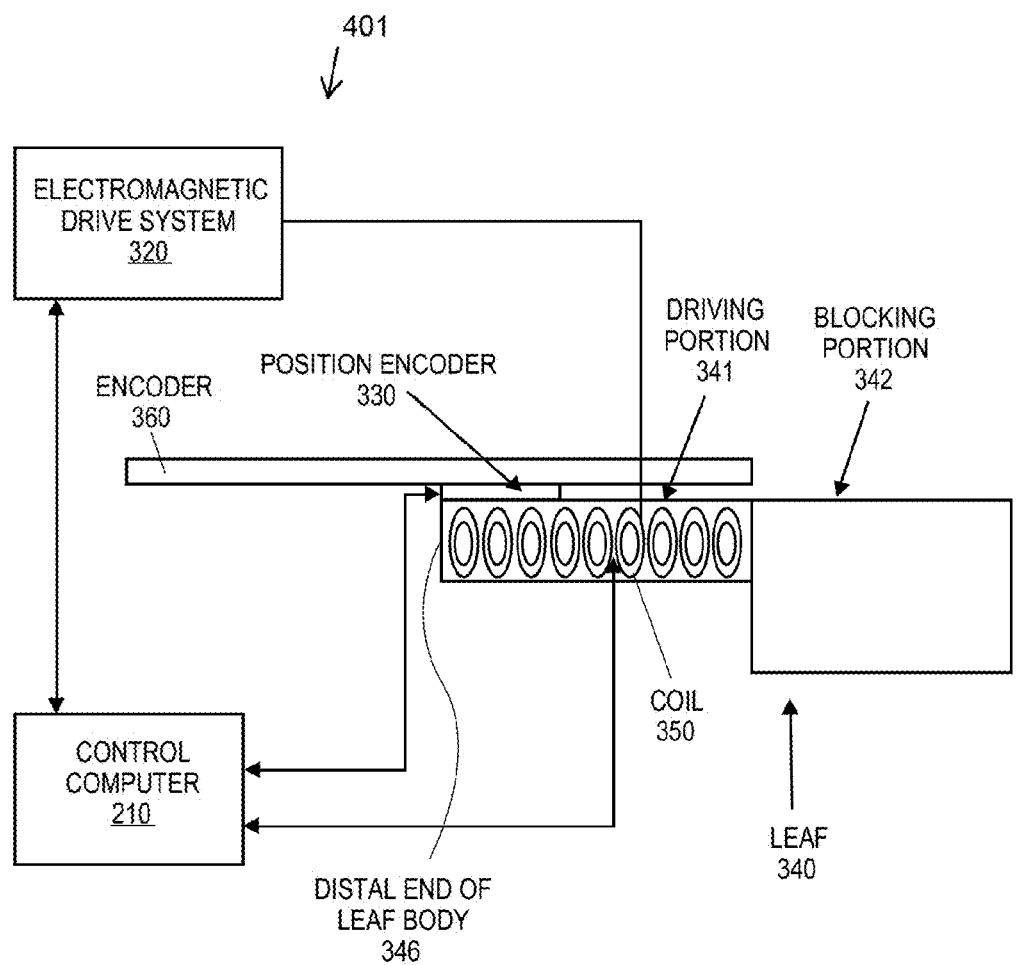
FIG. 15 is a diagram of an exemplary control system for an exemplary leaf in an electromagnetically controlled highly responsive multi-leaf collimator.

FIG. 15 is a diagram of an exemplary control system 401 for a magnetically actuated MLC 240. In this specific magnetically actuated MLC embodiment, the leaf driver is an electromagnetic drive system 320. This figure presents an exemplary leaf 340 of an electromagnetic multileaf collimator 200. Control system 401 may include control computer 210, driver 320, leaf position encoder 330 and leaf 340. Preferably, additional encoder 360 may also be used to provide two forms of positional feedback, depending upon the specific encoder or positioning system configuration. Leaf 340 has a driving portion 341 and a blocking portion 342. Blocking portion 342 is shaped, adapted and configured for blocking the therapeutic beam, made of radio opaque material, preferably tungsten or tungsten alloy and is about 20-70 mm wide. Leaf driving portion 341, attached to blocking portion 342, provides structural support for blocking portion 342 as well as windings or coil 350 and any additional components needed or desired. As noted previously and shown in FIGS. 15-16, width W of blocking portion 342 is larger than width W' of driving portion to facilitate efficient packing of the leaves in the MLC.

There is a leaf position encoder 330 on driving portion 341. The placement of encoder 330 on driving portion 341 will vary depending on specific leaf design considerations. The number and type of additional components needed to be attached will vary depending upon the specific design of a magnetically actuated MLC. In this specific embodiment, leaf driving portion 341 includes components used for an electromagnetic driver (e.g., coils). The size, number and orientation of coils 350 will vary depending upon other factors such as the size, placement and the strength of stationary magnets 392 used in the embodiment of the magnetically actuated MLC, the dimensions available for the components and other factors. As presently envisioned, the number of coils 350 may vary, but the number of coils 350 exposed to electromagnetic drive module 400 and stationary magnets 392 remain approximately constant in order to apply a uniform force to driving portion 341. Alternatively, the skilled artisan will appreciate that the coils can be in the place of the permanent magnets and remain stationary relative to the leaf, and the permanent magnets may be on board and move with the leaf.

Figure 18:
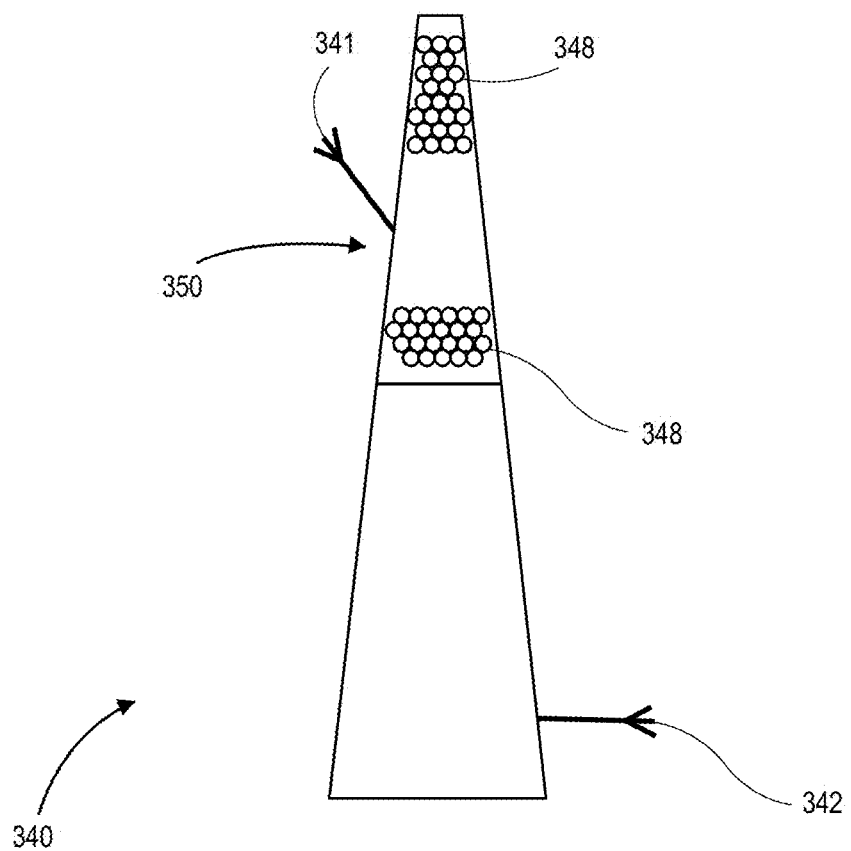
FIG. 18 is a cross-sectional view of coil windings in an exemplary leaf

It is to be appreciated that individual leaf 340 in a magnetically actuated MLC configuration may be modified depending upon the requirements of electromagnetic driver 320. In this exemplary embodiment of an electromagnetic driver, leaf 340 may include coil 350 made from windings 348 (FIG. 18). Control computer 210 receives signals from encoder 360/330 depending upon the specific position system used. In some embodiments, the signals may indicate position data captured by position encoder 330. Control computer 210 processes the received signals and determines whether leaf 340 is at a desired position. If the position of leaf 340 needs to be changed, control computer 210 signals driver 320 to change the position of the leaf Control computer 210 may also provide control signals to drive a magnetic field generated by coil 350. In some embodiments, control computer 210 may control the strength, activate or deactivate the magnetic field of coil 350 by adjusting current flowing through the coils. Additional details of magnetic drive and control are described herein with regard to FIGS. 20 and 21A-21C. In one alternative embodiment, the position encoder 330 on the leaf and the guide mounted encoder 360 are both fed into the control loop to more precisely control the motion of the leaf position. In one alternative embodiment, the position encoder 330 on the leaf and the guide mounted encoder 360 can be compared against each other as a form of secondary positional verification. In still another alternative embodiment, the controller could use current torque applied as a control input for leaf position control.

Figure 22:
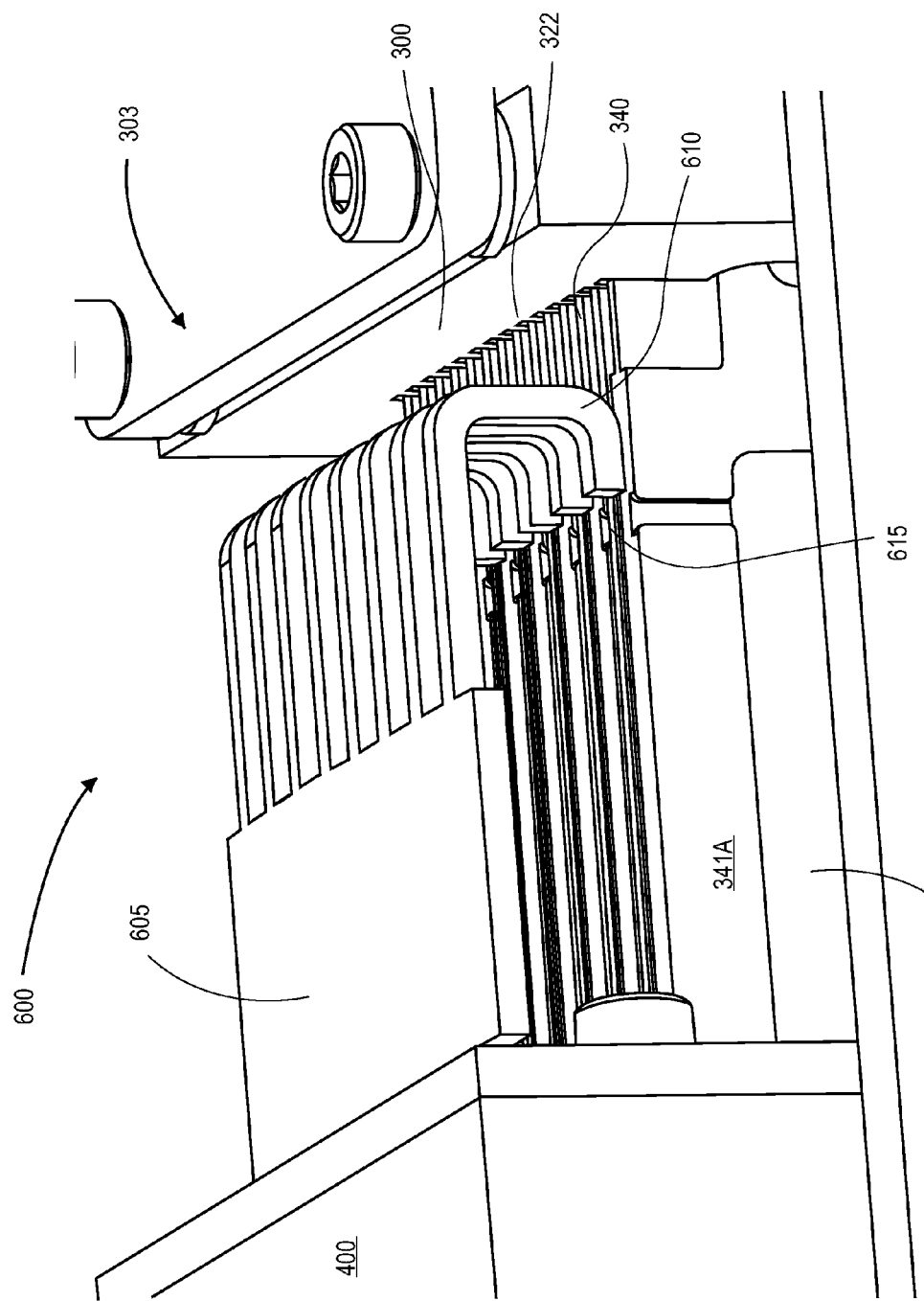
FIG. 22 is an isometric view of a leaf power drive as shown in FIG. 7.

Referring to FIGS. 15 and 22, driver 320 may receive a signal from control computer 210 to provide a current to coils 350 from electrical drive connector 605 (FIGS. 7 and 15). The current results in a magnetic field generated by coils 350. The magnetic field generated by coils 350 acts in concert with the permanent magnets 392 on either side of driving portion 341 within the magnetic drive module 400 to produce controlled leaf movement. Permanent magnets 392 may be arranged parallel to the coils 350. In some embodiments, permanent magnet 392 in magnetic drive module 400 may be at least twice the length of the coils 350 so that the magnet may apply relatively constant driving force to driving portion 341. Whatever the length of magnetic drive module 400, the number of coils adjacent to permanent magnets 392 preferably remains approximately constant so as to apply an approximately constant force to driving portion 341 for any given current and magnetic strength. Coils 350 may extend at least as long as a leaf so that it is controllable to the full leaf width. The coil length or the number of coils is influenced by the amount of desired leaf travel and desired force to move the leaf. The depicted embodiment shows a preferred nine coils, but the number of coils can be selected based on particular needs, for example three or six coils may be used. The skilled artisan will consider many factors, the power input required to move the leaves, and heat dissipation to name two, when selecting the number of coils and the length of the permanent magnets. For example, if a 6 cm leaf travel is desired, then the stationary magnets should be 6+ cm in length (the extra provided for margin), and the space occupied by the coils would preferably be twice that length, or 12+ cm to insure it always engages with the magnet through the entire leaf motion. The coil height is preferably as high as space will permit to make the motor more powerful or efficient. The magnetic fields from the coils and permanent magnet may result in movement of leaf 340 within a magnet and the leaf guide tracks to change the shape and size of the collimated opening aperture (See FIG. 11). A first magnetic field may be generated by a permanent magnet made of a material such as neodymium or other high density strong permanent magnet. The strength of the magnetic fields from the coils and the permanent magnets may be constant as the leaf is driven through the guides. In the preferred leaf embodiments, the coils are potted to the leaf with a material selected for its thermal, mechanical and environmental properties. Table 1 below provides some estimated specifications for 3, 6 and 9 coil embodiments of a leaf design, where the 9 leaf embodiment is estimated to move at least approximately 1 m/s with an acceleration of approximately 80 m/s$^2$ (a trapezoidal acceleration rate with a peak velocity of approximately 2 m/s in approximately 0.25 ms).

TABLE 1

|  | 3 Coil | 6 Coil | 9 Coil |
| --- | --- | --- | --- |
| Total Moving Mass (gr) | 362.25 | 374.07 | 385.8 |
| Accel Force Req'd (N) | 28.98 | 29.93 | 30.85 |
| Req'd Current (amps) | 5.91 | 3.05 | 2.10 |
| I R Heating (watts) | 287 (28.7 @10% Duty) | 153 (15.3 @10% Duty) | 108 (10.8 @10% Duty) |
| Req'd Voltage (cold R) | 48.63 | 50.25 | 51.7 |

FIG. 16 is a side view of an exemplary leaf. A leaf 340 may include driving portion 341 and blocking portion 342. Driving portion 341 includes proximal end connected to blocking portion 342 and distal portion 346. Driving portion can have any suitable dimensions, but preferably is approximately 135 mm×35 mm. In this illustrative embodiment, driving portion 341 may also include a plurality of windings 348 to form coils 350. When current is applied to these coils, for example by electrical drive connector 605 (FIGS. 7 and 22), the interaction between these coils and the flux density created by the stationary magnets produces a force in the direction of motion desired. Coils 350 may be constructed from a conductive material, such as AWG copper wire. The diameter of the wire and the number of turns may be based on the amount of desired torque among other properties, for example, as will be appreciated by the skilled artisan. Alternatively, the skilled artisan will appreciate that the coils can be in the place of the permanent magnets and remain stationary relative to the leaf, and the permanent magnets may be on board and move with the leaf.

Blocking portion 342 is sized and shaped to move within guide structure 300 (see e.g., FIGS. 12 and 13A). In one aspect, blocking portion 342 may be a composite structure made from different materials. In this embodiment, blocking portions 342 include first portion 370 and second portion 380. First portion 370 is preferably made from a radio opaque material such as tungsten or alloy thereof and forms all or nearly all of blocking portion 342. Second portion 380 (the portion not intended to block radiation, but rather move through the leaf guiding structure or motor support areas) is preferably made from a lighter or less dense material to minimize leaf mass (including without limitation aluminum or stainless steel), reduce friction and facilitate ease of leaf acceleration and deceleration.

FIG. 17 is a perspective view of an exemplary pair of leaves 340 as would be oriented in the magnetic drive and leaf guide structures of the MLC of FIG. 12. Blocking portion 342 is sized and shaped to move within guide structure 300. Guide rails 342A and 342B on each side of the blocking portion 342 are adapted and configured for sliding cooperation with channels 322 in leaf guide 300.

FIG. 18 is a cross-sectional view of leaf 340 having a tapered cross section resulting in varying thicknesses of blocking portion 342 and driving portion 341. In this view one coil 350 made of coil windings 348 is shown within driving section 341. Due to the tapered cross section shape of the leaf, windings 348 have the same number of turns but are arranged to accommodate the available space.

Figure 19:
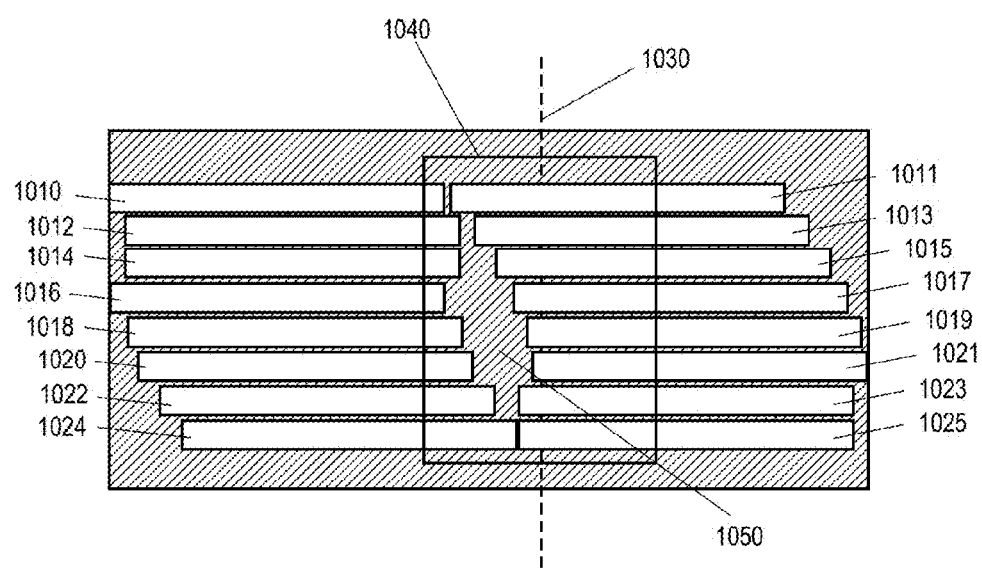
FIG. 19 illustrates an exemplary leaf arrangement for a discrete binary MLC.

FIG. 19 illustrates an exemplary discrete binary MLC leaf arrangement. A collimated field 1040 having a center line 1030 is provided by a pair of jaws or other collimator device (see FIG. 3). In the illustrative embodiment, two leaves form a complementary leaf pair for shaping and modulation of the collimated field 1040. For example, leaves 1010 and 1011 are one leaf pair. Leaves 1018, 1019 are another and leaves 1024, 1025 still another. Each leaf in each pair may be positioned anywhere within field 1040. The inner edges of each leaf within a leaf pair face each other and may create an opening, the collection of openings formed by each leaf pair forms aperture 1050. Aperture 1050 corresponds to an aperture of FIG. 11 previously described and is set according to a treatment plan. Following the method 500 (FIG. 6) an aperture 1050 is determined prior to administering radiation therapy to a patient in the treatment planning process, and occurs at a particular point during delivery of the treatment plan. Aperture 1050 may change according to a number of factors, such as for example, the three dimensional shape of the treatment area, intensity modulation, fluence, and beamlets within a treatment volume as described above. Embodiments of the highly responsive MLCs described herein achieve volume and intensity modulation alone or in simultaneous combination by providing snap state control.

Figure 20:
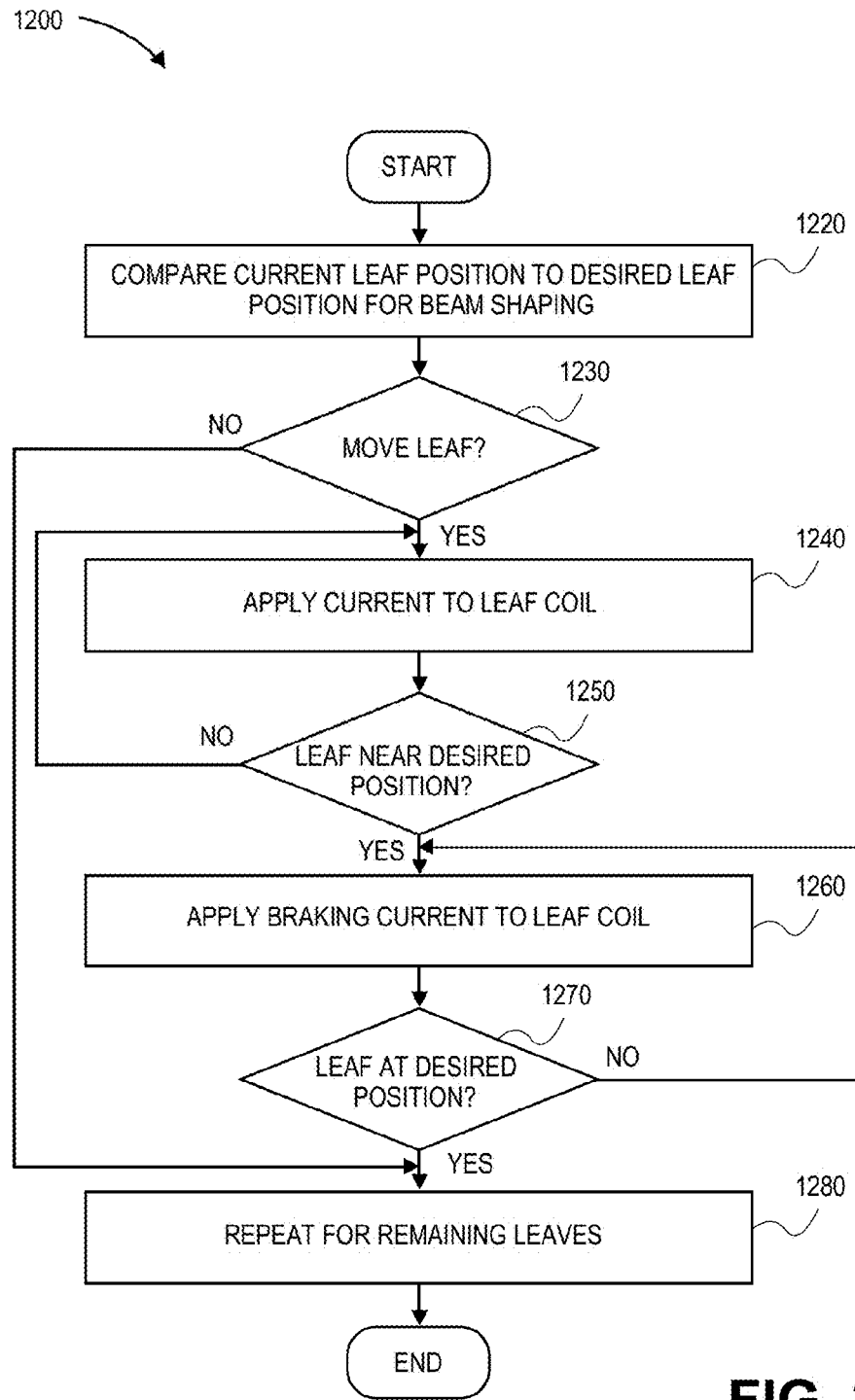
FIG. 20 illustrates an exemplary method for positioning a leaf using an electromagnetically controlled discrete binary MLC.

FIG. 20 is an exemplary method for using an electromagnetically driven discrete binary MLC (i.e., eMLC). The MLC is controlled as described above in the method 500 of FIG. 6 with appropriate electromagnetic drive signals used to move or hold each leaf in position depending upon the specific implementation of an electromagnetic drive system. The method steps described in FIG. 6 at steps 530, 535, 540 and 545 are thus met by providing drive, control and hold signals as needed to control leaf movement.

FIG. 20 illustrates an exemplary method for delivering radiation therapy utilizing an electromagnetic multileaf collimator (eMLC). Radiation treatment for delivering a dose for a current treatment plan is initiated in accordance with a treatment plan. At any particular point in delivery of a treatment plan the state of the eMLC is obtained from the treatment plan. It is determined whether the present state of the eMLC matches the desired state. If yes, the treatment proceeds until the next point within the treatment plan where the same question is asked again. If the present state of the eMLC is not the same as the desired or planned state, then appropriate signals are sent to controller to snap the appropriate leaves to a different position to achieve the desired state. This desired state is maintained until the next point in the treatment plan, where a determination is made whether the present state of the eMLC is the desired state. If the state of an eMLC will be changed, in accordance with the treatment plan, then magnetic field control signals are provided to snap the appropriate leaves to the desired position to achieve the desired state. With reference to FIG. 15, the magnetic field control signals are initially sent by control computer 210 to driver 320. Driver 320 receives the control signals and provides a current to one or more coils to create a magnetic field in the particular coils of the involved leaf. The magnetic field generated by the coils cooperates with a magnetic field of the permanent magnets proximate to the coils and leafs to move the leaves in a desired direction. Optionally, the process repeats for leaves in the MLC.

FIG. 20 illustrates an exemplary method 1200 for positioning a leaf using the electromagnetic control system 401 described herein. The steps shown are part of an overall MLC and treatment plan as described above in FIG. 6 and method 500. The method 1200 corresponds to decisions made in method 500 to move a leaf using an electromagnetic MLC control scheme (see FIG. 6). A desired leaf position is determined based on, for example and without limitation, gantry position, patient position, or desired fluence map according to a treatment plan as in steps 510, 520 above.

The current leaf position and desired leaf position for field shaping are compared at step 1220. The comparison is used to answer the question "leaf in position?" asked in step 530 of the method 500 (see FIG. 6). The current leaf position for each leaf may be determined by signals provided by a flex circuit and encoder read head to control computer (FIGS. 8 and 15, for example). The desired location for each leaf may be determined as discussed with respect to steps 510, 520 above. A determination is made at step 1230 as to whether a leaf should be moved. A leaf is moved if the current position of the leaf does not satisfy the desired position of the leaf. If the leaf does not need to be moved, the process continues to step 1280 where remaining leaves are moved if needed.

If the leaf does need to be moved, a current is applied to the leaf coil at step 1240. The current is applied by driver 320 of FIG. 15 which receives control signals from control computer 210 (see FIGS. 3 and 4). The current applied to the leaf may vary. At first, the current may ramp up to a level required to initiate movement of the leaf and overcome friction between the leaf and any object in contact with the leaf while at rest.

A determination is made as to whether the leaf is near the desired position at step 1250. As current is applied to the leaf coil and the leaf changes position, the leaf position may be detected by a flex circuit and encoder read head. A leaf position "near the desired position" may be a position at which a braking current may be applied to slow down movement of the leaf such that it will stop at the desired position, preferably within approximately ±10 microns of the desired position. A braking current may comprise reducing current to the coils thereby reducing the magnetic field of the coils which will reduce the amount of force exerted on the driving portion, and friction will act to reduce the leaf speed. Alternatively, the current to the coils may be reversed in one or more of the coils to create an opposite magnetic field which acting in cooperation with the permanent magnetic field will act as a braking force in combination with friction. Alternatively a physical braking force in addition to normal friction from the guides could be applied. The skilled artisan will appreciate that many different forms of a braking force could be applied without deviating from the scope of the present invention, and that these are but a few examples. The point at which a braking force is applied, as will be appreciated by the skilled artisan, will depend on the system configuration and that of the control system dynamics, and if the detected position is not at the position where braking is to be applied, the method returns to step 1240. If the detected position is near the desired braking position, a braking current may be applied to the leaf coil at step 1260 such that the leaf will stop motion within approximately ±10 microns of the desired position.

A determination is made at step 1270 as to whether the leaf is at the desired position. If the leaf is not at the desired position, the method 1200 of FIG. 20 returns to step 1260 where braking current is applied to the coil (alternatively to apply greater or lesser braking force (as applicable)) in the event the leaf has continued motion, or to 1240 to initiate or accelerate leaf motion in the proper direction, if the leaf is not in motion or not moving quickly enough. If the leaf is at the desired position, the position change for the current leaf is complete and the remaining leaf positions are changed if needed (step 1280). It will be appreciated that the method of FIG. 20 may apply to moving leaves in parallel as well as serially. Thereafter, adjusting the state of the eMLC proceeds according to the steps 555 and 560 for additional sequences, fractions of fluence maps according to the method 500.

Figure 21A:
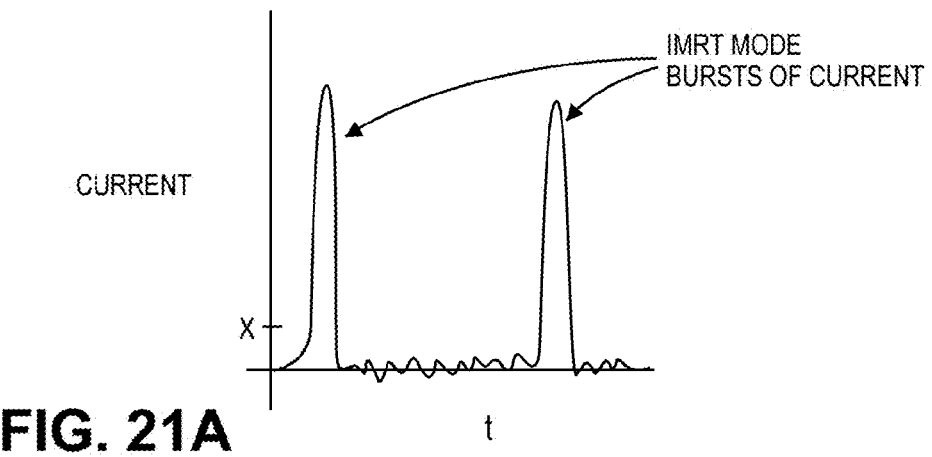
FIGS. 21A, 21B and 21C illustrate representative drive current schemes for various leaf positioning scenarios used in an electromagnetically actuated multi-leaf collimator.
Figure 21B:
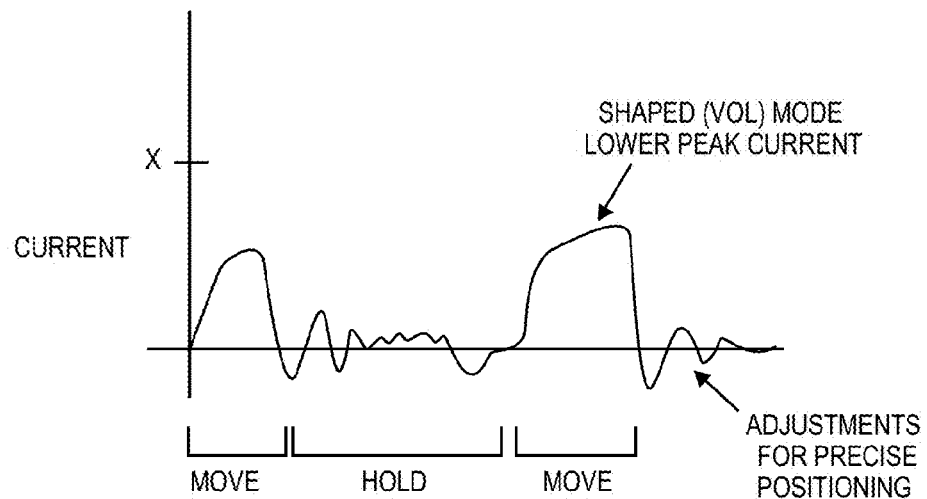
Figure 21C:
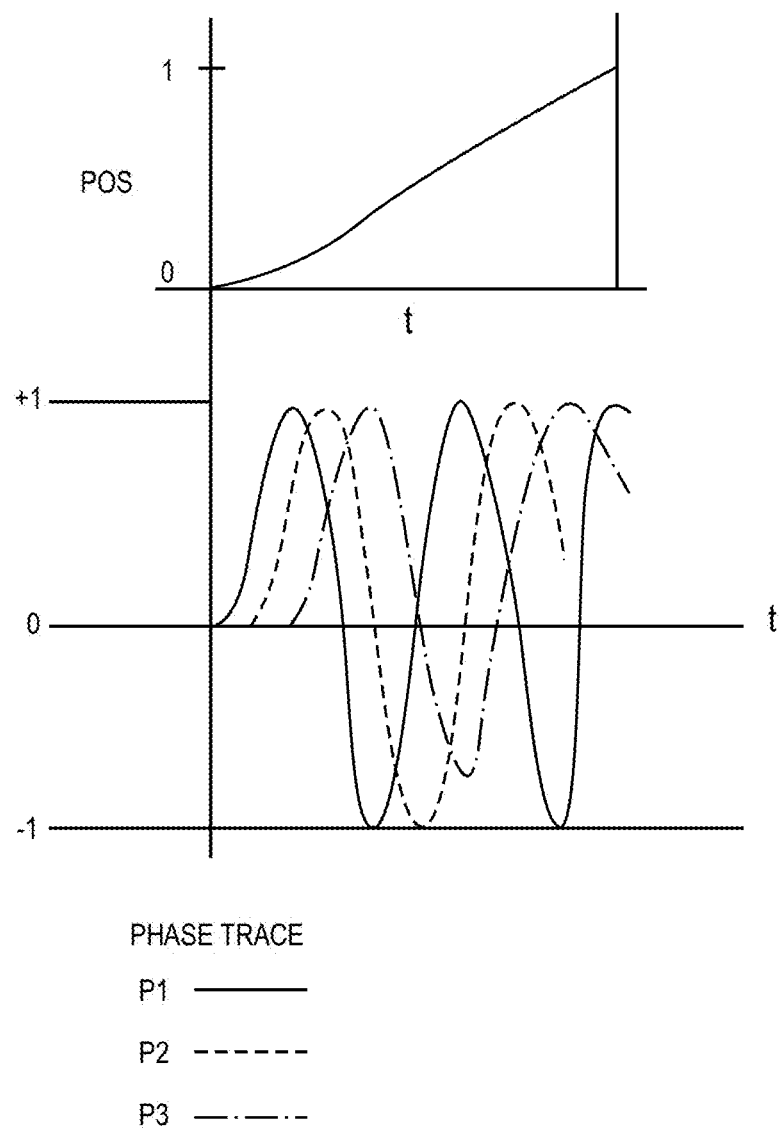

FIGS. 21A, 21B and 21C illustrate representative drive current schemes for various leaf positioning scenarios used in an electromagnetically actuated multi-leaf collimator.

FIG. 21A illustrates a current pulse for a high power burst mode. This control mode will be described in conjunction with the leaf movement methods of FIG. 20. In this mode, the leaf control system is driven so as to move a leaf from one position to another as rapidly as possible. In this mode of leaf action, the system may apply maximum drive current in a short pulse based on time rather than position. In one aspect of this scheme, the leaf drive system may operate in an open loop scheme driving current without regard to input from positions sensors. In terms of the leaf positioning method in FIG. 20, if the state of the eMLC collimator needs to be changed these high current pulses may be considered part of either driving, braking or holding a leaf of an eMLC. In other words, in the high pulse rapid movement mode, the drive control signals move a leaf a rapidly as possible.

Returning to FIG. 21A, this drive current profile also illustrates how the system is able to provide a peak drive current that is many times greater than the mean drive current (x). In one aspect, the peak drive current in the leaf control system is 50 times, 75 times or even 100 times the mean drive current x. In contrast, conventional systems operate with a peak current that is only about 2 times the mean peak current.

FIG. 21B illustrates an exemplary drive control scheme for precise movement during leaf positioning that will be described in conjunction with the leaf movement methods of FIG. 20. This control scheme may be used to achieve the positioning and braking described in FIG. 20. The process of applying a current to a leaf (step 1240) will vary as the position feedback system indicates the leaf is in motion, at the desired movement (e.g., accelerating, steady state velocity, decelerating) or holding a desired position (i.e., no movement). The current demands for a leaf in these different states are different. For example, during the hold phase, the leaf control system provides a hold current to maintain the leaf position. The "hold phase" current level would likely be different from that needed to accelerate or maintain the velocity of a leaf. This process may include many cycles of steps 1230, 1240 and 1250 on a very small scale depending upon the precision of the positioning system and the desired degree of positioning accuracy during the hold step.

FIG. 21C illustrates the use of the drive currents as a secondary position sensor. This figure illustrates the phase current drive (lower graph) used as a predictor for position (upper graph). In this way, phase current used to drive a leaf may be checked within the position control system as a secondary positioning indicator to the leaf position indicator (i.e., leaf position encoders or other positioning system used by the system—see FIGS. 13 and 22).

FIG. 22 is an isometric view of an exemplary leaf driver circuit positioned between the magnet guide module 400 and the leaf support module 303 of FIG. 7. The power drive module 600 includes a drive connector 605 with a flex connector 610 extending into sliding electrical contact with a power connector or power pick up 615 on a leaf 340. The power pick up 615 provides current to the windings 348 of the one or more coils 350 via electrical connectors on the leaf driving portion 341. Power may be provided to the coils by a brushed type connection or a flexible circuit with either direct wiring from the flex to the coils or with some intermediate connector, which will be appreciated by the skilled artisan.

As the specific examples of FIGS. 21A and 21B illustrate, embodiments of the highly responsive leaf control system are adapted and configured to provide individual leaf positioning solutions to provide both IMRT and, if needed, VMRT position solutions alone or in combination on a leaf by leaf basis. As a result, the magnetically actuated MLC, in accordance with embodiments of the present invention (the eMLC being one such embodiment), enables new treatment approaches with improved conformality and speed of delivery.

Figure 23A:
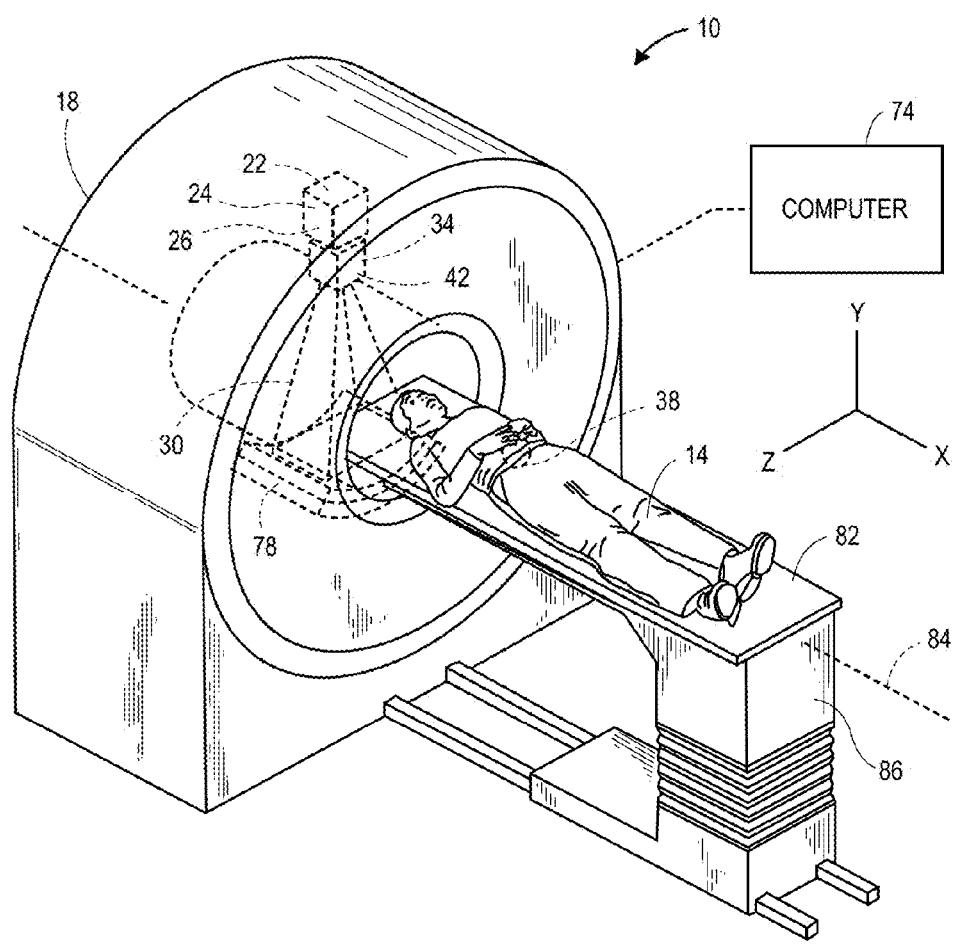
FIGS. 23A and 23B illustrate a perspective view of a gantry based radiation therapy treatment system and robotic based radiation therapy system, respectively.

FIG. 23A illustrates a radiation therapy treatment system 10 that can provide radiation therapy to a patient 14 utilizing MLCs in accordance with embodiments of the present invention. The radiation therapy treatment system 10 includes a gantry 18. Gantry 18 can support radiation module 22, which can include radiation source 24 and linear accelerator 26 operable to generate beam 30 of radiation. Though gantry 18 shown in the drawings is a ring gantry, i.e., it extends through a full 360° arc to create a complete ring or circle, other types of mounting arrangements may also be employed. For example, a non-ring-shaped gantry, such as a C-type, partial ring gantry, or robotic arm could be used. Any other framework capable of positioning radiation module 22 at various rotational and/or axial positions relative to patient 14 may also be employed. In addition, radiation source 24 may travel in a path that does not follow the shape of gantry 18. For example, radiation source 24 may travel in a non-circular path even though the illustrated gantry 18 is generally circular-shaped. The radiation therapy treatment can include photon-based radiation therapy, brachytherapy, electron beam therapy, proton, neutron, or particle therapy, or other types of treatment therapy. Radiation module 22 can also include modulation system 200 operable to modify or modulate radiation beam 30. Modulation device 200 provides the modulation of the radiation beam 30 and directs radiation beam 30 toward patient 14. Specifically, radiation beam 30 is directed toward a portion of the patient. The radiation modulation system in accordance with embodiments of the present invention is described in more detail above.

Modulation device 34 can include collimation device 42, as illustrated in FIG. 3 and FIGS. 7-19. Collimation device 42 includes a set of jaws 46 that alone or in combination with the primary collimator defines and adjusts the size of aperture 50 through which radiation beam 30 may pass to provide primary collimation. Jaws 46 include upper jaw 54 and lower jaw 58. Upper jaw 54 and lower jaw 58 are moveable to adjust the size of aperture 50.

Figure 23B:
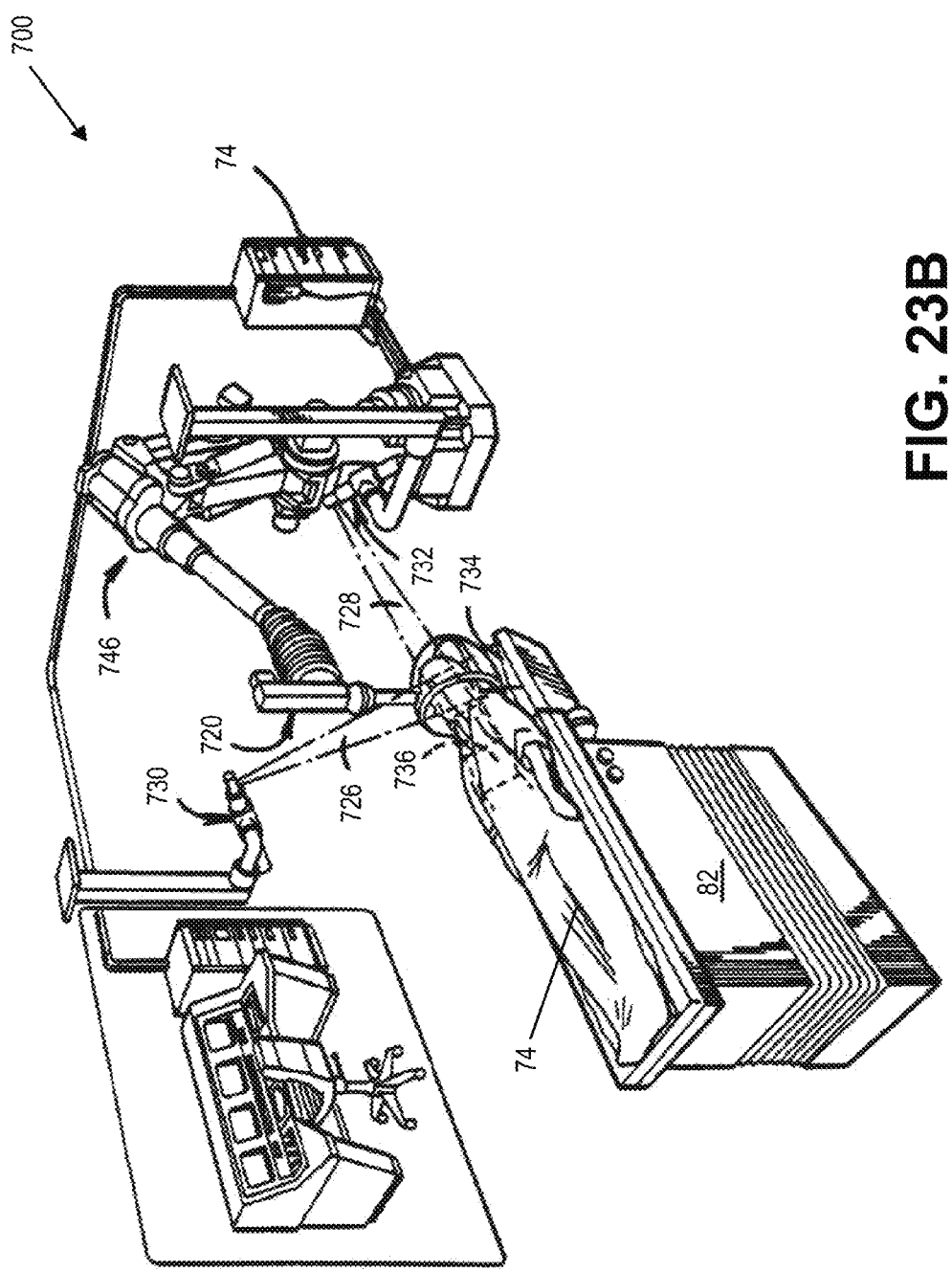

FIG. 23B illustrates an embodiment of a radiation system 700 having a radiation source and modulation device mounted on a robotic arm. The radiation system 700 is similar to the radiation system 10 described herein. FIG. 23B includes a radiation module 720 similar to radiation module 22 including, for example, a linear accelerator and an embodiment of the modulation device is mounted on a robotic arm 746. The robotic arm 746 moves with 6 axes of motion under control of the computer controller 74 to position the radiation source 720 freely and in 6 degrees of freedom about the patient's body, up or down, longitudinally along the patient or laterally along the patient. Also shown are a pair of in room diagnostic imaging devices 730, 732 that direct one or more imaging beams 726, 732 towards the patient 14 and appropriate image receivers 734, 736. Radiation systems similar to those illustrated in FIG. 23B are commercially available from Accuray, Incorporated of Sunnyvale, Calif. under the Cyber Knife® product line. Additional details of this type of radiation treatment system are described in U.S. Pat. No. 5,207,223, issued May 4, 1993, titled "APPARATUS FOR AND METHOD OF PERFORMING STEREOTAXIC SURGERY," by John R. Adler; U.S. Pat. No. 5,430,308, issued Jul. 4, 1995, titled "3-DIMENSIONAL RADIATION DOSIMETER," by Feichtner et al.; U.S. Pat. No. 7,046,765 B2, issued May 16, 2006, titled "RADIOSURGERY X-RAY SYSTEM WITH COLLISION AVOIDANCE SUBSYSTEM," by Wong et al.; U.S. Pat. No. 7,266,176 B2, issued Sep. 4, 2007, titled "WORKSPACE OPTIMIZATION FOR RADIATION TREATMENT DELIVERY SYSTEM," by Allison et al; and U.S. patent application Ser. No. 11/824,080, filed Jun. 29, 2007, titled "ROBOTIC ARM FOR A RADIATION TREATMENT SYSTEM," to Kuduvalli et al., now Publication No. US-2009-0003975-A1, published Jan. 1, 2009.

Figure 24:
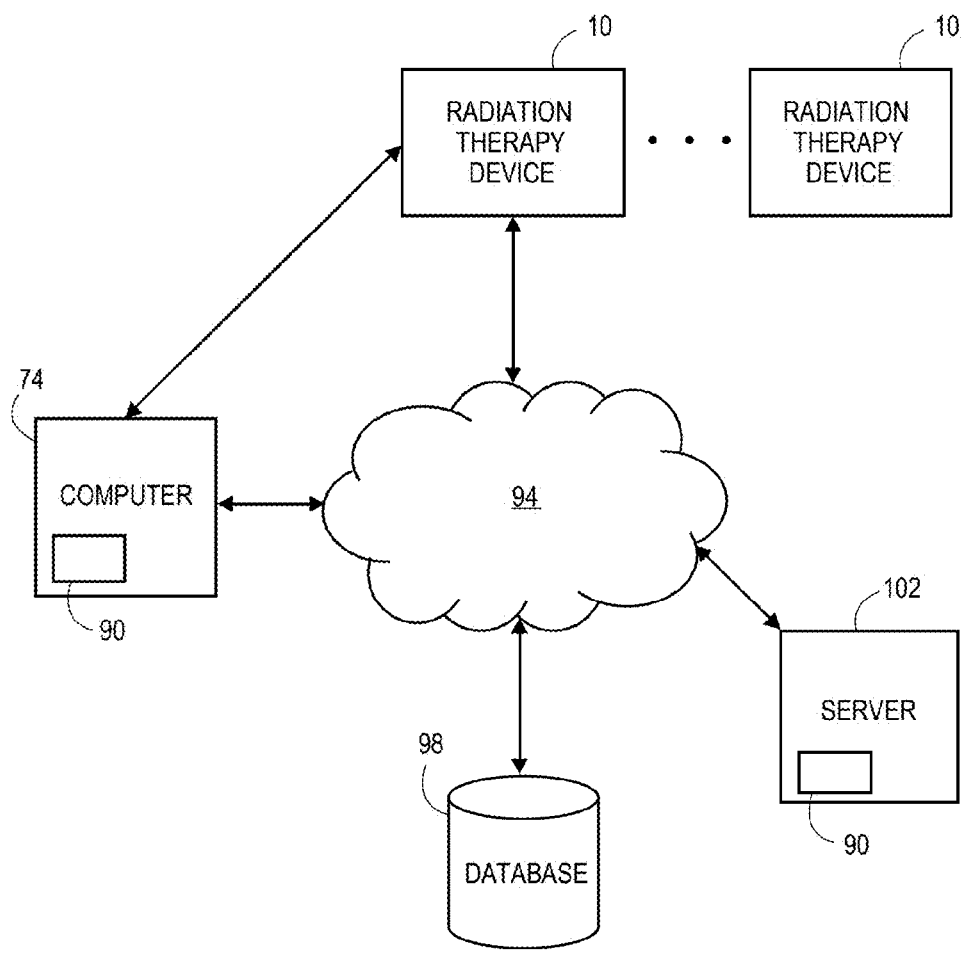
FIG. 24 is a schematic illustration of the radiation therapy treatment system in FIGS. 23A and 23B.
Figure 25:
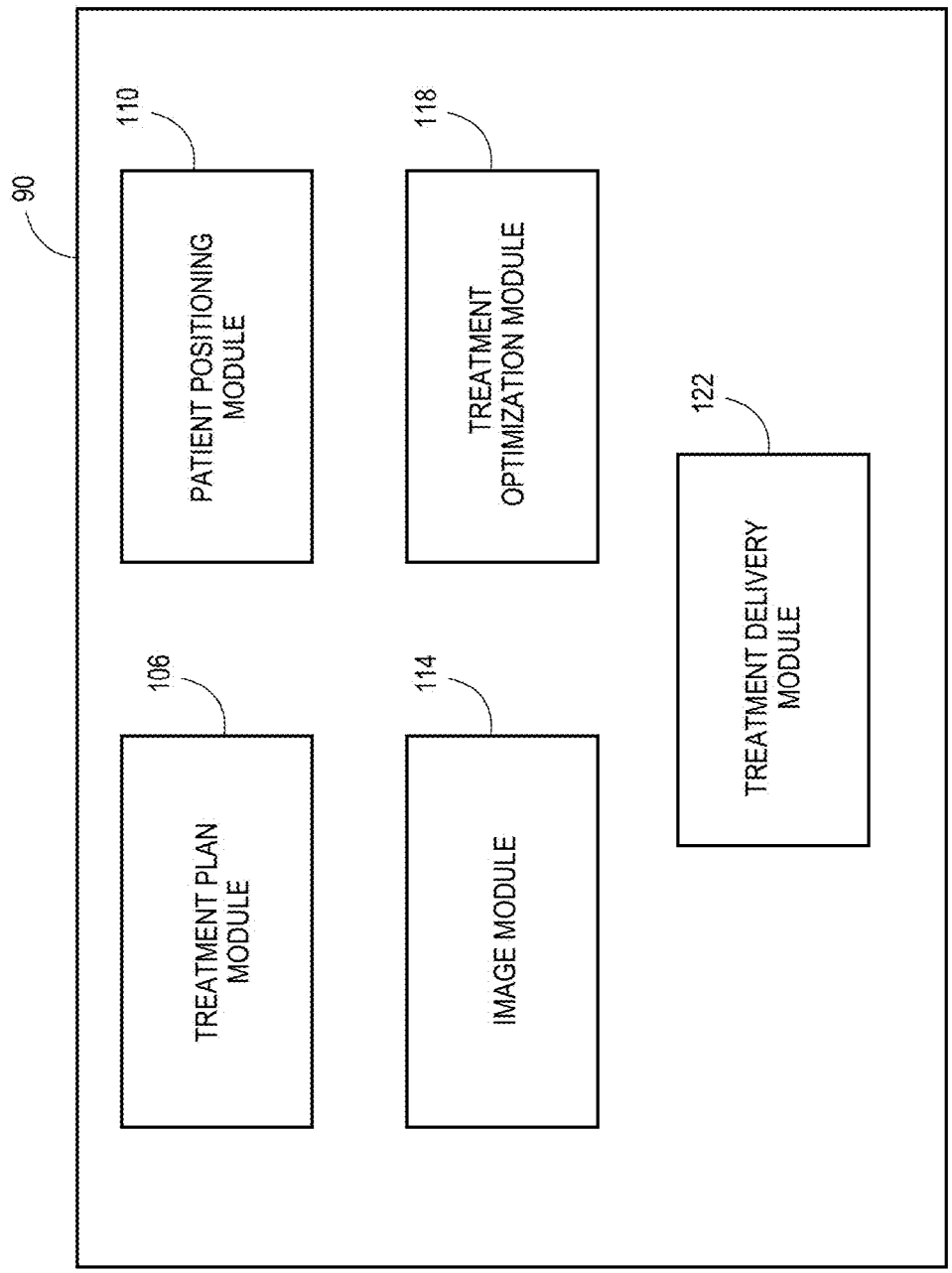
FIG. 25 is a schematic diagram of a software program used in the radiation therapy treatment system of FIGS. 23A and 23B.

In FIGS. 24-25, computer 74 includes an operating system for running various software programs and/or a communications application. In particular, computer 74 can include software program(s) 90 that operates to communicate with radiation therapy treatment system 10. Computer 74 can include typical hardware such as a processor, I/O interfaces, and storage devices or memory, keyboard, mouse, monitor. Computer 74 can be networked with other computers and radiation therapy treatment systems 10. The other computers may include additional and/or different computer programs and software and are not required to be identical to the computer 74, described herein. Computer(s) 74 and radiation therapy treatment system 10 can communicate with network 94 (FIG. 24). Computer(s) 74 and radiation therapy treatment system 10 can also communicate with database(s) 98 and server(s) 102. It is noted that the software program(s) 90 could also reside on the server(s) 102. Communication between the computers and systems shown in FIG. 24 can also occur through the digital imaging and communications in medicine (DICOM) protocol with any version and/or other required protocol. DICOM is an international communications standard developed by NEMA that defines the format used to transfer medical image-related data between different pieces of medical equipment. DICOM RT refers to the standards that are specific to radiation therapy data.

FIG. 25 is a schematic illustration of software program 90. Software program 90 includes a plurality of modules that communicate with one another to perform functions of the radiation therapy treatment process. The various modules are adapted to communicate with one another to plan and deliver radiation therapy to patient 14.

Software program 90 includes treatment plan module 106 operable to generate a treatment plan for patient 14 based on data input to system 10 by medical personnel, as previously described. The data includes one or more images (e.g., planning images and/or pre-treatment images) of at least a portion of patient 14. Treatment plan module 106 separates the treatment into a plurality of fractions and determines the radiation dose for each fraction or treatment based on the input from medical personnel. Treatment plan module 106 also determines the expected radiation dose for target 38 and surrounding critical structures based on contours drawn by the planner. Multiple targets 38 may be present and included in the same treatment plan.

Software program 90 also includes patient positioning module 110 operable to position and align patient 14 with respect to the isocenter of the gantry 18 or other reference for a particular treatment fraction based on a registration of an on-line CT image (preferably an MVCT image) with the planning CT image, commonly referred to as patient setup. It will be appreciated other patient setup procedures are well within common knowledge of the skilled artisan. The image registration provides offsets to the patient positioning module 110, which instructs drive system 86 to move couch 82 to align the patient relative to the treatment delivery system prior to treatment delivery, alternatively patient 14 can be manually moved to a new position or couch 82 can be manually adjusted. Patient positioning module 110 may also control movement of couch 82 during treatment in accordance with the treatment plan. In a robotically mounted system the offsets may be used to direct the robot to deliver radiation to the desired location within the patient, as is well known by the skilled artisan.

Software program 90 can also include image module 114 operable to acquire the on-line images of patient 14. Image module 114 can instruct the on-board image device, such as a CT imaging device, to acquire images of patient 14 before treatment commences, during treatment, and after treatment according to desired protocols. Other imaging devices may be used to acquire pre-treatment images of patient 14, such as non-quantitative CT, MRI, PET, SPECT, ultrasound, transmission imaging, fluoroscopy, RF-based localization, and the like. The acquired images can be used for registration of patient 14.

Software program 90 can also include treatment plan module 106 and treatment optimization module 118; preferably these two modules are included as a software product, the output of which is an optimized treatment plan for a patient that is ultimately approved by clinical professionals and provides direction to the treatment delivery system for delivering radiation to a patient. Treatment delivery module 122 uses the treatment plan as an input to control and guide delivery of radiation to the patient. As previously described, the treatment plan will include, but is not limited to, providing leaf positions, jaw positions, gantry angles and angular speed, and couch speed.

Referring again to FIG. 23A, radiation therapy treatment system 10 can also include detector 78, e.g., a kilovoltage or a megavoltage detector, operable to receive radiation beam 30. Linear accelerator 26 and detector 78 can also operate as a computed tomography (CT) system to generate CT images of patient 14. Linear accelerator 26 emits radiation beam 30 toward target 38 in patient 14. Target 38 and surrounding tissues absorb or attenuate some of the radiation. Detector 78 detects or measures the amount of radiation absorbed from different angles as linear accelerator 26 rotates around, which information is processed or reconstructed to generate images, preferably 3D CT images as is known in the art, of the patient's body tissues and organs. The images can also illustrate bone, soft tissues, and blood vessels. The CT images can be acquired with linear accelerator 26 delivering megavoltage energies or kilovoltage energies. Alternative gantry systems may permit acquisition of cone beam CT images. As will be appreciated by the skilled artisan, other sources of diagnostic x-ray energies (typically Kv energies) can be located on the gantry and be separate from the My therapeutic source.

Radiation therapy treatment system 10 can also include a patient support, such as couch 82 (illustrated in FIG. 23A), which supports patient 14. Couch 82 moves along at least one axis 84 in the x, y, or z directions, but may also include the ability to control pitch, roll and yaw. As described previously, the control systems can control couch velocity in accordance with the treatment plan and to achieve the desired intensity modulation. Patient support systems are well known in art and will not be further described here.

Various features and advantages of the invention are set forth in the following claims.

What is claimed is:

1. A multi leaf collimator (MLC) comprising:
a plurality of leaves having a length of travel, wherein each leaf comprises:
a blocking portion having a length L and a width W and being radio opaque, the blocking portion configured to block treatment level radiation,
a drive portion having a length L' and a width W', the drive portion connected to the blocking portion, the drive portion including a recessed portion, and
a conductive coil operatively connected to an electrical current source, wherein
the conductive coil is positioned in the recessed portion and fixed to the drive portion along at least a portion of length L', and wherein electrical current passing through the conductive coil generates a first magnetic field;
a leaf guide configured to support the plurality of leaves; and
a plurality of stationary magnets, each magnet positioned adjacent to the drive portion of at least one leaf, wherein each stationary magnet has a second magnetic field configured to operate in conjunction with the first magnetic field to exert a force on the drive portion.

2. The MLC of claim 1, wherein the MLC comprises a first bank including the plurality of leaves and a second bank including the plurality of leaves.

3. The MLC of claim 1, further comprising a first leaf position encoder.

4. The MLC of claim 3, further comprising a second leaf position encoder.

5. The MLC of claim 1, wherein the width W of the blocking portion is greater than the width W of the drive portion.

6. The MLC of claim 5, wherein the length of each of the plurality of stationary magnets (L") is selected such that the number of coils adjacent to the plurality of stationary magnets at any given time during leaf motion remains approximately constant.

7. A multi leaf collimator (MLC) comprising:
a plurality of leaves having a length of travel, wherein each leaf comprises:
a blocking portion having a length L and a width W and being radio opaque, the blocking portion configured to block treatment level radiation,
a drive portion having a length L' and a width W', the drive portion connected to the blocking portion, and
a conductive coil operatively connected to an electrical current source, wherein the conductive coil is fixed to the drive portion along at least a portion of length L', and wherein electrical current passing through the conductive coil generates a first magnetic field;
a leaf guide configured to support the plurality of leaves;
a plurality of stationary magnets, each magnet positioned adjacent to the drive portion of at least one leaf, wherein each stationary magnet has a second magnetic field configured to operate in conjunction with the first magnetic field to exert a force on the drive portion;
a magnetic drive module, the magnetic drive module including:
an upper portion having the drive portion of a first subset of the plurality of leaves extending therein and a first subset of the plurality of stationary magnets, wherein each stationary magnet of the first subset is positioned on either side of the drive portion of the first subset of the plurality of leaves;
a lower portion having the drive portion of a second subset of the plurality of leaves extending therein and a second subset of the plurality of stationary magnets, wherein each stationary magnet of the second subset is positioned on either side of the drive portion of the second subset of the plurality of leaves;
wherein the first subset of stationary magnets in the upper portion are horizontally offset from the second subset of stationary magnets in the lower portion; and
wherein the drive portion in the first subset and second subset of the plurality of leaves is alternatingly located in the upper portion and the lower portion for each adjacent leaf.

8. The MLC of claim 7, wherein the first subset of stationary magnets in the upper portion are horizontally offset from the second subset of stationary magnets in the lower portion by approximately a thickness of one leaf.

9. A system for collimating a therapeutic radiation beam, the system comprising:
a multi leaf collimator (MLC) comprising:
a plurality of leaves having a length of travel, wherein each leaf comprises
a blocking portion having a length L and a width W and being radio opaque, the blocking portion configured to block treatment level radiation,
a drive portion having a length L' and a width W', the drive portion connected to the blocking portion, the drive portion including a recessed portion, and
a conductive coil operatively connected to an electrical current source, wherein the coil is positioned in the recessed portion and fixed to the drive portion along at least a portion of the length L', and wherein electrical current passing through the coil generates a first magnetic field;
a leaf guide configured to support the plurality of leaves; and
a plurality of stationary magnets, each magnet positioned adjacent to the drive portion of at least one leaf, wherein each stationary magnet has a second magnetic field configured to operate in conjunction with the first magnetic field to exert a force on the drive portion; and
a driver component, wherein the driver component directs electrical current to the coil, thereby causing movement of the plurality of leaves to desired states.

10. A method for collimating a radiation beam with a multi leaf collimator (MLC), the method comprising:
determining a desired state for a leaf of the MLC, wherein the leaf is configured to block treatment level radiation;
activating a magnetic field of a conductive coil positioned in a recessed portion of the leaf, the leaf having a length of travel;
if the leaf is not in the desired state, modifying the magnetic field of the conductive coil to interact with a second magnetic field and result in a force on the leaf causing the leaf to move; and
stopping the leaf at the desired state anywhere along the length of travel.

11. The method of claim 10, wherein the leaf moves at a speed of at least 50 cm/s.

12. The method of claim 10 further comprising:
wherein modifying the magnetic field of the conductive coil when the leaf is not in the desired state includes applying an electrical current to the conductive coil residing within a driving portion of the leaf to generate a first magnetic field, wherein the first magnetic field operates in conjunction with the second magnetic field of stationary magnets on either side of the driving portion resulting in the force on the driving portion causing the leaf to move.

13. The method of claim 12, wherein stopping the leaf at the desired state comprises applying a braking force by modifying the electrical current to the conductive coil such that the first magnetic field operates in conjunction with the second magnetic field resulting in a braking force to the driving portion of the leaf.

14. The method of claim 10, wherein the radiation beam comprises one of photons, protons, and other ions.

15. A multi leaf collimator (MLC) comprising:
a plurality of leaves having a length of travel, wherein each leaf comprises
a blocking portion having a length L and a width W, wherein the blocking portion is radio opaque and configured to block treatment level radiation; and
a drive portion having a length L' and a width W', the drive portion connected to the blocking portion, the drive portion including a recessed portion, and
a conductive coil operatively connected to an electrical current source, the conductive coil positioned in the recessed portion and fixed to the drive portion along at least a portion of length L'; and
wherein at least one of the leaves is capable of moving at a speed of at least 50 cm/s and stopping at a position anywhere along the length of travel.

16. The MLC of claim 15, wherein at least one of the leaves is capable of stopping anywhere along the length of travel to within 100 microns or less of a desired position.

17. A multi leaf collimator (MLC) comprising:
a plurality of leaves having a length of travel, wherein each leaf comprises
  a blocking portion having a length L and a width W, wherein the blocking portion is radio opaque and configured to block treatment level radiation; and
  a drive portion having a length L' and a width W', the drive portion connected to the blocking portion;
wherein at least one of the leaves is capable of moving at a speed of at least 50 cm/s and stopping at a position anywhere along the length of travel;
a plurality of conductive coils operatively connected to an electrical current source, wherein each of the conductive coils is fixed to the drive portion of one of the leaves along at least a portion of length L', and wherein electrical current passing through the conductive coils generates a first magnetic field;
a leaf guide configured to support the plurality of leaves; and
a plurality of stationary magnets positioned adjacent to the drive portion, wherein each stationary magnet has a second magnetic field configured to operate in conjunction with the first magnetic field to exert a force on the drive portion.

18. The MLC of claim 17, wherein each of the plurality of stationary magnets is positioned one on either side of the drive portion.

19. A multi leaf collimator (MLC) comprising:
a plurality of leaves having a length of travel, wherein each leaf comprises:
  a blocking portion having a length L and a width W and being radio opaque, the blocking portion configured to block treatment level radiation,
  a drive portion having a length L' and a width W', the drive portion including a recessed portion and connected to the blocking portion, and
  a permanent magnet positioned in the recessed portion of the drive portion;
a leaf guide configured to support the plurality of leaves; and
a plurality of conductive coils, at least one coil positioned between adjacent leaves and connected to an electrical current source to generate a first magnetic field when current passes through the at least one coil that interacts with a second magnetic field generated by the magnet to exert a force on the drive portion.

20. The MLC of claim 19, wherein the width W of the blocking portion is greater than the width W' of the drive portion.

* * * * *